United States Patent
Moe et al.

(10) Patent No.: US 10,465,001 B2
(45) Date of Patent: *Nov. 5, 2019

(54) ANTIBODY BASED REAGENTS THAT SPECIFICALLY RECOGNIZE TOXIC OLIGOMERIC FORMS OF TAU

(71) Applicant: Oligomerix, Inc., New York, NY (US)

(72) Inventors: James G. Moe, Stamford, CT (US); Eliot J. Davidowitz, West Hempstead, NY (US)

(73) Assignee: Oligomerix, Inc., Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/424,444

(22) Filed: Feb. 3, 2017

(65) Prior Publication Data

US 2017/0210791 A1    Jul. 27, 2017

Related U.S. Application Data

(63) Continuation of application No. 14/434,742, filed as application No. PCT/US2013/065104 on Oct. 15, 2013, now Pat. No. 9,650,436.

(60) Provisional application No. 61/713,441, filed on Oct. 12, 2012.

(51) Int. Cl.

| | |
|---|---|
| *C07K 16/18* | (2006.01) |
| *G01N 33/68* | (2006.01) |
| *C07K 16/00* | (2006.01) |
| *C12N 15/10* | (2006.01) |
| *A61K 39/00* | (2006.01) |

(52) U.S. Cl.
CPC ............ *C07K 16/18* (2013.01); *C07K 16/005* (2013.01); *C12N 15/1037* (2013.01); *G01N 33/6896* (2013.01); *A61K 2039/505* (2013.01); *C07K 2317/21* (2013.01); *C07K 2317/30* (2013.01); *C07K 2317/62* (2013.01); *C07K 2317/622* (2013.01); *C07K 2317/76* (2013.01); *G01N 2333/47* (2013.01); *G01N 2333/4703* (2013.01); *G01N 2800/28* (2013.01); *G01N 2800/2814* (2013.01); *G01N 2800/2821* (2013.01); *G01N 2800/7047* (2013.01)

(58) Field of Classification Search
None
See application file for complete search history.

(56) References Cited

U.S. PATENT DOCUMENTS

| | | | |
|---|---|---|---|
| 7,332,580 B2* | 2/2008 | Adams ............... | C07K 16/2863 424/133.1 |
| 2015/0196663 A1* | 7/2015 | Shusta ................... | C07K 16/28 424/178.1 |
| 2015/0266947 A1* | 9/2015 | Sierks ................ | G01N 33/6896 424/135.1 |

FOREIGN PATENT DOCUMENTS

WO    WO 2011/026031    *  3/2011

OTHER PUBLICATIONS

Pansri "A compact phage display human scFv library for selection of antibodies to a wide variety of antigens" BMC biotech 9:6 (Year: 2009).*
Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*

* cited by examiner

*Primary Examiner* — Adam Weidner
(74) *Attorney, Agent, or Firm* — Sorell, Lenna & Schmidt LLP; William D. Schmidt

(57) ABSTRACT

The invention relates to antibodies, antibody fragments and binding agents that specifically recognize oligomeric tau but do not bind to monomelic tau, fibrillar tau or non-disease associated forms of tau.

22 Claims, 30 Drawing Sheets
Specification includes a Sequence Listing.

FIGURE 1

| size (nm) | AD Tau #1 | AD Tau #3 | Tau412M | Tau441M | Tau441O |
|---|---|---|---|---|---|
| <0.5 | 0.1820 | 0.1980 | 0.2961 | 0.3407 | 0.1930 |
| 0.5-1.0 | 5.0121 | 17.0796 | 13.3992 | 64.7279 | 5.7354 |
| 1.0-1.5 | 42.6321 | 58.3088 | 84.3994 | 34.0543 | 29.7952 |
| 1.5-2.0 | 42.3036 | 22.7722 | 1.8649 | 0.8122 | 49.5825 |
| 2.0-2.5 | 8.1772 | 0.4147 | 0.0183 | 0.0591 | 12.1121 |
| 2.5-3.0 | 1.0368 | 0.4868 | 0.0088 | 0.0011 | 0.9846 |
| 3.0-3.5 | 0.4055 | 0.2384 | 0.0050 | 0.0008 | 0.4601 |
| 3.5-4.0 | 0.1930 | 0.2773 | 0.0042 | 0.0004 | 0.3983 |
| 4.0-4.5 | 0.0488 | 0.1328 | 0.0008 | 0.0011 | 0.4147 |
| >4.5 | 0.0088 | 0.0916 | 0.0034 | 0.0023 | 0.3243 |
| total | 100.0000 | 100.0000 | 100.0000 | 100.0000 | 100.0000 |

FIGURE 3A

F9T AMINO ACID SEQUENCE

X E X V I Met K Y L L P T A A A G L L L L A A Q P A Met A Q V Q L Q E S G G G
V V Q P G R S L R L S C A A S G F T F S T S G Met H W V R Q A P G K G L E W V
A F I L H D G S D K Y Y A D S V K G R F T I S R D N S K N T L Y L Q Met N S L
R A E D T A I Y Y C A K S Q R E L L G A E Y L Q N W G Q G T L V T V S S G G G
G S G G G G S G G G G S Q S A L T Q P A S V S G S P G Q S I T I S C T G T S S
D V G G Y K Y V S W Y Q Q H P G K A P K V Met I Y D V S N R P S G V S N R F S
G S K S G N T A S L T I S G L Q A E D E A D Y Y C S S Y T S S S T L V F G G G
T K V T V L G A A A H H H H H H G A A E Q K L I S E E D X X X X (SEQ ID NO:1)

FIGURE 3B  BEFORE AND AFTER REPAIR

```
F9 (SEQ ID NO:2)    aattctatttcnggagacagtcataatgaaatacctattgcctacggcagccgctggatt
F9T-7(SEQ ID NO:3)  --------ttcnngaganagtcataatgaaatacctattgcctacggcagccgctggatt
                    ****.**** ***************************************************

F9                  gttattactcgcggcccagccggccatggcccaggtgcagctgcaggagtc-gggggagg
F9T-7               gttattactcgcggcccagccggccatggcccaggtgcagctgcaggagtctgggggagg
                    *************************************************** *******

F9                  cgtggtccagcctgggaggtccctgagactctcctgtgcagcgtctggattcaccttcag
F9T-7               cgtggtccagcctgggaggtccctgagactctcctgtgcagcgtctggattcaccttcag
                    ************************************************************

F9                  tacttctggcatgcactgggtccgccaggctccaggcaaggggctggagtgggtggcatt
F9T-7               tacttctggcatgcactgggtccgccaggctccaggcaaggggctggagtgggtggcatt
                    ************************************************************

F9                  tatactacatgatggaagtgataaatactatgcagactccgtgaagggccgattcaccat
F9T-7               tatactacatgatggaagtgataaatactatgcagactccgtgaagggccgattcaccat
                    ************************************************************

F9                  ctccagagacaattccaagaacacgctgtatctgcaaatgaacagcctgagagccgagga
F9T-7               ctccagagacaattccaagaacacgctgtatctgcaaatgaacagcctgagagccgagga
                    ************************************************************

F9                  cacggccatatattactgtgcgaaatctcagagggagctactcggcgctgaatacctcca
F9T-7               cacggccatatattactgtgcgaaatctcagagggagctactcggcgctgaatacctcca
                    ************************************************************

F9                  gaactggggccagggcaccctggtcaccgtctcctcaggtggaggcggttcaggcggagg
F9T-7               gaactggggccagggcaccctggtcaccgtctcctcaggtggaggcggttcaggcggagg
                    ************************************************************

F9                  tggctctggcggtggcggatcgcagtctgctctgactcagcctgcctccgtgtctgggtc
F9T-7               tggctctggcggtggcggatcgcagtctgctctgactcagcctgcctccgtgtctgggtc
                    ************************************************************
```

FIGURE 3B continued

```
F9      tcctggacagtcgatcaccatctcctgcactggaaccagcagtgacgttggtggttataa
F9T-7   tcctggacagtcgatcaccatctcctgcactggaaccagcagtgacgttggtggttataa
        ************************************************************

F9      gtatgtctcctggtaccaacagcacccaggcaaagcccccaaagtcatgatttatgatgt
F9T-7   gtatgtctcctggtaccaacagcacccaggcaaagcccccaaagtcatgatttatgatgt
        ************************************************************

F9      cagtaatcggccctcaggggtttctaatcgcttctctggctccaagtctggcaacacggc
F9T-7   cagtaatcggccctcaggggtttctaatcgcttctctggctccaagtctggcaacacggc
        ************************************************************

F9      ctccctgaccatctctgggctccaggctgaggacgaggctgattattactgcagctcata
F9T-7   ctccctgaccatctctgggctccaggctgaggacgaggctgattattactgcagctcata
        ************************************************************

F9      tacaagcagcagcactctcgtgttcggcggcgggaccaaggtcaccgtcctaggtgc---
F9T-7   tacaagcagcagcactctcgtgttcggcggcgggaccaaggtcaccgtcctaggtgcggc
        **********************************************************

F9      ------------------------ggccgcagaacaaaaactcatctcagaagaggatct
F9T-7   cgcacatcatcatcaccatcacgggggccgcagaacaaaaactcatctcagaagaggatcn
                                *********************************** .

F9      gaatggggccgcatanactgttgaaagttntttancaannntcatacnnaaaattcattt
F9T-7   naannnnncg--------------------------------------------------
        .**.....*

F9      actaacgtctggnaanacnacaaaactttnnatcgttangctaantnnnnnagggcngt
F9T-7   ------------------------------------------------------------
```

FIGURE 3C

>F9T
TTCNNGAGANAGTCATAATGAAATACCTATTGCCTACGGCAGCCGCTGGATTGTTATTACTCGCGGCCCAGCCGGCC
ATGGCCCAGGTGCAGCTGCAGGAGTCTGGGGGAGGCGTGGTCCAGCCTGGGAGGTCCCTGAGACTCTCCTGTGCAGC
GTCTGGATTCACCTTCAGTACTTCTGGCATGCACTGGGTCCGCCAGGCTCCAGGCAAGGGGCTGGAGTGGGTGGCAT
TTATACTACATGATGGAAGTGATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCCATATATTACTGTGCGAAATCTCAGAG
GGAGCTACTCGGCGCTGAATACCTCCAGAACTGGGGCCAGGGCACCCTGGTCACCGTCTCCTCAGGTGGAGGCGGTT
CAGGCGGAGGTGGCTCTGGCGGTGGCGGATCGCAGTCTGCTCTGACTCAGCCTGCCTCCGTGTCTGGGTCTCCTGGA
CAGTCGATCACCATCTCCTGCACTGGAACCAGCAGTGACGTTGGTGGTTATAAGTATGTCTCCTGGTACCAACAGCA
CCCAGGCAAAGCCCCCAAAGTCATGATTTATGATGTCAGTAATCGGCCCTCAGGGGTTTCTAATCGCTTCTCTGGCT
CCAAGTCTGGCAACACGGCCTCCCTGACCATCTCTGGGCTCCAGGCTGAGGACGAGGCTGATTATTACTGCAGCTCA
TATACAAGCAGCAGCACTCTCGTGTTCGGCGGCGGGACCAAGGTCACCGTCCTAGGTGCGGCCGCACATCATCATCA
CCATCACGGGGCCGCAGAACAAAAACTCATCTCAGAAGAGGATCNNAANNNNNCG (SEQ ID NO:4)

FIGURE 3C continued

>F9
AATTCTATTTCNGGAGACAGTCATAATGAAATACCTATTGCCTACGGCAGCCGCTGGATTGTTATTACTCGCGGCCC
AGCCGGCCATGGCCCAGGTGCAGCTGCAGGAGTCGGGGGAGGCGTGGTCCAGCCTGGGAGGTCCCTGAGACTCTCCT
GTGCAGCGTCTGGATTCACCTTCAGTACTTCTGGCATGCACTGGGTCCGCCAGGCTCCAGGCAAGGGGCTGGAGTGG
GTGGCATTTATACTACATGATGGAAGTGATAAATACTATGCAGACTCCGTGAAGGGCCGATTCACCATCTCCAGAGA
CAATTCCAAGAACACGCTGTATCTGCAAATGAACAGCCTGAGAGCCGAGGACACGGCCATATATTACTGTGCGAAAT
CTCAGAGGGAGCTACTCGGCGCTGAATACCTCCAGAACTGGGGCCAGGGCACCCTGGTCACCGTCTCCTCAGGTGGA
GGCGGTTCAGGCGGAGGTGGCTCTGGCGGTGGCGGATCGCAGTCTGCTCTGACTCAGCCTGCCTCCGTGTCTGGGTC
TCCTGGACAGTCGATCACCATCTCCTGCACTGGAACCAGCAGTGACGTTGGTGGTTATAAGTATGTCTCCTGGTACC
AACAGCACCCAGGCAAAGCCCCCAAAGTCATGATTTATGATGTCAGTAATCGGCCCTCAGGGGTTTCTAATCGCTTC
TCTGGCTCCAAGTCTGGCAACACGGCCTCCCTGACCATCTCTGGGCTCCAGGCTGAGGACGAGGCTGATTATTACTG
CAGCTCATATACAAGCAGCAGCACTCTCGTGTTCGGCGGCGGGACCAAGGTCACCGTCCTAGGTGCGGCCGCAGAAC
AAAAACTCATCTCAGAAGAGGATCTGAATGGGGCCGCATANACTGTTGAAAGTTNTTTANCAANNNTCATACNNAAA
ATTCATTTACTAACGTCTGGNAANACNACAAAACTTTNNATCGTTANGCTAANTNNNNNAGGGCNGT (SEQ ID
NO:5)

>F9T-7L
TTCNNGAGANAGTCATAATGAAATACCTATTGCCTACGGCAGCCGCTGGATTGTTATTACTCGCGGCCCAGCCGGCC
ATGGCCCAGGTGCAGCTGCAGGAGTCTGGGGGAGGCGTGGTCCAGCCTGGGAGGTCCCTGAGACTCTCCTGTGCAGC
GTCTGGATTCACCTTCAGTACTTCTGGCATGCACTGGGTCCGCCAGGCTCCAGGCAAGGGGCTGGAGTGGGTGGCAT
TTATACTACATGATGGAAGTGATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCCATATATTACTGTGCGAAATCTCAGAG
GGAGCTACTCGGCGCTGAATACCTCCAGAACTGGGGCCAGGGCACCCTGGTCACCGTCTCCTCAGGTGGAGGC
GGTTCAGGCGGAGGTGGCTCTGGCGGTGGCGGATCGCAGTCTGCTCTGACTCAGCCTGCCTCCGTGTCTGGGTCTCC
TGGACAGTCGATCACCATCTCCTGCACTGGAACCAGCAGTGACGTTGGTGGTTATAAGTATGTCTCCTGGTACCAAC
AGCACCCAGGCAAAGCCCCCAAAGTCATGATTTATGATGTCAGTAATCGGCCCTCAGGGGTTTCTAATCGCTTCTCT
GGCTCCAAGTCTGGCAACACGGCCTCCCTGACCATCTCTGGGCTCCAGGCTGANGACGAGGCTGATTATTACTGCAG
CTCATATACAAGCAGCAGCACTCTCGTGTTCGNNGGCGGGACCAAGGTCACCGTCCTNNNGCGGCCGCACATCATCA
TCACCATCACGGGGCCGCNGACAAAACTCATCTCNNANAGGATCTGAATGGGCCGCNTANACTGNTGAAAGTTGTTA
NCAAAACCTCNTACNNAAAATTCATTTACTAACGTCTGGAAAGANNNNNAACTTTANATNGTTANNNNAACNATGNN
NNNGN (SEQ ID NO:6)

>F9T-7F-RC
GNNNNNTNNNNGGAANTGNGAGCNNNNNNAATTTNNCNCAGGAAACAGCTATGACCANGATTACGCCAAGCTTGCAT
GCAAATTNTATTTCAAGGAGACAGTCATAATGAAATACNTATTGCNTACNNNCANNCNNNGGATNNTATTACTCGCG
GCCCAGCCGGCCATGGCCCAGGTGCAGCTGCAGGAGTCTGGGGGAGGCGTGNTCCAGCCTGGGAGGTNCNNGAGACT
CTCCTGTGCAGCGTCTGGATTCACCTTCAGTACTTCTGGCATGCACTGGGTCCGCCAGGCTCCAGGCAAGGGGCTGG
AGTGGGTGGCATTTATACTACATGATGGAAGTGATAAATACTATGCAGACTCCGTGAAGGGCCGATTCACCATCTCC
AGAGACAATTCCAAGAACACGCTGTATCTGCAAATGAACAGCCTGAGAGCCGAGGACACGGCCATATATTACTGTGC
GAAATCTCAGAGGGAGCTACTCGGCGCTGAATACCTCCAGAACTGGGGCCAGGGCACCCTGGTCACCGTCTCCTCAG
GTGGAGGC
GGTTCAGGCGGAGGTGGCTCTGGCGGTGGCGGATCGCAGTCTGCTCTGACTCAGCCTGCCTCCGTGTCTGGGTCTCC
TGGACAGTCGATCACCATCTCCTGCACTGGAACCAGCAGTGACGTTGGTGGTTATAAGTATGTCTCCTGGTACCAAC
AGCACCCAGGCAAAGCCCCCAAAGTCATGATTTATGATGTCAGTAATCGGCCCTCAGGGGTTTCTAATCGCTTCTCT
GGCTCCAAGTCTGGCAACACGGCCTCCCTGACCATCTCTGGGCTCCAGGCTGAGGACGAGGCTGATTATTACTGCAG
CTCATATACAAGCAGCAGCACTCTCGTGTTCGGCGGCGGGACCAAGGTCACCGTCCTAGGTGCGGCCGCACATCATC
ATCACCATCACGGGGCCGCAGAACAAAAACTCATCTCAGAAGAGGATCNNAANNNNNCG (SEQ ID NO:7)

AATTCTATTTCNGGAGACAGTCATAATGAAATACCTATTGCCTACGGCAGCCGCTGGATTGTTATTACTCGCGGCCC
AGCCGGCCATGGCCCAGGTGCAGCTGCAGGAGTCTGGGGGAGGCGTGGTCCAGCCTGGGAGGTCCCTGAGACTCTCC
TGTGCAGCGTCTGGATTCACCTTCAGTACTTCTGGCATGCACTGGGTCCGCCAGGCTCCAGGCAAGGGGCTGGAGTG
GGTGGCATTTATACTACATGATGGAAGTGATAAATACTATGCAGACTCCGTGAAGGGCCGATTCACCATCTCCAGAG
ACAATTCCAAGAACACGCTGTATCTGCAAATGAACAGCCTGAGAGCCGAGGACACGGCCATATATTACTGTGCGAAA
TCTCAGAGGGAGCTACTCGGCGCTGAATACCTCCAGAACTGGGGCCAGGGCACCCTGGTCACCGTCTCCTCAGGTGG
AGGCGGTTCAGGCGGAGGTGGCTCTGGCGGTGGCGGATCGCAGTCTGCTCTGACTCAGCCTGCCTCCGTGTCTGGGT
CTCCTGGACAGTCGATCACCATCTCCTGCACTGGAACCAGCAGTGACGTTGGTGGTTATAAGTATGTCTCCTGGTAC
CAACAGCACCCAGGCAAAGCCCCCAAAGTCATGATTTATGATGTCAGTAATCGGCCCTCAGGGGTTTCTAATCGCTT
CTCTGGCTCCAAGTCTGGCAACACGGCCTCCCTGACCATCTCTGGGCTCCAGGCTGAGGACGAGGCTGATTATTACT
GCAGCTCATATACAAGCAGCAGCACTCTCGTGTTCGGCGGCGGGACCAAGGTCACCGTCCTAGGT*GCGGCCGC*AGAA
CAAAAACTCATCTCAGAAGAGGATCTGAATGGGGCCGCATANACTGTTGAAAGTTNTTTANCAANNNTCATACNNAA
AATTCATTTACTAACGTCTGGNAANACNACAAAACTTTNNATCGTTANGCTAANTNNNNNAGGGCNGT (SEQ ID NO:8)

I L F X E T V I Met K Y L L P T A A A G L L L L A A Q P A Met A Q V Q L Q E
S G G G V V Q P G R S L R L S C A A S G F T F S T S G Met H W V R Q A
P G K G L E W V A F I L H D G S D K Y Y A D S V K G R F T I S R D N S K
N T L Y L Q Met N S L R A E D T A I Y Y C A K S Q R E L L G A E Y L Q N
W G Q G T L V T V S S G G G G S G G G G S G G G G S Q S A L T Q P A S
V S G S P G Q S I T S C T G T S S D V G G Y K Y V S W Y Q Q H P G K A
P K V Met I Y D V S N R P S G V S N R F S G S K S G N T A S L T I S G L Q
A E D E A D Y Y C S S Y T S S S T L V F G G G T K V T V L G A A A E Q K
L I S E E D L N G A A X T V E S X L X X X I X K I H L L T S X X X T K L X I V
X L X X X G X (SEQ ID NO:9)

GCANTTCNATTTNNNGAGACAGTCATAATGAAATACCTATTGCCTACGGCAGCCGCTGGATTGTTATTACTCGCGGC
CCAGCCGG*CCATGCC*CCAGGTGCAGCTGGTGGAGTCTGGGGGAGGCTTGGTACAGCCTGGGGGGTCCCTGAGACTCT
CCTGTGCAGCCTCTGGATTCACCTTTTAGCAGCTATGCCATGAGCTGGGTCCGCCAGGCTCCAGGGAAGGGGCTGGAG
TGGGTCTCAGCTATTAGTGGTAGTGGTGGTAGCACATACTACGCAGACTCCGTGAAGGGCCGGTTCACCATCTCCAG
AGACAATTCCAAGAACACGCTGTATCTGCAAATGAACAGCCTGAGAGCCGAGGACACGGCTGTATATTACTGTGCAA
GAGGTGGCGATTATGGCTCAGGGGACTACTGGGGCCAGGGAACCCTGGTCACCGTCTCCTCAGGTGGAGGCGGTTCA
GGCGGAGGTGGCTCTGGCGGTGGCGGATCGAATTTTATGCTGACTCAGGACCCTGCTGTGTCTGTGGCCTTGGGACA
GACAGTCAGAATCACATGCCAAGGAGACAGCCTCAGAAGCTATTATGCAAGTTGGTACCAGCAGAAGCCAGGACAGG
CCCCTCTCCTTGTCATCTATGGTAAAAACATCCGGCCCTCAGGGATCCCAGACCGATTCTCTGGCTCCAGCTCAGGA
AACTCAGCTTCCTTGACCATCACTGGGCTCAGGCGGAAGATGAGGCTGACTATTACTGTCACTCCCGGGACAGCAG
TGGTACCCATCTAAGGGTATTCGGCGGAGGGACCAAGGTCACCGTCCTAGGT*GCGGCCGC*AGAACAAAAACTCATCT
CAGAAGAGGATCTGAATGGGGCCGCATANACTGTTGAAAGTTGTTTANCAAANNCTCATACAGAAANTTNATTNNCT
ANNNTCTGGNAAGANGACAAAACTTTNNNTCGTNACGCTANNNNTNNNNNNTGTCTGTGANNGCNNCNGGCNNTGTG
NTNNNNACTGNNNNNNNAAANTNNNGNTNNNNG (SEQ ID NO:10)

FIGURE 4B continued

A X X F X E T V I Met K Y L L P T A A A G L L L L A A Q P A Met A Q V Q L
V E S G G G L V Q P G G S L R L S C A A S G F T F S S Y A Met S W V R
Q A P G K G L E W V S A I S G S G G S T Y Y A D S V K G R F T I S R D N
S K N T L Y L Q Met N S L R A E D T A V Y Y C A R G G D Y G S G D Y W
G Q G T L V T V S S G G G G S G G G G S G G G G S N F Met L T Q D P A
V S V A L G Q T V R I T C Q G D S L R S Y Y A S W Y Q Q K P G Q A P L L
V I Y G K N I R P S G I P D R F S G S S S G N S A S L T I T G A Q A E D E
A D Y Y C H S R D S S G T H L R V F G G G T K V T V L G A A A E Q K L I
S E E D L N G A A X T V E S C L X X X H T E X X X X X X W X X D K T X X
R X A X X X X C L Stop X X X X X X X X L X X K X X X X (SEQ ID NOS11+43)

FIGURE 4C

>D4G
GCNNNTCTATTTAAGGAGACAGTCATAATGAAATACCTATTGCCTACGGCAGCCGCTGGATTGTTATTACTCGCGGC
CCAGCCGGCCATGGCCCAGGTGCAGCTGGTGGCGTCTGGAGGAGACTTTGATCCAGCCTGGGGGGTCCCTGAGACTCT
CCTGTGCAGCCTCTGGATTCACCTTTAATAACTATTGGATGACCTGGGTCCGCCAGGCTCCAGGGAAGGGGCTGGAG
TGGGTGGCCAACATAAAGCAAGATGGAGGTGAGAAATACTATGTGGACTCTGTGAAGGGCCGATTCACCATCTCCAG
AGACAACGCCAAGACCTCACTGTATCTGCAAATGAACAGCCTGAGAGCCGAGGACACGGCCGTGTATTATTGTGCGA
AAGAGTCGTATAGCACTGGCTGGTTTGACCACTGGGGCCAGGGAACCCTGGTCACCGTCTCCTCAGGTGGAGGCGGT
TCAGGCGGAGGTGGCTCTGGCGGTGGCGGATCGAATTTTATGCTGACTCAGGACCCTGCTGTGTCTGTGGCCTTGGG
ACAGACAGTCAGGATAACATGTCAAGGTGACAGCCTCAGAAAATATTATACAAGTTGGTACCAACAGAAGCCAGGAC
AGGCCCCTCTACTTGTCATGTATGCGAAAAATAACCGGCCCTCAGGGATCCCAGACCGATTCTCTGGCTCCAGCTCA
GGAAACACAGCTTCCTTGACCATCACTGGGGCTCAGGCGGAAGATGAGGCTGACTATTACTGTGACTCCCGGGACAG
CAGTGGTGACCATTGGGTGTTCGGCGGAGGGACCAAGCTGACCGTTCTAGGT*GCGGCCGC*AGAACAAAAACTCATCT
CAGAAGAGGATCTGAATGGGGCCGCATANACTGTTGAAAGTTGTTTANCAAAACCTCNTANNNAAAATTCATTTACT
AAANGTCTGGAAAGACGACAAAACTTTANNTCGTTACGCTAACTATGNNGGCTGNCTGNNGNANGCTACNG (SEQ ID NO:12)

X X L F K E T V I Met K Y L L P T A A A G L L L L A A Q P A Met A Q V Q L
V A S G G D L I Q P G G S L R L S C A A S G F T F N N Y W Met T W V R Q
A P G K G L E W V A N I K Q D G G E K Y Y V D S V K G R F T I S R D N A
K T S L Y L Q Met N S L R A E D T A V Y Y C A K E S Y S T G W F D H W G
Q G T L V T V S S G G G G S G G G G S G G G G S N F Met L T Q D P A V
S V A L G Q T V R I T C Q G D S L R K Y Y T S W Y Q Q K P G Q A P L L
V Met Y A K N N R P S G I P D R F S G S S S G N T A S L I T G A Q A E D
E A D Y Y C D S R D S S G D H W V F G G G T K L T V L G A A A E Q K L I
S E E D L N G A A X T V E S C L X K P X X X N S F T X V W K D D K T L X
R Y A N Y X G X L X X A X (SEQ ID NO:13)

TNNNNTTNNNGAGACAGTCATAATGAAATACCTATTGCCTACGGCAGCCGCTGGATTGTTATTACTCGCGGCCCAGC
CGGCCATGGCCCGAGTGCAGCTGGTGGAGTCTGGGGCTGAGGTGACGAAGCCTGGGGCCTCAGTAAGGGTCTCCTGC
AAGGCTTCTGGATACACCTTCAGCAGATATGATATCAACTGGGTGCGACAGGCCTCTGGACAAGGGCTTGAGTGGAT
GGGATGGATCAACCCTAACAGTGGTAACACAGGCTATGCACAGAAGTTCCAGGGCAGAGTCACCATGACCAGGAATA
TTTCCATAACCACGGCCTACATGGAGCTGAGCAGCCTGAGATCTGAGGACACGGCCGTATATTACTGTGCGAGAGGC
CTTCCGGAGTTCGACCCCTGGGGCCAGGGAACCCTGGTCACCGTCTCCTCAGGTGGAGGCGGTTCAGGCGGAGGTGG
CTCTGGCGGTGGCGGATCGCACGTTATACTGACTCAGGACCCTGCTGTGTCTGTGGCCTTGGGACAGACAGTCAGGA
TCACATGCCAAGGAGACAGCCTCAGAAGCTATTATGCAAGCTGGTACCAGCAGAAGCCAGGACAGGCCCCTGTACTT
GTCATCTATGGTAAAAACAACCGGCCCTCAGGGATCCCAGACCGATTCTCTGGCTCCAGCTCAGGAAACACAGCTTC
CTTGACCATCACTGGGGCTCAGGCGGAAGATGAGGCTGACTTTTACTGTAATTCCCGGGACAGCAGTGGCACCCATC
TAGAGGTGTTCGGCGGAGGGACCAAGGTCACCGTCCTAGGT*GCGGCCGC*AGAACAAAAACTCATCTCAGAAGAGGAT
CTGAATGGGGCCGCATANACTGNTGAAAGTTGTTTANCAAAACCTCNTACAGAAAATTCATTTACTAACGTCTGGAA
AGACGANAAAACTTTANATCGTTACNCTAACTATNNNGGNTGTCTGNGNANTGNTAC (SEQ ID NO:14)

A X X X E T V I Met K Y L L P T A A A G L L L L A A Q P A Met A R V Q L V
E S G A E V T K P G A S V R V S C K A S G Y T F S R Y D I N W V R Q A S
G Q G L E W Met G W I N P N S G N T G Y A Q K F Q G R V T Met T R N I
S I T T A Y Met E L S S L R S E D T A V Y Y C A R G L P E F D P W G Q G
T L V T V S S G G G G S G G G G S G G G G S H V I L T Q D P A V S V A L
G Q T V R I T C Q G D S L R S Y Y A S W Y Q Q K P G Q A P V L V I Y G K
N N R P S G I P D R F S G S S S G N T A S L T I T G A Q A E D E A D F Y C
N S R D S S G T H L E V F G G G T K V T V L G A A A E Q K L I S E E D L N
G A A X T X E S C L X K P X T E N S F T N V W K D X K T L X R Y X N Y X
X C L X X X (SEQ ID NO:15)

ANTTCTATTTNNNGAGACAGTCATAATGAAATACCTATTGCCTACGGCAGCCGCTGGATTGTTATTACTCGCGGCCC
AGCCGG*CCATGGCCC*AGGTACAGCTGCAGGAGTCTGGGGGAGGCTTGGTCCAGCCTGGGAGGTCCCTGAGACTCTCC
TGTGCAGCCTCTGGATTCACCTTCAGTAACTTTGGCATGCACTGGGTCTGCCAGGCTCCAGGCAAGGGGCTGGAGTG
GGTGGCAATTATTTCATATGATGCAAGTAGTGAATACTATGCAGACTCCGTGAAGGGCCGATTCACCATCTCCAGAG
ACAATTCCAGGAACACTCTTTATCTGCAAATGAACAGCCTGAGACCTGAGGACACGGCTGTATATTACTGTGCGAAG
AAGGACGGTCGGAGTGGGAGCTACTACTACTTTGACTACTGGGGCCAGGGAACCCTGGTCACCGTCTCCTCAGGTGG
AGGCGGTTCAGGCGGAGGTGGCTCTGGCGGTGGCGGATCGGATGTTGTGATGACTCAGTCTCCATCCTCCCTGTCTG
CATCTGTAGGAGACAGAGTCACCATCACTTGCCGGGCAGTCAAGATTTTAGGAATTGGTTAGCCTGGTATCAGGTG
AAACCAGGAAAAGCCCCAAGCCCCTGATCTATGGTGCATCCACTTTGCAAAATGGGGTCCCATCCAGGTTCAGCGG
CAGTGGGTCTGANACAGATTTCTCTCTCACTATCAGCAGCCTGCAGCCTGAGNANTTTGCAACTTACTTTTGTCAAC
NNNTCACAGTTTCCCTCCCACTTTCNCGGAGGNACACGACTGGANATCAAACGT*GCGGCCGC*NCATCATCATCACCA
TCANGGGNCNCNNANAAAACTCATCTCNAANAGGANCTGAATGGGCCGCATANACTGTGAAGTTGNTTANCAAACTC
NTANNNNANTNNTTTACTANGNCNGNNNANNANNAACTTAANTCNTNCNCTANNNNGANGNNNNCNNNGNANGNNAN
NNNNNNNNNNNGNTNNNACNGNNNNNNNANNNNNNGNTACNG (SEQ ID NO:16)

FIGURE 4E continued

X L F X E T V I Met K Y L L P T A A A G L L L L A A Q P A Met A Q V Q L Q
E S G G G L V Q P G R S L R L S C A A S G F T F S N F G Met H W V C Q
A P G K G L E W V A I I S Y D A S S E Y Y A D S V K G R F T I S R D N S R
N T L Y L Q Met N S L R P E D T A V Y Y C A K K D G R S G S Y Y Y F D Y
W G Q G T L V T V S S G G G G S G G G G S G G G G S D V V Met T Q S
P S S L S A S V G D R V T I T C R A S Q D F R N W L A W Y Q V K P G K A
P K P L I Y G A S T L Q N G V P S R F S G S G S X T D F S L T I S S L Q P
E X F A T Y F C Q X X T V S L P L X R R X T T G X Q T C G R X S S S P S
X X X X K T H L X X X L N G P H X L Stop S X L X N X X X X X L L X X X X
X N L X X X L X X X X X X X X X X X X X X X X X X X X Y X (SEQ ID NOS: 17+44)

GNNNNTCNATTTNNNGAGACAGTCATAATGAAATACCTATTGCCTACGGCAGCCGCTGGATTGTTATTACTCGCGGC
CCAGCCGG*CCATG*GCCCAGGTGCAGCTGCAGGAGTCTGGGGGAGACGTGGTCCAGCCTGGGAGGTCCCTGAGACTCT
CCTGTGCAGCCTCTGGATTCACCTTCAGTAGCTATGGCATGCACTGGGTCCGCCAGGCTCCAGGCAAGGGGCTGGAG
TGGGTGGCAGTTATATCATATGATGAAAGTAATAAATACTATGCAGACTCCGTGAAGGGCCGATTCACCATCTCCAG
AGACAATTCCAAGAACACACTGTTTCTGCAAATGAACAGCCTGAGGACTGAGGACACGGCTGTGTATTACTGTGCGA
AAGGACCTGTCCTAACTGGGGAGTTTGACTATTGGGGCCGTAGAACCCTGGTCACCGTCTCCTCAGGTGGAGGCGGT
TCAGGCGGAGGTGGCTCTGGCGGTGGCGGATCGTCTGAGCTGACTCAGGACCCTGCTGTGTCTGTGGCCTTGGGACA
GACAGTCAGGATCACATGCCAAGGAGACAGCCTCAAAAGCTACTATGCAAGTTGGTACCAGCAGAAGCCAGGACAGG
CCCCTGTACTTGTCATCTATGGTGAAAACAGCCGGCCCTCCGGGATCCCAGACCGATTCTCTGGTTCCAGCTCANGA
AACACAGCTTCCTTGACCATCACTGGGGGCTCANGCGGAAGATGAAGCTGACTATTATTGTAACTCCCGGGACAACA
GTGGTACCCATCTTGAGGTATTCGGCGGAGGGACCAAGCTGACCGTCCTAGGT*GCGGCCGC*AGAACAAAAACTCATC
TCAGAAGAGGATCTGAATGGGGCCGCATANACTGTTGAAAGTTGTTTANCNAAACCTCATACNNAAAAATTCATTTAC
TAACGTCTGGNAANACNACAAACTTTANATCGTTACGCTAACTATGAGGGCTGTCNGNGNAATGC (SEQ ID NO:18)

X X X F X E T V I Met K Y L L P T A A A G L L L L A A Q P A Met A Q V Q L
Q E S G G D V V Q P G R S L R L S C A A S G F T F S S Y G Met H W V R
Q A P G K G L E W V A V I S Y D E S N K Y Y A D S V K G R F T I S R D N
S K N T L F L Q Met N S L R A E D T A V Y Y C A K G P V L T G E F D Y W
G R R T L V T V S S G G G G S G G G G S G G G G S S E L T Q D P A V S
V A L G Q T V R I T C Q G D S L K S Y Y A S W Y Q Q K P G Q A P V L V I
Y G E N S R P S G I P D R F S G S S S X N T A S L T I T G G S X G
R Stop S Stop L L L Stop L P G Q Q W Y P S Stop G I R R R D Q A D R P
R C G R R T K T H L R R G S E W G R I X C Stop K L F X X T S Y X K F I
Y Stop R L X X X Q T L X R Y A N Y E G C X X N (SEQ ID NOS: 19&45+50)

Gagacagtcataatgaaatacctattgcctacggcagccgctggattgttattactcgcggcccagccggccatggc
ccaggtacagctgcaggagtctgggggaggcttggtacagcctggggggtccctgagactctcctgtgcagcctctg
gattcacctttagcagctatgccatgagctgggtccgccaggctccagggaagggggctggagtggtctcagctatt
agtggtagtggtggtagcacatactacgcagactccgtgaaggccgattcaccatctccagagacaattccaagaa
cacgctgtatctgcaaatgaacagcctgagagctgaggacacggctgtgtattactgtgcgaagagctatggttcag
ttaaaataagctgctttgactactggggccagagcaccctggtcaccgtctcctcaggtggagcggttcaggcgga
ggtggctctggcggtggcggatcggaaattgtgctgacgcagtctccagactccctgctgtgtctctgggcgagag
ggccaccatcaactgcaagtccagccagagtgttctttacaactccaacaataagaactacttagcttggtaccagc
agaaaccaggacagtctcctgagttgctcatttactgggcatcaacccggggaatccggggtccctgaccgattcagt
ggcagcgggtctgggacagaattcactcttaccatcagcagcctgcaggctgaggatgtggcagtttattactgtca
gcaattttatagtactcctccgacttttggccaggggaccaagctggagatcaaacg*tgcggccgc*acatcatcatc
accatcacgggccgcagaacaaaaactcatctcagaagaggatc (SEQ ID NO:20)

>F9T

AATTCTATTTCNGGAGACAGTCATAATGAAATACCTATTGCCTACGGCAGCCGCTGGATTGTTATTACTCGCGGCCC
AGCCGGCCATGGCCCAGGTGCAGCTGCAGGAGTCTGGGGGAGGCGTGGTCCAGCCTGGGAGGTCCCTGAGACTCTCC
TGTGCAGCGTCTGGATTCACCTTCAGTACTTCTGGCATGCACTGGGTCCGCCAGGCTCCAGGCAAGGGGCTGGAGTG
GGTGGCATTTATACTACATGATGGAAGTGATAAATACTATGCAGACTCCGTGAAGGGCCGATTCACCATCTCCAGAG
ACAATTCCAAGAACACGCTGTATCTGCAAATGAACAGCCTGAGAGCCGAGGACACGGCCATATATTACTGTGCGAAA
TCTCAGAGGGAGCTACTCGGCGCTGAATACCTCCAGAACTGGGGCCAGGGCACCCTGGTCACCGTCTCCTCAGGTGG
AGGCGGTTCAGGCGGAGGTGGCTCTGGCGGTGGCGGATCGCAGTCTGCTCTGACTCAGCCTGCCTCCGTGTCTGGGT
CTCCTGGACAGTCGATCACCATCTCCTGCACTGGAACCAGCAGTGACGTTGGTGGTTATAAGTATGTCTCCTGGTAC
CAACAGCACCCAGGCAAAGCCCCCAAAGTCATGATTTATGATGTCAGTAATCGGCCCTCAGGGGTTTCTAATCGCTT
CTCTGGCTCCAAGTCTGGCAACACGGCCTCCCTGACCATCTCTGGGCTCCAGGCTGAGGACGAGGCTGATTATTACT
GCAGCTCATATACAAGCAGCAGCACTCTCGTGTTCGGCGGCGGGACCAAGGTCACCGTCCTAGGT*GCGGCCGC*AGAA
CAAAAACTCATCTCAGAAGAGGATCTGAATGGGGCCGCATANACTGTTGAAAGTTNTTTANCAANNNTCATACNNAA
AATTCATTTACTAACGTCTGGNAANACNACAAAACTTTTNNATCGTTANGCTAANTNNNNNAGGGCNGT (SEQ ID NO:8)

>D11C

GCANTTCNATTTTNNNGAGACAGTCATAATGAAATACCTATTGCCTACGGCAGCCGCTGGATTGTTATTACTCGCGGC
CCAGCCGGCCATGGCCCAGGTGCAGCTGGTGGAGTCTGGGGGAGGCTTGGTACAGCCTGGGGGGTCCCTGAGACTCT
CCTGTGCAGCCTCTGGATTCACCTTTAGCAGCTATGCCATGAGCTGGGTCCGCCAGGCTCCAGGGAAGGGGCTGGAG
TGGGTCTCAGCTATTAGTGGTAGTGGTGGTAGCACATACTACGCAGACTCCGTGAAGGGCCGGTTCACCATCTCCAG
AGACAATTCCAAGAACACGCTGTATCTGCAAATGAACAGCCTGAGAGCCGAGGACACGGCTGTATATTACTGTGCAA
GAGGTGGCGATTATGGCTCAGGGGACTACTGGGGCCAGGGAACCCTGGTCACCGTCTCCTCAGGTGGAGGCGGTTCA
GGCGGAGGTGGCTCTGGCGGTGGCGGATCGAATTTTATGCTGACTCAGGACCCTGCTGTGTCTGTGGCCTTGGGACA
GACAGTCAGAATCACATGCCAAGGAGACAGCCTCAGAAGCTATTATGCAAGTTGGTACCAGCAGAAGCCAGGACAGG
CCCCTCTCCTTGTCATCTATGGTAAAAACATCCGGCCCTCAGGGATCCCAGACCGATTCTCTGGCTCCAGCTCAGGA
AACTCAGCTTCCTTGACCATCACTGGGCTCAGGCGGAAGATGAGGCTGACTATTACTGTCACTCCCGGGACAGCAG
TGGTACCCATCTAAGGGTATTCGGCGGAGGGACCAAGGTCACCGTCCTAGGT*GCGGCCGC*AGAACAAAAACTCATCT
CAGAAGAGGATCTGAATGGGGCCGCATANACTGTTGAAAGTTGTTTANCAAANNCTCATACAGAAANTTNATTNNCT
ANNNTCTGGNAAGANGACAAAACTTTNNNTCGTNACGCTANNNNTNNNNNNTGTCTGTGANNGCNNCNGGCNNTGTG
NTNNNNACTGNNNNNNAAANTNNNGNTNNNNG (SEQ ID NO:10)

GCNNNTCTATTTAAGGAGACAGTCATAATGAAATACCTATTGCCTACGGCAGCCGCTGGATTGTTATTACTCGCGGC
CCAGCCGG*CCATGGC*CCAGGTGCAGCTGGTGGCGTCTGGAGGAGACTTGATCCAGCCTGGGGGGTCCCTGAGACTCT
CCTGTGCAGCCTCTGGATTCACCTTTAATAACTATTGGATGACCTGGGTCCGCCAGGCTCCAGGGAAGGGGCTGGAG
TGGGTGGCCAACATAAAGCAAGATGGAGGTGAGAAATACTATGTGGACTCTGTGAAGGGCCGATTCACCATCTCCAG
AGACAACGCCAAGACCTCACTGTATCTGCAAATGAACAGCCTGAGAGCCGAGGACACGGCCGTGTATTATTGTGCGA
AAGAGTCGTATAGCACTGGCTGGTTTGACCACTGGGGCCAGGGAACCCTGGTCACCGTCTCCTCAGGTGGAGGCGGT
TCAGGCGGAGGTGGCTCTGGCGGTGGCGGATCGAATTTTATGCTGACTCAGGACCCTGCTGTGTCTGTGGCCTTGGG
ACAGACAGTCAGGATAACATGTCAAGGTGACAGCCTCAGAAAATATTATACAAGTTGGTACCAACAGAAGCCAGGAC
AGGCCCCTCTACTTGTCATGTATGCGAAAAATAACCGGCCCTCAGGGATCCCAGACCGATTCTCTGGCTCCAGCTCA
GGAAACACAGCTTCCTTGACCATCACTGGGGCTCAGGCGGAAGATGAGGCTGACTATTACTGTGACTCCGGGACAG
CAGTGGTGACCATTGGGTGTTCGGCGGAGGGACCAAGCTGACCGTTCTAGGT*GCGGCCGC*AGAACAAAAACTCATCT
CAGAAGAGGATCTGAATGGGGCCGCATANACTGTTGAAAGTTGTTTANCAAAACCTCNTANNNAAAATTCATTTACT
AANGTCTGGAAAGACGACAAAACTTTANNTCGTTACGCTAACTATGNNGGCTGNCTGNNGNANGCTACNG (SEQ
ID NO:12)

>G12C

TNNNNTTNNNGAGACAGTCATAATGAAATACCTATTGCCTACGGCAGCCGCTGGATTGTTATTACTCGCGGCCCAGC
CGG*CCATGGC*CCGAGTGCAGCTGGTGGAGTCTGGGGCTGAGGTGACGAAGCCTGGGGCCTCAGTAAGGGTCTCCTGC
AAGGCTTCTGGATACACCTTCAGCAGATATGATATCAACTGGGTGCGACAGGCCTCTGGACAAGGGCTTGAGTGGAT
GGGATGGATCAACCCTAACAGTGGTAACACAGGCTATGCACAGAAGTTCCAGGGCAGAGTCACCATGACCAGGAATA
TTTCCATAACCACGGCCTACATGGAGCTGAGCAGCCTGAGATCTGAGGACACGGCCGTATATTACTGTGCGAGAGGC
CTTCCGGAGTTCGACCCCTGGGGCCAGGGAACCCTGGTCACCGTCTCCTCAGGTGGAGGCGGTTCAGGCGGAGGTGG
CTCTGGCGGTGGCGGATCGCACGTTATACTGACTCAGGACCCTGCTGTGTCTGTGGCCTTGGGACAGACAGTCAGGA
TCACATGCCAAGGAGACAGCCTCAGAAGCTATTATGCAAGCTGGTACCAGCAGAAGCCAGGACAGGCCCCTGTACTTT
GTCATCTATGGTAAAAACAACCGGCCCTCAGGGATCCCAGACCGATTCTCTGGCTCCAGCTCAGGAAACACAGCTTTC
CTTGACCATCACTGGGGCTCAGGCGGAAGATGAGGCTGACTTTTACTGTAATTCCCGGGACAGCAGTGGCACCCATC
TAGAGGTGTTCGGCGGAGGGACCAAGGTCACCGTCCTAGGT*GCGGCCGC*AGAACAAAAACTCATCTCAGAAGAGGAT
CTGAATGGGGCCGCATANACTGNTGAAAGTTGTTTANCAAAACCTCNTACAGAAAATTCATTTACTAACGTCTGGAA
AGACGANAAAACTTTANATCGTTACNCTAACTATNNNGGNTGTCTGNGNANTGNTAC (SEQ ID NO:14)

>H2

GCNNNTCTATTTNNNGAGACAGTCATAATGAAATACCTATTGCCTACGGCAGCCGCTGGATTGTTATTACTCGCGGC
CCAGCCGG*CCATGGC*CCAGGTGCAGCTGTGGAGTCTGGGGGAGGCGTGGTCCAGCCTGGGAGGTCCCTGAGACTCTC
CTGTGCAGCCTCTGGATTCACCTTCAGTAACTTTGGCATGCACTGGGTCTGCCAGGCTCCAGGCAAGGGGCTGGAGT
GGGTGGCAATTATTTCATATGATGCAAGTAGTGAATACTATGCAGACTCCGTGAAGGGCCGATTCACCATCTCCAGA
GACAATTCCAGGAACACTCTTTATCTGCAAATGAACAGCCTGAGACCTGAGGACACGGCTGTATATTACTGTGCGAA
GAAGGACGGTCGGAGTGGGAGCTACTACTACTTTGACTACTGGGGCCAGGGAACCCTGGTCACCGTCTCCTCAGGTG
GAGGCGGTTCAGGCGGAGGTGGCTCTGGCGGTGGCGGATCGGATGTTGTGATGACTCAGTCTCCATCCTCCCTGTCT
GCATCTGTAGGAGACAGAGTCACCATCACTTGCCGGGCGAGTCAAGATTTTAGGAATTGGTTAGCCTGGTATCAGGT
GAAACCAGGAAAAGCCCCCAAGCCCCTGATCTATGGTGCATCCACTTTGCAAAATGGGGTCCCATCCAGGTTCAGCG
GCAGTGGGTCTGANACAGATTTCTCTCTCACTATCAGCAGCCTGCAGCCTGAGNANTTTGCAACTTACTTTTGTCAA
CNGGNTCACAGTTTCCCTCCCACTTTCGNNGGAGGGANACGACTGGAGATTAAACGTGCNGCCGCNNACAAAACTCA
TCTCNNANNNNTCTGAATGGGGCCNCATANACTGNTGAAAGTNNTTANCAAACNNCNTACNNAAAATTCATTNCTAC
GTCNGGAANANNANNAANTTTANATNGTNCNCNANTATGNNGNNGNCNNNNNA (SEQ ID NO:21)

FIGURE 5A continued

>H2A
ANTTCTATTTNNNGAGACAGTCATAATGAAATACCTATTGCCTACGGCAGCCGCTGGATTGTTATTACTCGCGGCCC
AGCCGGCCATGGCCCAGGTACAGCTGCAGGAGTCTGGGGGAGGCTTGGTCCAGCCTGGGAGGTCCCTGAGACTCTCC
TGTGCAGCCTCTGGATTCACCTTCAGTAACTTTGGCATGCACTGGGTCTGCCAGGCTCCAGGCAAGGGGCTGGAGTG
GGTGGCAATTATTTCATATGATGCAAGTAGTGAATACTATGCAGACTCCGTGAAGGGCCGATTCACCATCTCCAGAG
ACAATTCCAGGAACACTCTTTATCTGCAAATGAACAGCCTGAGACCTGAGGACACGGCTGTATATTACTGTGCAAG
AAGGACGGTCGGAGTGGGAGCTACTACTACTTTGACTACTGGGGCCAGGGAACCCTGGTCACCGTCTCCTCAGGTGG
AGGCGGTTCAGGCGGAGGTGGCTCTGGCGGTGGCGGATCGGATGTTGTGATGACTCAGTCTCCATCCTCCCTGTCTG
CATCTGTAGGAGACAGAGTCACCATCACTTGCCGGCGAGTCAAGATTTTAGGAATTGGTTAGCCTGGTATCAGGTG
AAACCAGGAAAAGCCCCCAAGCCCCTGATCTATGGTGCATCCACTTTGCAAAATGGGGTCCCATCCAGGTTCAGCGG
CAGTGGGTCTGANACAGATTTCTCTCTCACTATCAGCAGCCTGCAGCCTGAGNANTTTGCAACTTACTTTTGTCAAC
NNNTCACAGTTTCCCTCCCACTTTCNCGGAGGNACACGACTGGANATCAAACGT*GCGGCCGC*NCATCATCATCACCA
TCANGGGNCNCNNANAAAACTCATCTCNAANAGGANCTGAATGGGCCGCATANACTGTGAAGTTGNTTANCAAACTC
NTANNNNANTNNTTTACTANGNCNGNNNANNANNAACTTAANTCNTNCNCTANNNNGANGNNNNCNNNGNANGNNAN
NNNNNNNNNNGNTNNNACNGNNNNNNNANNNNNNGNTACNG (SEQ ID NO:16)

>H7T
GNNNNTCNATTTNNNGAGACAGTCATAATGAAATACCTATTGCCTACGGCAGCCGCTGGATTGTTATTACTCGCGGC
CCAGCCGGCCATGGCCCAGGTGCAGCTGCAGGAGTCTGGGGGAGACGTGGTCCAGCCTGGGAGGTCCCTGAGACTCT
CCTGTGCAGCCTCTGGATTCACCTTCAGTAGCTATGGCATGCACTGGGTCCGCCAGGCTCCAGGCAAGGGGCTGGAG
TGGGTGGCAGTTATATCATATGATGAAAGTAATAAATACTATGCAGACTCCGTGAAGGGCCGATTCACCATCTCCAG
AGACAATTCCAAGAACACACTGTTTCTGCAAATGAACAGCCTGAGAGCTGAGGACACGGCTGTGTATTACTGTGCGA
AAGGACCTGTCCTAACCTGGGGAGTTTGACTATTGGGGCCGTAGAACCCTGGTCACCGTCTCCTCAGGTGGAGGCGGT
TCAGGCGGAGGTGGCTCTGGCGGTGGCGGATCGTCTGAGCTGACTCAGGACCCTGCTGTGTCTGTGGCCTTGGGACA
GACAGTCAGGATCACATGCCAAGGAGACAGCCTCAAAAGCTACTATGCAAGTTGGTACCAGCAGAAGCCAGGACAGG
CCCCTGTACTTGTCATCTATGGTGAAAACAGCCGGCCCTCCGGGATCCCAGACCGATTCTCTGGTTCCAGCTCANGA
AACACAGCTTCCTTGACCATCACTGGGGGCTCANGCGGAAGATGAAGCTGACTATTATTGTAACTCCCGGGACAACA
GTGGTACCCATCTTGAGGTATTGGCGGAGGGACCAAGCTGACCGTCCTAGGT*GCGGCCGC*AGAACAAAAACTCATC
TCAGAAGAGGATCTGAATGGGCCGCATANACTGTTGAAAGTTGTTTANCNAAACCTCATACNNAAAATTCATTTAC
TAACGTCTGGNAANACNACAAACTTTANATCGTTACGCTAACTATGAGGGCTGTCNGNGNAATGC (SEQ ID NO:18)

FIGURE 5B

```
C6T  (SEQ ID NO:20) ---------------gagacagtcataatgaaatacctattgcctacggcagccgctgga
H2   (SEQ ID NO:21) gcnnntctatttnnngagacagtcataatgaaatacctattgcctacggcagccgctgga
H2A  (SEQ ID NO:16) --anttctatttnnngagacagtcataatgaaatacctattgcctacggcagccgctgga
F9   (SEQ ID NO:8)  --aattctatttcngagacagtcataatgaaatacctattgcctacggcagccgctgga
H7   (SEQ ID NO:18) gnnnntcnatttnnngagacagtcataatgaaatacctattgcctacggcagccgctgga
D4   (SEQ ID NO:12) gcnnntctatttaaggagacagtcataatgaaatacctattgcctacggcagccgctgga
D11  (SEQ ID NO:10) gcanttcnatttnnngagacagtcataatgaaatacctattgcctacggcagccgctgga
G12  (SEQ ID NO:14) -----tnnnnttnnngagacagtcataatgaaatacctattgcctacggcagccgctgga
                                  ********************************************

C6T    ttgttattactcgcggcccagccggccatggcccaggtacagctgcaggagtctggggga
H2     ttgttattactcgcggcccagccggccatggcccaggtgcagctgtggagtctggggga
H2A    ttgttattactcgcggcccagccggccatggcccaggtacagctgcaggagtctggggga
F9     ttgttattactcgcggcccagccggccatggcccaggtgcagctgcaggagtcggggga
H7     ttgttattactcgcggcccagccggccatggcccaggtgcagctgcaggagtcggggga
D4     ttgttattactcgcggcccagccggccatggcccaggtgcagctggtgcgtctggagga
D11    ttgttattactcgcggcccagccggccatggccaggtgcagctggtggagtctggggga
G12    ttgttattactcgcggcccagccggccatggccgagtgcagctggtggagtctgggct
       ****************************** **..**.******   *.*** **.* :

C6T    ggcttggtacagcctggggggtccctgagactctcctgtgcagcctctggattcaccttt
H2     ggcgtggtccagcctggggaggtccctgagactctcctgtgcagcctctggattcaccttc
H2A    ggcttggtccagcctggggaggtccctgagactctcctgtgcagcctctggattcaccttc
F9     ggcgtggtccagcctggggaggtccctgagactctcctgtgcagcgtctggattcaccttc
H7     gacgtggtccagcctggggaggtccctgagactctcctgtgcagcctctggattcaccttc
D4     gacttgatccagcctgggggtccctgagactctcctgtgcagcctctggattcaccttt
D11    ggcttggtacagcctgggggtccctgagactctcctgtgcagcctctggattcaccttt
G12    gaggtgacgaagcctggggcctcagtaagggtctcctgcaaggcttctggatacaccttc
       *. **. .*******. **.*.**. ******  ...** *******:******

C6T    agcagctatgccatgagctgggtccgccaggctccagggaaggggctggagtgggtctca
H2     agtaactttggcatgcactgggtctgccaggctccaggcaaggggctggagtgggtggca
H2A    agtaactttggcatgcactgggtctgccaggctccaggcaaggggctggagtgggtggca
F9     agtacttctggcatgcactgggtccgccaggctccaggcaaggggctggagtgggtggca
H7     agtagctatggcatgcactgggtccgccaggctccaggcaaggggctggagtgggtggca
D4     aataactattggatgacctgggtccgccaggctccagggaaggggctggagtgggtggcc
D11    agcagctatgccatgagctgggtccgccaggctccagggaaggggctggagtgggtctca
G12    agcagatatgatatcaactgggtgcgacaggcctctggacaagggcttgagtggatggga
       *. * * ** . ***** *.***** *.** .* ***** ****** *

C6T    gctattagtggtagtggtggtagcacatactacgcagactccgtgaagggccgattcacc
H2     attatttcatatgatgcaagtagtgaatactatgcagactccgtgaagggccgattcacc
H2A    attatttcatatgatgcaagtagtgaatactatgcagactccgtgaagggccgattcacc
F9     tttatactacatgatggaagtgataaatactatgcagactccgtgaagggccgattcacc
H7     gttatatcatatgatgaaagtaataaatactatgcagactccgtgaagggccgattcacc
D4     aacataaagcaagatggaggtgagaaatactatgtggactctgtgaagggccgattcacc
D11    gctattagtggtagtggtggtagcacatactacgcagactccgtgaagggccggttcacc
G12    tggatcaaccctaacagtggtaacacaggctatgcacagaagttccagggcagagtcacc
       **     :... . :.**.. ...* .*** * . * :.  * .*****.*. *****
```

FIGURE 5B continued

```
C6T  atctccagagacaattccaagaacacgctgtatctgcaaatgaacagcctgagagctgag
H2   atctccagagacaattccaggaacactctttatctgcaaatgaacagcctgagacctgag
H2A  atctccagagacaattccaggaacactctttatctgcaaatgaacagcctgagacctgag
F9   atctccagagacaattccaagaacacgctgtatctgcaaatgaacagcctgagagccgag
H7   atctccagagacaattccaagaacacactgtttctgcaaatgaacagcctgagagctgag
D4   atctccagagacaacgccaagacctcactgtatctgcaaatgaacagcctgagagccgag
D11  atctccagagacaattccaagaacacgctgtatctgcaaatgaacagcctgagagccgag
G12  atgaccaggaatatttccataaccacggcctacatggagctgagcagcctgagatctgag
     **  ****   *  *    ***  *  * *      *   ** *  *** ********* *  ***

C6T  gacacggctgtgtattactgtgcgaagagctatggttcagttaaaa---taagctgcttt
H2   gacacggctgtatattactgtgcgaagaaggacggtcggagtgggagctactactactttt
H2A  gacacggctgtatattactgtgcgaagaaggacggtcggagtgggagctactactacttt
F9   gacacggccatatattactgtgcgaaatctcagagggagctactcggcgctgaatacctc
H7   gacacggctgtgtattactgtgcgaaa----------ggacctgtcctaactggggagttt
D4   gacacggccgtgtattattgtgcgaaa----------gagtcgtatagcactggctggttt
D11  gacacggctgtatattactgtgcaaga----------gg---tggcgattatggctcaggg
G12  gacacggccgtatattactgtgcgaga-------------------ggccttccggagttc
     ********  *  ***** ***** *

C6T  gactactggggccagagcaccctggtcaccgtctcctcaggtggaggcggttcaggcgga
H2   gactactggggccagggaaccctggtcaccgtctcctcaggtggaggcggttcaggcgga
H2A  gactactggggccagggaaccctggtcaccgtctcctcaggtggaggcggttcaggcgga
F9   cagaactggggccagggcaccctggtcaccgtctcctcaggtggaggcggttcaggcgga
H7   gactattggggccgtagaaccctggtcaccgtctcctcaggtggaggcggttcaggcgga
D4   gaccactggggccagggaaccctggtcaccgtctcctcaggtggaggcggttcaggcgga
D11  gactactggggccagggaaccctggtcaccgtctcctcaggtggaggcggttcaggcgga
G12  gaccactggggccagggaaccctggtcaccgtctcctcaggtggaggcggttcaggcgga
      *   *******   *  *********************************

C6T  ggtggctctggcggtggcggatcggaaattgtgctgacgcagtctccagactccctggct
H2   ggtggctctggcggtggcggatcggatgttgtgatgactcagtctccatcctccctgtct
H2A  ggtggctctggcggtggcggatcggatgttgtgatgactcagtctccatcctccctgtct
F9   ggtggctctggcggtggcggatcgcagtctgctctgactcagcctgc---ctccgtgtct
H7   ggtggctctggcggtggcggatcg---tctgagctgactcaggaccc---tgctgtgtct
D4   ggtggctctggcggtggcggatcgaattttatgctgactcaggaccc---tgctgtgtct
D11  ggtggctctggcggtggcggatcgaattttatgctgactcaggaccc---tgctgtgtct
G12  ggtggctctggcggtggcggatcgcacgttatactgactcaggaccc---tgctgtgtct
     *********************   *  **** ***    *    *  ** **

C6T  gtgtctctgggcgagagggccaccatcaactgcaagtccagccagagtgttctttacaac
H2   gcatctgtaggagacagagtcaccatcacttgccgggcgagtca----------------
H2A  gcatctgtaggagacagagtcaccatcacttgccgggcgagtca----------------
F9   gggtctcctggacagtcgatcaccatctcctgcactggaaccagcagtg---------ac
H7   gtggccttgggacagacagtcaggatcacatgccaaggagacag----------------
D4   gtggccttgggacagacagtcaggataacatgtcaaggtgacag----------------
D11  gtggccttgggacagacagtcagaatcacatgccaaggagacag----------------
G12  gtggccttgggacagacagtcaggatcacatgccaaggagacag----------------
     *   *   **   *    ** ** **   **

C6T  tccaacaataagaactacttagcttggtaccagcagaaaccaggacagtctcctgagttg
H2   --agattttaggaattggttagcctggtatcaggtgaaaccaggaaaagcccccaagccc
H2A  --agattttaggaattggttagcctggtatcaggtgaaaccaggaaaagcccccaagccc
```

FIGURE 5B continued

```
F9     gttggtggttataagtatgtctcctggtaccaacagcacccaggcaaagcccccaaagtc
H7     --cctcaaaaagctactatgcaagttggtaccagcagaagccaggacaggcccctgtactt
D4     --cctcagaaaatattatacaagttggtaccaacagaagccaggacaggcccctctactt
D11    --cctcagaagctattatgcaagttggtaccagcagaagccaggacaggcccctctcctt
G12    --cctcagaagctattatgcaagctggtaccagcagaagccaggacaggcccctgtactt
            ::. :* *.   .     ***** **. :*.* *****..*. * **  :

C6T    ctcatttactgggcatcaacccggaatccggggtccctgaccgattcagtggcagcggg
H2     ctgatctatggtgcatccactttgcaaaatggggtcccatccaggttcagcggcagtggg
H2A    ctgatctatggtgcatccactttgcaaaatggggtcccatccaggttcagcggcagtggg
F9     atgatttatgatgtcagtaatcggccctcaggggtttctaatcgcttctctggctccaag
H7     gtcatctatggtgaaaacagccggccctccgggatcccagaccgattctctggttccagc
D4     gtcatgtatgcgaaaaataaccggccctcagggatcccagaccgattctctggctccagc
D11    gtcatctatggtaaaaacatccggccctcagggatcccagaccgattctctggctccagc
G12    gtcatctatggtaaaaacaaccggccctcagggatcccagaccgattctctggctccagc
         * ** **       ..: *    * ...:. ***.*  *:  . .* ***: ** :  ..

C6T    tctgggacagaattcactcttaccatcagc-agcctgcaggctgaggatgtggcagttta
H2     tctgañacagatttctctctcactatcagc-agcctgcagcctgagnantttgcaactta
H2A    tctganacagatttctctctcactatcagc-agcctgcagcctgagnantttgcaactta
F9     tctggcaacacggcctccctgaccatctct-gggctccaggctgaggacgaggctgatta
H7     tcañgaaacacagcttccttgaccatcactgggggctcañgcggaagatgaagctgacta
D4     tcaggaaacacagcttccttgaccatcact-ggggctcaggcggaagatgaggctgacta
D11    tcaggaaactcagcttccttgaccatcact-ggggctcaggcggaagatgaggctgacta
G12    tcaggaaacacagcttccttgaccatcact-ggggctcaggcggaagatgaggctgactt
       **:.. *.. .      :*  * ** ***:   ,*    **. * **..*  : **:.  *:

C6T    ttactgtca---gcaattttatagtactcctccg------acttttggccaggggaccaa
H2     cttttgtca---acnggntcacagtttccctccc------actttcgnnggagggganacg
H2A    cttttgtca---ac-ñnntcacagtttccctccc------actttc-ncggagggnacacg
F9     ttactgcagctcatatacaagcagcagcactctc------gtgttcggcggcgggaccaa
H7     ttattgtaactcccgggacaacagtggtacccatcttgaggtattcggcggagggaccaa
D4     ttactgtgactcccgggacagcagtggtgaccatt---gggtgttcggcggaggggaccaa
D11    ttactgtcactcccgggacagcagtggtacccatctaagggtattcggcggagggaccaa
G12    ttactgtaattcccgggacagcagtggcacccatctagaggtgttcggcggagggaccaa
       *: **   .         ,**    .*       , **   , **.*  ...

C6T    gctggagatcaaacgtgcggccgcacatcatcatcaccatcacggggccgcagaacaaaa
H2     actggagattaaacgtgcggccg------------------------------cnnacaaa
H2A    actgganatcaaacgtgcggccgcncatcatcatcaccatcangggn---cncnnanaaa
F9     ggtcaccgtcctaggtgcggccg------------------------------cagaacaaaa
H7     gctgaccgtcctaggtgcggccg------------------------------cagaacaaaa
D4     gctgaccgttctaggtgcggccg------------------------------cagaacaaaa
D11    ggtcaccgtcctaggtgcggccg------------------------------cagaacaaaa
G12    ggtcaccgtcctaggtgcggccg------------------------------cagaacaaaa
       . *  .. .* .:* ****.****                                  . ***

C6T    actcatctcagaagaggatc----------------------------------------
H2     actcatctcnña--nññntctgaatgggggccncatanactgntgaaagtnntt--ancaa
H2A    actcatctcnaa--nagganctgaatggggccgcatanactg-tgaagttgntt--ancaa
F9     actcatctcagaagaggatctgaatggggccgcatanactgttgaaagtntttanc-aa
H7     actcatctcagaagaggatctgaatggggccgcatanactgttgaaagttgtttancnaa
D4     actcatctcagaagaggatctgaatggggccgcatanactgttgaaagttgtttancaaa
```

FIGURE 5B continued

```
D11        actcatctcagaagaggatctgaatggggccgcatanactgttgaaagttgtttancaaa
G12        actcatctcagaagaggatctgaatggggccgcatanactgntgaaagttgtttancaaa
           ********  *       .  :

C6T        ------------------------------------------------------------
H2         acnncntacnnaaaattcatt----nctacgtcnggaanannannaantttanatngtnc
H2A        actcnt--annnnantnnttt----actangncng--nnnannannaacttaantcntnc
F9         nnntcatacnnaaaattcatttactaacgtctggnaanacnacaaaactttnnatcgtta
H7         acctcatacnnaaaattcatttactaacgtctggnaanacnac-aaactttanatcgtta
D4         acctcntannnaaaattcatttactaangtctggaaagacgacaaaactttanntcgtta
D11        nnctcatacagaaantttattnnctannntctggnaagangacaaaactttnnntcgtna
G12        acctcntacagaaaattcatttactaacgtctggaaagacganaaaactttanatcgtta C6T        ------------------------------------------------------------
H2         ncnantatgnngnngncnnnnna-------------------------------------
H2A        nctannnngangnnnncnnngnangnnannnnnnnnnnngntnnnacngnnnnnnannnn
F9         ngctaantnnnnnagggcngt---------------------------------------
H7         cgctaactatgagggctgtcngngnaatgc------------------------------
D4         cgctaactatgnnggctgnctgnngnangctacng-------------------------
D11        cgctannnntnnnnnntgtctgtgannngcnncnggcnntgtgntnnnnactgnnnnnnaa
G12        cnctaactatnnnggntgtctgngnantgntac---------------------------

C6T        --------------
H2         --------------
H2A        nngntacng-----
F9         --------------
H7         --------------
D4         --------------
D11        antnnngntnnnng
G12        --------------
```

FIGURE 12

```
Sfil       GGCCCAGCCGGCC
NcoI                     CCATGG
Met
start                         ATG        HCFR1
αphOx15    GGCCCAGCCGG   CC  ATG  G  CC  CAGGTGCAGCTGGTGCAGTCTGGGGCTGAGGTGAAG
αBSA3      GGCCCAGCCGG   CC  ATG  G  CC  CAGGTGCAGCTGGTGCAGTCTGGGGGAGGCGTGGTC
αTEL9      GGCCCAGCCGG   CC  ATG  G  CC  CAGGTACAGCTGCAGCAGTCAGGCTCAGGACTGGTG
αTEL14     GGCCCAGCCGG   CC  ATG  G  CC  CAGGTGCAGCTGCAGGAGTCGGGGCCAGGACTGGTG
αTEL13     GGCCCAGCCGG   CC  ATG  G  CC  CAGGTGCAGCTGGTGCAGTCTGGAGCAGAGGTGAAA
αTEL16     GGCCCAGCCGG   CC  ATG  G  CC  CAGGTGCAGCTGGTGCAGTCTGGGGCAGAGGTGAAA
F9         GGCCCAGCCGG   CC  ATG  G  CC  CAGGTGCAGCTGCAGGAGTC GGGGGAGGCGTGGTC
D11        GGCCCAGCCGG   CC  ATG  G   C  CAGGTGCAGCTGGTGGAGTCTGGGGGAGGCTTGGTA
H2         GGCCCAGCCGG   CC  ATG  G  CC  CAGGTGCAGCTG TGGAGTCTGGGGGAGGCGTGGTC
D4         GGCCCAGCCGG   CC  ATG  G  CC  CAGGTGCAGCTGGTGC GTCTGGAGGAGACTTGATC
H7         GGCCCAGCCGG   CC  ATG  G  CC  CAGGTGCAGCTGCAGGAGTC GGGGGAGACGTGGTC
G12        GGCCCAGCCGG   CC  ATG  G   C  CGAGTGCAGCTGGTGGAGTCTGGGGCTGAGGTGACG HCFR1(Cont'd)
αphOx15    AAGCCTGGGGCCTCAGTGAAGGTCTCCTGCAAGGCTTCTGGTTACACCTTTACC
αBSA3      CAGCCTGGGAGGTCCCTGAGACTCTCCTGTGCAGCCTCTGGATTCACCTTCAGT
αTEL9      AAGCCTTCACAGACCCTGTCCCTCACCTGCTCTGTCTCTGGTGACTCCATCTCC
αTEL14     AAGCCTTCGGAGACCCTGTCCCTCGTCTGCACTGTCTCTGGTGGCTCCCTCAGT
αTEL13     AAGCCCGGGCAGTCTCTGATGATCTCCTGTCAGGGTTCTGGATACAGCTTTAGC
αTEL16     AAGCCCGGGCAGTCTCTGAGGATCTCCTGTAAGGGTGCTGGATACAGCTTTAGC
F9         CAGCCTGGGAGGTCCCTGAGACTCTCCTGTGCAGCGTCTGGATTCACCTTCAGT
D11        CAGCCTGGGGGGTCCCTGAGACTCTCCTGTGCAGCCTCTGGATTCACCTTTAGC
H2         CAGCCTGGGAGGTCCCTGAGACTCTCCTGTGCAGCCTCTGGATTCACCTTCAGT
D4         CAGCCTGGGGGGTCCCTGAGACTCTCCTGTGCAGCCTCTGGATTCACCTTTAAT
H7         CAGCCTGGGAGGTCCCTGAGACTCTCCTGTGCAGCCTCTGGATTCACCTTCAGT
G12        AAGCCTGGGGCCTCAGTAAGGGTCTCCTGCAAGGCTTCTGGATACACCTTCAGC
```

FIGURE 13

| PRIMER NAMES | DNA SEQUENCES |
|---|---|
| F9T FORWARD PRIMER | 5'-ATA TAT CCA TGG CCC AGG TGC AGC TGC AGG AGT CTG GGG GAG GCG TGG TCC-3' |
| D11C FORWARD PRIMER | 5'-ATA TAT CCA TGG CCC AGG TGC AGC TGG TGG AGT CTG GGG GAG GCT TGG TAC-3' |
| H2A FORWARD PRIMER | 5'-GCC GGC CAT GGC CCA GGT ACA GCT GC A GGA GTC TGG GGG AGG CTT GGT-3' |
| REVERSE PRIMER FOR ALL THREE CLONES | 5'-CCC GTG ATG GTG ATG ATG ATG TGC GGC CGC ACG TTT GAT CTC CAG -3' |

☑ Tau 1N4R SPLICE VARIANT (LEFT)
◩ Tau 2N4R SPLICE VARIANT (RIGHT)

Tau FINAL CONCENTRATION IS
15.50 nM. THE INCUBATION TIME IS 48 HOURS

☑ Tau 1N4R SPLICE VARIANT (LEFT)
◩ Tau 2N4R SPLICE VARIANT (RIGHT)

TAU FINAL CONCENTRATION IS
15.50 nM. THE INCUBATION TIME IS 48 HOURS

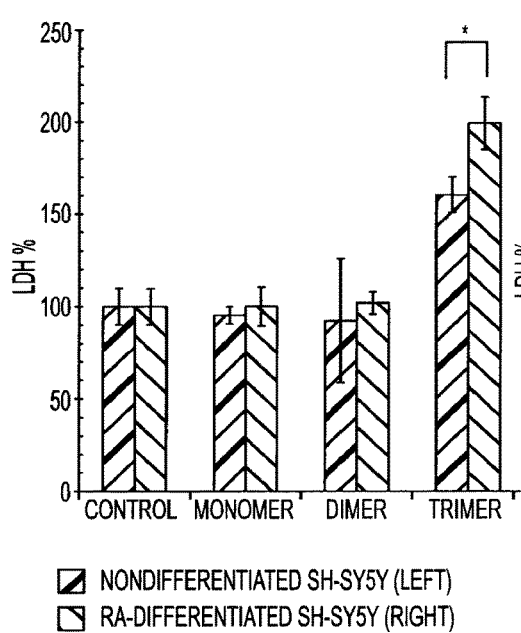
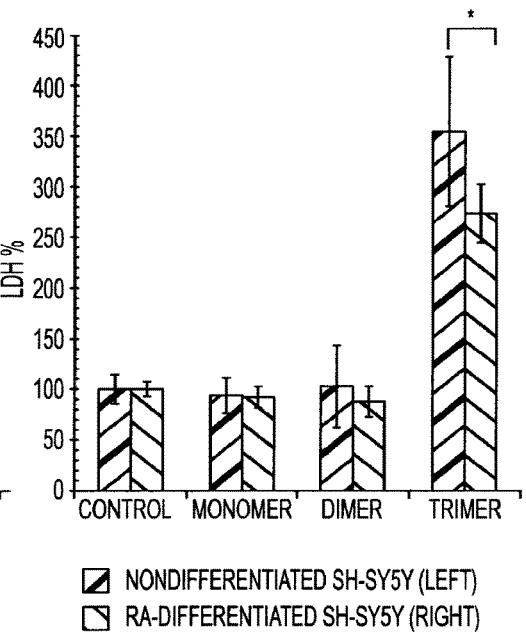
FIGURE 19A
FIGURE 19B
☒ NONDIFFERENTIATED SH-SY5Y (LEFT)
☒ RA-DIFFERENTIATED SH-SY5Y (RIGHT)
Tau FINAL CONCENTRATION IS
15.50 nM. AND THE INCUBATION TIME IS 3 HOURS
☒ NONDIFFERENTIATED SH-SY5Y (LEFT)
☒ RA-DIFFERENTIATED SH-SY5Y (RIGHT)
Tau FINAL CONCENTRATION IS
15.50 nM. AND THE INCUBATION TIME
IS 48 HOURS

SEQUENCE LISTING

```
<160> NUMBER OF SEQ ID NOS: 50

<210> SEQ ID NO 1
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (297)..(300)
<223> OTHER INFORMATION: Any amino acid

<400> SEQUENCE: 1

Xaa Glu Xaa Val Ile Met Lys Tyr Leu Leu Pro Thr Ala Ala Ala Gly
1               5                   10                  15

Leu Leu Leu Leu Ala Ala Gln Pro Ala Met Ala Gln Val Gln Leu Gln
            20                  25                  30

Glu Ser Gly Gly Gly Val Val Gln Pro Gly Arg Ser Leu Arg Leu Ser
        35                  40                  45

Cys Ala Ala Ser Gly Phe Thr Phe Ser Thr Ser Gly Met His Trp Val
    50                  55                  60

Arg Gln Ala Pro Gly Lys Gly Leu Glu Trp Val Ala Phe Ile Leu His
65                  70                  75                  80

Asp Gly Ser Asp Lys Tyr Tyr Ala Asp Ser Val Lys Gly Arg Phe Thr
                85                  90                  95

Ile Ser Arg Asp Asn Ser Lys Asn Thr Leu Tyr Leu Gln Met Asn Ser
            100                 105                 110

Leu Arg Ala Glu Asp Thr Ala Ile Tyr Tyr Cys Ala Lys Ser Gln Arg
        115                 120                 125

Glu Leu Leu Gly Ala Glu Tyr Leu Gln Asn Trp Gly Gln Gly Thr Leu
    130                 135                 140

Val Thr Val Ser Ser Gly Gly Gly Ser Gly Gly Gly Gly Ser Gly
145                 150                 155                 160

Gly Gly Gly Ser Gln Ser Ala Leu Thr Gln Pro Ala Ser Val Ser Gly
                165                 170                 175

Ser Pro Gly Gln Ser Ile Thr Ile Ser Cys Thr Gly Thr Ser Ser Asp
            180                 185                 190

Val Gly Gly Tyr Lys Tyr Val Ser Trp Tyr Gln Gln His Pro Gly Lys
        195                 200                 205

Ala Pro Lys Val Met Ile Tyr Asp Val Ser Asn Arg Pro Ser Gly Val
    210                 215                 220
```

Ser Asn Arg Phe Ser Gly Ser Lys Ser Gly Asn Thr Ala Ser Leu Thr
225                 230                 235                 240

Ile Ser Gly Leu Gln Ala Glu Asp Glu Ala Asp Tyr Tyr Cys Ser Ser
                245                 250                 255

Tyr Thr Ser Ser Ser Thr Leu Val Phe Gly Gly Gly Thr Lys Val Thr
            260                 265                 270

Val Leu Gly Ala Ala Ala His His His His His Gly Ala Ala Glu
        275                 280                 285

Gln Lys Leu Ile Ser Glu Glu Asp Xaa Xaa Xaa Xaa
        290                 295                 300

<210> SEQ ID NO 2
<211> LENGTH: 991
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (902)..(902)
<223> OTHER INFORMATION: a, c, t, g, unknown or other
<220> FEATURE:
<221> NAME/KEY: modified_base
<222> LOCATION: (907)..(907)
<223> OTHER INFORMATION: a, c, t, g, unknown or other
<220> FEATURE:
<221> NAME/KEY: modified_base
<222> LOCATION: (911)..(913)
<223> OTHER INFORMATION: a, c, t, g, unknown or other
<220> FEATURE:
<221> NAME/KEY: modified_base
<222> LOCATION: (920)..(921)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (951)..(951)
<223> OTHER INFORMATION: a, c, t, g, unknown or other
<220> FEATURE:
<221> NAME/KEY: modified_base
<222> LOCATION: (962)..(963)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (977)..(977)
<223> OTHER INFORMATION: a, c, t, g, unknown or other
<220> FEATURE:
<221> NAME/KEY: modified_base
<222> LOCATION: (979)..(983)
<223> OTHER INFORMATION: a, c, t, g, unknown or other
<220> FEATURE:
<221> NAME/KEY: modified_base
<222> LOCATION: (989)..(989)
<223> OTHER INFORMATION: a, c, t, g, unknown or other

<400> SEQUENCE: 2

```
aattctattt cnggagacag tcataatgaa atacctattg cctacggcag ccgctggatt        60
gttattactc gcggcccagc cggccatggc ccaggtgcag ctgcaggagt cgggggaggc       120
gtggtccagc ctgggaggtc cctgagactc tcctgtgcag cgtctggatt caccttcagt       180
acttctggca tgcactgggt ccgccaggct ccaggcaagg ggctggagtg gtggcattt        240 atactacatg atgaagtga taaatactat gcagactccg tgaagggccg attcaccatc        300
tccagagaca attccaagaa cacgctgtat ctgcaaatga acagcctgag agccgaggac       360
acggccatat attactgtgc gaaatctcag agggagctac tcggcgctga atacctccag       420
aactggggcc agggcaccct ggtcaccgtc tcctcaggtg gaggcggttc aggcggaggt       480
ggctctggcg gtggcggatc gcagtctgct ctgactcagc ctgcctccgt gtctgggtct       540
cctggacagt cgatcaccat ctcctgcact ggaaccagca gtgacgttgg tggttataag       600
tatgtctcct ggtaccaaca gcacccaggc aaagcccca aagtcatgat ttatgatgtc        660
agtaatcggc cctcagggt tctaatcgc ttctctggct ccaagtctgg caacacggcc         720
tccctgacca tctctgggct ccaggctgag gacgaggctg attattactg cagctcatat       780
acaagcagca gcactctcgt gttcggcggc gggaccaagg tcaccgtcct aggtgcggcc       840
gcagaacaaa aactcatctc agaagaggat ctgaatgggg ccgcatanac tgttgaaagt       900
tntttancaa nnntcatacn naaaattcat ttactaacgt ctggnaanac nacaaaactt       960
tnnatcgtta ngctaantnn nnnagggcng t                                      991
```

<210> SEQ ID NO 3
<211> LENGTH: 902
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (892)..(893)
<223> OTHER INFORMATION: a, c, t, g, unknown or other
<220> FEATURE:
<221> NAME/KEY: modified_base
<222> LOCATION: (896)..(900)
<223> OTHER INFORMATION: a, c, t, g, unknown or other

<400> SEQUENCE: 3

```
ttcnngagan agtcataatg aaatacctat gcctacggc agccgctgga ttgttattac         60
tcgcggccca gccggccatg gcccaggtgc agctgcagga gtctggggga ggcgtggtcc       120
agcctgggag gtccctgaga ctctcctgtg cagcgtctgg attcaccttc agtacttctg       180
gcatgcactg ggtccgccag gctccaggca aggggctgga gtgggtggca tttatactac       240
atgatggaag tgataaatac tatgcagact ccgtgaaggg ccgattcacc atctccagag       300
acaattccaa gaacacgctg tatctgcaaa tgaacagcct gagagccgag gacacggcca       360
tatattactg tgcgaaatct cagagggagc tactcggcgc tgaatacctc cagaactggg       420 gccaggcac cctggtcacc gtctcctcag gtggaggcgg ttcaggcgga ggtggctctg       480
```

```
gcggtggcgg atcgcagtct gctctgactc agcctgcctc cgtgtctggg tctcctggac    540
agtcgatcac catctcctgc actggaacca gcagtgacgt tggtggttat aagtatgtct    600
cctggtacca acagcaccca ggcaaagccc ccaaagtcat gatttatgat gtcagtaatc    660
ggccctcagg ggtttctaat cgcttctctg gctccaagtc tggcaacacg gcctccctga    720
ccatctctgg gctccaggct gaggacgagg ctgattatta ctgcagctca tatacaagca    780
gcagcactct cgtgttcggc ggcgggacca aggtcaccgt cctaggtgcg gccgcacatc    840
atcatcacca tcacggggcc gcagaacaaa aactcatctc agaagaggat cnnaannnnn    900
cg                                                                    902

<210> SEQ ID NO 4
<211> LENGTH: 902
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (892)..(893)
<223> OTHER INFORMATION: a, c, t, g, unknown or other
<220> FEATURE:
<221> NAME/KEY: modified_base
<222> LOCATION: (896)..(900)
<223> OTHER INFORMATION: a, c, t, g, unknown or other

<400> SEQUENCE: 4
ttcnngagan agtcataatg aaatacctat tgcctacggc agccgctgga ttgttattac     60
tcgcggccca gccggccatg gcccaggtgc agctgcagga gtctggggga ggcgtggtcc    120
agcctgggag gtccctgaga ctctcctgtg cagcgtctgg attcaccttc agtacttctg    180
gcatgcactg ggtccgccag gctccaggca agggctgga gtgggtggca tttatactac     240
atgatggaag tgataaatac tatgcagact ccgtgaaggg ccgattcacc atctccagag    300
acaattccaa gaacacgctg tatctgcaaa tgaacagcct gagagccgag gacacggcca    360
tatattactg tgcgaaatct cagagggagc tactcggcgc tgaataccte cagaactggg    420 gccagggcac cctggtcacc gtctcctcag gtggaggcgg ttcaggcgga ggtggctctg    480
gcggtggcgg atcgcagtct gctctgactc agcctgcctc cgtgtctggg tctcctggac    540
agtcgatcac catctcctgc actggaacca gcagtgacgt tggtggttat aagtatgtct    600
cctggtacca acagcaccca ggcaaagccc ccaaagtcat gatttatgat gtcagtaatc    660
ggccctcagg ggtttctaat cgcttctctg gctccaagtc tggcaacacg gcctccctga    720
ccatctctgg gctccaggct gaggacgagg ctgattatta ctgcagctca tatacaagca    780
gcagcactct cgtgttcggc ggcgggacca aggtcaccgt cctaggtgcg gccgcacatc    840
atcatcacca tcacggggcc gcagaacaaa aactcatctc agaagaggat cnnaannnnn    900
cg                                                                    902

<210> SEQ ID NO 5
<211> LENGTH: 991
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (902)..(902)
<223> OTHER INFORMATION: a, c, t, g, unknown or other
<220> FEATURE:
<221> NAME/KEY: modified_base
<222> LOCATION: (907)..(907)
<223> OTHER INFORMATION: a, c, t, g, unknown or other
<220> FEATURE:
<221> NAME/KEY: modified_base
<222> LOCATION: (911)..(913)
<223> OTHER INFORMATION: a, c, t, g, unknown or other
<220> FEATURE:
<221> NAME/KEY: modified_base
<222> LOCATION: (920)..(921)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (951)..(951)
<223> OTHER INFORMATION: a, c, t, g, unknown or other
<220> FEATURE:
<221> NAME/KEY: modified_base
<222> LOCATION: (962)..(963)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (977)..(977)
<223> OTHER INFORMATION: a, c, t, g, unknown or other
<220> FEATURE:
<221> NAME/KEY: modified_base
<222> LOCATION: (979)..(983)
<223> OTHER INFORMATION: a, c, t, g, unknown or other
<220> FEATURE:
<221> NAME/KEY: modified_base
<222> LOCATION: (989)..(989)
<223> OTHER INFORMATION: a, c, t, g, unknown or other

<400> SEQUENCE: 5
aattctattt cnggagacag tcataatgaa atacctattg cctacggcag ccgctggatt      60
gttattactc gcggcccagc cggccatggc ccaggtgcag ctgcaggagt cgggggaggc     120
gtggtccagc ctgggaggtc cctgagactc tcctgtgcag cgtctggatt caccttcagt     180
acttctggca tgcactgggt ccgccaggct ccaggcaagg gctgagtg gtggcatttt       240 atactacatg atggaagtga taaatactat gcagactccg tgaagggccg attcaccatc     300
tccagagaca attccaagaa cacgctgtat ctgcaaatga acagcctgag agccgaggac     360
acggccatat attactgtgc gaaatctcag agggagctac tcggcgctga ataccctccag   420 aactggggcc agggcaccct ggtcaccgtc tcctcaggtg gaggcggttc aggcggaggt    480
```

```
ggctctggcg gtggcggatc gcagtctgct ctgactcagc ctgcctccgt gtctgggtct    540
cctggacagt cgatcaccat ctcctgcact ggaaccagca gtgacgttgg tggttataag    600
tatgtctcct ggtaccaaca gcacccaggc aaagccccca agtcatgat ttatgatgtc    660 agtaatcggc cctcagggt ttctaatcgc ttctctggct ccaagtctgg caacacggcc     720
tccctgacca tctctgggct ccaggctgag gacgaggctg attattactg cagctcatat    780
acaagcagca gcactctcgt gttcggcggc gggaccaagg tcaccgtcct aggtgcggcc    840
gcagaacaaa aactcatctc agaagaggat ctgaatgggg ccgcatanac tgttgaaagt    900
tntttancaa nnntcatacn naaaattcat ttactaacgt ctggnaanac nacaaaactt    960
tnnatcgtta ngctaantnn nnnagggcng t                                   991
```

<210> SEQ ID NO 6  
<211> LENGTH: 1002  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<221> NAME/KEY: modified_base  
<222> LOCATION: (4)..(5)  
<223> OTHER INFORMATION: a, c, t, g, unknown or other  
<220> FEATURE:  
<221> NAME/KEY: modified_base  
<222> LOCATION: (10)..(10)  
<223> OTHER INFORMATION: a, c, t, g, unknown or other  
<220> FEATURE:  
<221> NAME/KEY: modified_base  
<222> LOCATION: (743)..(743)  
<223> OTHER INFORMATION: a, c, t, g, unknown or other  
<220> FEATURE:  
<221> NAME/KEY: modified_base  
<222> LOCATION: (799)..(800)  
<223> OTHER INFORMATION: a, c, t, g, unknown or other  
<220> FEATURE:  
<221> NAME/KEY: modified_base  
<222> LOCATION: (824)..(826)  
<223> OTHER INFORMATION: a, c, t, g, unknown or other  
<220> FEATURE:  
<221> NAME/KEY: modified_base  
<222> LOCATION: (862)..(862)  
<223> OTHER INFORMATION: a, c, t, g, unknown or other  
<220> FEATURE:  
<221> NAME/KEY: modified_base  
<222> LOCATION: (878)..(879)  
<223> OTHER INFORMATION: a, c, t, g, unknown or other  
<220> FEATURE:  
<221> NAME/KEY: modified_base  
<222> LOCATION: (881)..(881)  
<223> OTHER INFORMATION: a, c, t, g, unknown or other  
<220> FEATURE:  
<221> NAME/KEY: modified_base  
<222> LOCATION: (900)..(900)  
<223> OTHER INFORMATION: a, c, t, g, unknown or other  
<220> FEATURE:  
<221> NAME/KEY: modified_base  
<222> LOCATION: (903)..(903)  
<223> OTHER INFORMATION: a, c, t, g, unknown or other  
<220> FEATURE:  
<221> NAME/KEY: modified_base  
<222> LOCATION: (908)..(908)  
<223> OTHER INFORMATION: a, c, t, g, unknown or other  
<220> FEATURE:  
<221> NAME/KEY: modified_base  
<222> LOCATION: (921)..(921)  
<223> OTHER INFORMATION: a, c, t, g, unknown or other  
<220> FEATURE:  
<221> NAME/KEY: modified_base  
<222> LOCATION: (931)..(931)  
<223> OTHER INFORMATION: a, c, t, g, unknown or other
<220> FEATURE:
<221> NAME/KEY: modified_base
<222> LOCATION: (935)..(936)
<223> OTHER INFORMATION: a, c, t, g, unknown or other
<220> FEATURE:
<221> NAME/KEY: modified_base
<222> LOCATION: (965)..(969)
<223> OTHER INFORMATION: a, c, t, g, unknown or other
<220> FEATURE:
<221> NAME/KEY: modified_base
<222> LOCATION: (977)..(977)
<223> OTHER INFORMATION: a, c, t, g, unknown or other
<220> FEATURE:
<221> NAME/KEY: modified_base
<222> LOCATION: (980)..(980)
<223> OTHER INFORMATION: a, c, t, g, unknown or other
<220> FEATURE:
<221> NAME/KEY: modified_base
<222> LOCATION: (985)..(988)
<223> OTHER INFORMATION: a, c, t, g, unknown or other
<220> FEATURE:
<221> NAME/KEY: modified_base
<222> LOCATION: (992)..(992)
<223> OTHER INFORMATION: a, c, t, g, unknown or other
<220> FEATURE:
<221> NAME/KEY: modified_base
<222> LOCATION: (996)..(1000)
<223> OTHER INFORMATION: a, c, t, g, unknown or other
<220> FEATURE:
<221> NAME/KEY: modified_base
<222> LOCATION: (1002)..(1002)
<223> OTHER INFORMATION: a, c, t, g, unknown or other

<400> SEQUENCE: 6

```
ttcnngagan agtcataatg aaatacctat tgcctacggc agccgctgga ttgttattac    60
tcgcggccca gccggccatg gcccaggtgc agctgcagga gtctggggga ggcgtggtcc   120
agcctgggag gtccctgaga ctctcctgtg cagcgtctgg attcaccttc agtacttctg   180
gcatgcactg ggtccgccag gctccaggca aggggctgga gtgggtggca tttatactac   240
atgatggaag tgataaatac tatgcagact ccgtgaaggg ccgattcacc atctccagag   300
acaattccaa gaacacgctg tatctgcaaa tgaacagcct gagagccgag gacacggcca   360
tatattactg tgcgaaatct cagagggagc tactcggcgc tgaataccto cagaactggg   420
gccagggcac cctggtcacc gtctcctcag gtggaggcgg ttcaggcgga ggtggctctg   480
gcggtggcgg atcgcagtct gctctgactc agcctgcctc cgtgtctggg tctcctggac   540
agtcgatcac catctcctgc actggaacca gcagtgacgt tggtggttat aagtatgtct   600
cctggtacca acagcaccca ggcaaagccc ccaaagtcat gatttatgat gtcagtaatc   660
ggccctcagg ggtttctaat cgcttctctg gctccaagtc tggcaacacg gcctccctga   720
ccatctctgg gctccaggct gangacgagg ctgattatta ctgcagctca tatacaagca   780
gcagcactct cgtgttcgnn ggcgggacca aggtcaccgt cctnnngcgg ccgcacatca   840
tcatcaccat cacggggccg cngacaaaac tcatctcnna naggatctga atgggccgcn   900
tanactgntg aaagttgtta ncaaaacctc ntacnnaaaa ttcatttact aacgtctgga   960
aagannnnna actttanatn gttannnnaa cnatgnnnnn gn                    1002
```

<210> SEQ ID NO 7
<211> LENGTH: 991
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base

```
<222> LOCATION: (2)..(6)
<223> OTHER INFORMATION: a, c, t, g, unknown or other
<220> FEATURE:
<221> NAME/KEY: modified_base
<222> LOCATION: (8)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (24)..(29)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (58)..(58)
<223> OTHER INFORMATION: a, c, t, g, unknown or other
<220> FEATURE:
<221> NAME/KEY: modified_base
<222> LOCATION: (85)..(85)
<223> OTHER INFORMATION: a, c, t, g, unknown or other
<220> FEATURE:
<221> NAME/KEY: modified_base
<222> LOCATION: (116)..(116)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (127)..(129)
<223> OTHER INFORMATION: a, c, t, g, unknown or other
<220> FEATURE:
<221> NAME/KEY: modified_base
<222> LOCATION: (132)..(133)
<223> OTHER INFORMATION: a, c, t, g, unknown or other
<220> FEATURE:
<221> NAME/KEY: modified_base
<222> LOCATION: (135)..(137)
<223> OTHER INFORMATION: a, c, t, g, unknown or other
<220> FEATURE:
<221> NAME/KEY: modified_base
<222> LOCATION: (142)..(143)
<223> OTHER INFORMATION: a, c, t, g, unknown or other
<220> FEATURE:
<221> NAME/KEY: modified_base
<222> LOCATION: (206)..(206)
<223> OTHER INFORMATION: a, c, t, g, unknown or other
<220> FEATURE:
<221> NAME/KEY: modified_base
<222> LOCATION: (222)..(222)
<223> OTHER INFORMATION: a, c, t, g, unknown or other
<220> FEATURE:
<221> NAME/KEY: modified_base
<222> LOCATION: (224)..(225)
<223> OTHER INFORMATION: a, c, t, g, unknown or other
<220> FEATURE:
<221> NAME/KEY: modified_base
<222> LOCATION: (981)..(982)
<223> OTHER INFORMATION: a, c, t, g, unknown or other
<220> FEATURE:
<221> NAME/KEY: modified_base
<222> LOCATION: (985)..(989)
<223> OTHER INFORMATION: a, c, t, g, unknown or other
```

<400> SEQUENCE: 7

```
gnnnnntnnn nggaantgng agcnnnnnna atttnncnca ggaaacagct atgaccanga    60
ttacgccaag cttgcatgca aattntattt caaggagaca gtcataatga aatacntatt   120
gcntacnnnc anncnnngga tnntattact cgcggcccag ccggccatgg cccaggtgca   180
gctgcaggag tctgggggag gcgtgntcca gcctgggagg tncnngagac tctcctgtgc   240
agcgtctgga ttcaccttca gtacttctgg catgcactgg gtccgccagg ctccaggcaa   300
ggggctggag tgggtggcat ttatactaca tgatggaagt gataaatact atgcagactc   360
cgtgaagggc cgattcacca tctccagaga caattccaag aacacgctgt atctgcaaat   420
gaacagcctg agagccgagg acacggccat atattactgt gcgaaatctc agagggagct   480
actcggcgct gaatacctcc agaactgggg ccagggcacc ctggtcaccg tctcctcagg   540
tggaggcggt tcaggcggag gtggctctgg cggtggcgga tcgcagtctg ctctgactca   600
gcctgcctcc gtgtctgggt ctcctggaca gtcgatcacc atctcctgca ctggaaccag   660
cagtgacgtt ggtggttata gtatgtctc ctggtaccaa cagcacccag gcaaagcccc   720
caaagtcatg atttatgatg tcagtaatcg gccctcaggg gtttctaatc gcttctctgg   780
ctccaagtct ggcaacacgg cctccctgac catctctggg ctccaggctg aggacgaggc   840
tgattattac tgcagctcat atacaagcag cagcactctc gtgttcggcg gcgggaccaa   900
ggtcaccgtc ctaggtgcgg ccgcacatca tcatcaccat cacggggccg cagaacaaaa   960
actcatctca gaagaggatc nnaannnnnc g                                  991
```

<210> SEQ ID NO 8
<211> LENGTH: 992
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (889)..(889)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (912)..(914)
<223> OTHER INFORMATION: a, c, t, g, unknown or other
<220> FEATURE:
<221> NAME/KEY: modified_base
<222> LOCATION: (921)..(922)
<223> OTHER INFORMATION: a, c, t, g, unknown or other
<220> FEATURE:
<221> NAME/KEY: modified_base
<222> LOCATION: (946)..(946)
<223> OTHER INFORMATION: a, c, t, g, unknown or other
<220> FEATURE:
<221> NAME/KEY: modified_base
<222> LOCATION: (949)..(949)
<223> OTHER INFORMATION: a, c, t, g, unknown or other
<220> FEATURE:
<221> NAME/KEY: modified_base
<222> LOCATION: (952)..(952)

<223> OTHER INFORMATION: a, c, t, g, unknown or other
<220> FEATURE:
<221> NAME/KEY: modified_base
<222> LOCATION: (963)..(964)
<223> OTHER INFORMATION: a, c, t, g, unknown or other
<220> FEATURE:
<221> NAME/KEY: modified_base
<222> LOCATION: (972)..(972)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
<221> NAME/KEY: modified_base
<222> LOCATION: (980)..(984)
<223> OTHER INFORMATION: a, c, t, g, unknown or other
<220> FEATURE:
<221> NAME/KEY: modified_base
<222> LOCATION: (990)..(990)
<223> OTHER INFORMATION: a, c, t, g, unknown or other

<400> SEQUENCE: 8

```
aattctattt cnggagacag tcataatgaa atacctattg cctacggcag ccgctggatt      60
gttattactc gcggcccagc cggccatggc ccaggtgcag ctgcaggagt ctgggggagg     120
cgtggtccag cctgggaggt ccctgagact ctcctgtgca gcgtctggat tcaccttcag     180
tacttctggc atgcactggg tccgccaggc tccaggcaag gggctggagt gggtggcatt     240
tatactacat gatggaagtg ataaatacta tgcagactcc gtgaagggcc gattcaccat     300
ctccagagac aattccaaga acacgctgta tctgcaaatg aacagcctga gagccgagga     360
cacggccata tattactgtg cgaaatctca gagggagcta ctcggcgctg aatacctcca     420
gaactggggc cagggcaccc tggtcaccgt ctcctcaggt ggaggcggtt caggcggagg     480
tggctctggc ggtggcggat cgcagtctgc tctgactcag cctgcctccg tgtctgggtc     540
tcctggacag tcgatcacca tctcctgcac tggaaccagc agtgacgttg gtggttataa     600
gtatgtctcc tggtaccaac agcacccagg caaagccccc aaagtcatga tttatgatgt     660
cagtaatcgg ccctcagggg tttctaatcg cttctctggc tccaagtctg gcaacacggc     720
ctccctgacc atctctgggc tccaggctga ggacgaggct gattattact gcagctcata     780
tacaagcagc agcactctcg tgttcggcgg cgggaccaag gtcaccgtcc taggtgcggc     840
cgcagaacaa aaactcatct cagaagagga tctgaatggg gccgcatana ctgttgaaag     900
ttntttanca annntcatac nnaaaattca tttactaacg tctggnaana cnacaaaact     960
ttnnatcgtt angctaantn nnnnagggcn gt                                   992
```

<210> SEQ ID NO 9
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:

```
<221> NAME/KEY: MOD_RES
<222> LOCATION: (303)..(305)
<223> OTHER INFORMATION: Any amino acid
<220> FEATURE:
<221> NAME/KEY: MOD_RES
<222> LOCATION: (307)..(307)
<223> OTHER INFORMATION: Any amino acid
<220> FEATURE:
<221> NAME/KEY: MOD_RES
<222> LOCATION: (315)..(317)
<223> OTHER INFORMATION: Any amino acid
<220> FEATURE:
<221> NAME/KEY: MOD_RES
<222> LOCATION: (321)..(321)
<223> OTHER INFORMATION: Any amino acid
<220> FEATURE:
<221> NAME/KEY: MOD_RES
<222> LOCATION: (324)..(324)
<223> OTHER INFORMATION: Any amino acid
<220> FEATURE:
<221> NAME/KEY: MOD_RES
<222> LOCATION: (326)..(328)
<223> OTHER INFORMATION: Any amino acid
<220> FEATURE:
<221> NAME/KEY: MOD_RES
<222> LOCATION: (330)..(330)
<223> OTHER INFORMATION: Any amino acid

<400> SEQUENCE: 9
```

Ile Leu Phe Xaa Glu Thr Val Ile Met Lys Tyr Leu Leu Pro Thr Ala
 1               5                  10                  15

Ala Ala Gly Leu Leu Leu Ala Ala Gln Pro Ala Met Ala Gln Val
             20                  25                  30

Gln Leu Gln Glu Ser Gly Gly Gly Val Val Gln Pro Gly Arg Ser Leu
         35                  40                  45

Arg Leu Ser Cys Ala Ala Ser Gly Phe Thr Phe Ser Thr Ser Gly Met
     50                  55                  60

His Trp Val Arg Gln Ala Pro Gly Lys Gly Leu Glu Trp Val Ala Phe
 65                  70                  75                  80

Ile Leu His Asp Gly Ser Asp Lys Tyr Tyr Ala Asp Ser Val Lys Gly
                 85                  90                  95

Arg Phe Thr Ile Ser Arg Asp Asn Ser Lys Asn Thr Leu Tyr Leu Gln
            100                 105                 110

Met Asn Ser Leu Arg Ala Glu Asp Thr Ala Ile Tyr Tyr Cys Ala Lys
        115                 120                 125

Ser Gln Arg Glu Leu Leu Gly Ala Glu Tyr Leu Gln Asn Trp Gly Gln
    130                 135                 140

Gly Thr Leu Val Thr Val Ser Ser Gly Gly Gly Ser Gly Gly Gly Gly
145                 150                 155                 160

Gly Ser Gly Gly Gly Gly Ser Gln Ser Ala Leu Thr Gln Pro Ala Ser
                165                 170                 175

Val Ser Gly Ser Pro Gly Gln Ser Ile Thr Ile Ser Cys Thr Gly Thr
            180                 185                 190

Ser Ser Asp Val Gly Gly Tyr Lys Tyr Val Ser Trp Tyr Gln Gln His
        195                 200                 205

Pro Gly Lys Ala Pro Lys Val Met Ile Tyr Asp Val Ser Asn Arg Pro
    210                 215                 220

Ser Gly Val Ser Asn Arg Phe Ser Gly Ser Lys Ser Gly Asn Thr Ala
225                 230                 235                 240

Ser Leu Thr Ile Ser Gly Leu Gln Ala Glu Asp Glu Ala Asp Tyr Tyr
                245                 250                 255

Cys Ser Ser Tyr Thr Ser Ser Ser Thr Leu Val Phe Gly Gly Gly Thr

```
                    260                 265                 270
Lys Val Thr Val Leu Gly Ala Ala Glu Gln Lys Leu Ile Ser Glu
        275                 280                 285

Glu Asp Leu Asn Gly Ala Ala Xaa Thr Val Glu Ser Xaa Leu Xaa Xaa
        290                 295                 300

Xaa Ile Xaa Lys Ile His Leu Leu Thr Ser Xaa Xaa Xaa Thr Lys Leu
305                 310                 315                 320

Xaa Ile Val Xaa Leu Xaa Xaa Xaa Gly Xaa
                325                 330

<210> SEQ ID NO 10
<211> LENGTH: 1033
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (900)..(901)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (921)..(922)
<223> OTHER INFORMATION: a, c, t, g, unknown or other
<220> FEATURE:
<221> NAME/KEY: modified_base
<222> LOCATION: (926)..(928)
<223> OTHER INFORMATION: a, c, t, g, unknown or other
<220> FEATURE:
<221> NAME/KEY: modified_base
<222> LOCATION: (934)..(934)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (951)..(953)
<223> OTHER INFORMATION: a, c, t, g, unknown or other
<220> FEATURE:
<221> NAME/KEY: modified_base
<222> LOCATION: (958)..(958)
<223> OTHER INFORMATION: a, c, t, g, unknown or other
<220> FEATURE:
```

<221> NAME/KEY: modified_base
<222> LOCATION: (965)..(968)
<223> OTHER INFORMATION: a, c, t, g, unknown or other
<220> FEATURE:
<221> NAME/KEY: modified_base
<222> LOCATION: (970)..(975)
<223> OTHER INFORMATION: a, c, t, g, unknown or other
<220> FEATURE:
<221> NAME/KEY: modified_base
<222> LOCATION: (985)..(986)
<223> OTHER INFORMATION: a, c, t, g, unknown or other
<220> FEATURE:
<221> NAME/KEY: modified_base
<222> LOCATION: (989)..(990)
<223> OTHER INFORMATION: a, c, t, g, unknown or other
<220> FEATURE:
<221> NAME/KEY: modified_base
<222> LOCATION: (992)..(992)
<223> OTHER INFORMATION: a, c, t, g, unknown or other
<220> FEATURE:
<221> NAME/KEY: modified_base
<222> LOCATION: (996)..(997)
<223> OTHER INFORMATION: a, c, t, g, unknown or other
<220> FEATURE:
<221> NAME/KEY: modified_base
<222> LOCATION: (1002)..(1002)
<223> OTHER INFORMATION: a, c, t, g, unknown or other
<220> FEATURE:
<221> NAME/KEY: modified_base
<222> LOCATION: (1004)..(1007)
<223> OTHER INFORMATION: a, c, t, g, unknown or other
<220> FEATURE:
<221> NAME/KEY: modified_base
<222> LOCATION: (1012)..(1017)
<223> OTHER INFORMATION: a, c, t, g, unknown or other
<220> FEATURE:
<221> NAME/KEY: modified_base
<222> LOCATION: (1021)..(1021)
<223> OTHER INFORMATION: a, c, t, g, unknown or other
<220> FEATURE:
<221> NAME/KEY: modified_base
<222> LOCATION: (1023)..(1025)
<223> OTHER INFORMATION: a, c, t, g, unknown or other
<220> FEATURE:
<221> NAME/KEY: modified_base
<222> LOCATION: (1027)..(1027)
<223> OTHER INFORMATION: a, c, t, g, unknown or other
<220> FEATURE:
<221> NAME/KEY: modified_base
<222> LOCATION: (1029)..(1032)
<223> OTHER INFORMATION: a, c, t, g, unknown or other

<400> SEQUENCE: 10

```
gcanttcnat ttnnngagac agtcataatg aaatacctat tgcctacggc agccgctgga    60
ttgttattac tcgcggccca gccggccatg gcccaggtgc agctggtgga gtctggggga   120
ggcttggtac agcctggggg gtccctgaga ctctcctgtg cagcctctgg attcaccttt   180
agcagctatg ccatgagctg gtccgccag gctccaggga aggggctgga gtgggtctca   240
gctattagtg gtagtggtgg tagcacatac tacgcagact ccgtgaaggg ccggttcacc   300
atctccagag acaattccaa gaacacgctg tatctgcaaa tgaacagcct gagagccgag   360
gacacggctg tatattactg tgcaagaggt ggcgattatg gctcagggga ctactggggc   420
cagggaaccc tggtcaccgt ctcctcaggt ggaggcggtt caggcggagg tggctctggc   480
ggtggcggat cgaatttat gctgactcag accctgctg tgtctgtggc cttgggacag   540
acagtcagaa tcacatgcca aggagacagc ctcagaagct attatgcaag ttggtaccag   600
cagaagccag acaggcccc tctccttgtc atctatggta aaaacatccg gccctcaggg   660
atcccagacc gattctctgg ctccagctca ggaaactcag cttccttgac catcactggg   720
gctcaggcgg aagatgaggc tgactattac tgtcactccc gggacagcag tggtacccat   780
```

```
ctaagggtat tcggcggagg gaccaaggtc accgtcctag gtgcggccgc agaacaaaaa    840
ctcatctcag aagaggatct gaatggggcc gcatanactg ttgaaagttg tttancaaan    900
nctcatacag aaanttnatt nnctannntc tggnaagang acaaaactt nnntcgtnac     960 gctannnntn nnnnntgtct gtganngcnn cnggcnntgt gntnnnnact gnnnnnnaaa   1020
ntnnngntnn nng                                                      1033
```

<210> SEQ ID NO 11
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (292)..(292)
<223> OTHER INFORMATION: Any amino acid
<220> FEATURE:
<221> NAME/KEY: MOD_RES
<222> LOCATION: (299)..(301)
<223> OTHER INFORMATION: Any amino acid
<220> FEATURE:
<221> NAME/KEY: MOD_RES
<222> LOCATION: (305)..(310)
<223> OTHER INFORMATION: Any amino acid
<220> FEATURE:
<221> NAME/KEY: MOD_RES
<222> LOCATION: (312)..(313)
<223> OTHER INFORMATION: Any amino acid
<220> FEATURE:
<221> NAME/KEY: MOD_RES
<222> LOCATION: (317)..(318)
<223> OTHER INFORMATION: Any amino acid
<220> FEATURE:
<221> NAME/KEY: MOD_RES
<222> LOCATION: (320)..(320)
<223> OTHER INFORMATION: Any amino acid
<220> FEATURE:
<221> NAME/KEY: MOD_RES
<222> LOCATION: (322)..(325)
<223> OTHER INFORMATION: Any amino acid

<400> SEQUENCE: 11

```
Ala Xaa Xaa Phe Xaa Glu Thr Val Ile Met Lys Tyr Leu Leu Pro Thr
1               5                   10                  15

Ala Ala Ala Gly Leu Leu Leu Leu Ala Ala Gln Pro Ala Met Ala Gln
            20                  25                  30

Val Gln Leu Val Glu Ser Gly Gly Gly Leu Val Gln Pro Gly Gly Ser
        35                  40                  45

Leu Arg Leu Ser Cys Ala Ala Ser Gly Phe Thr Phe Ser Ser Tyr Ala
    50                  55                  60

Met Ser Trp Val Arg Gln Ala Pro Gly Lys Gly Leu Glu Trp Val Ser
65                  70                  75                  80

Ala Ile Ser Gly Ser Gly Gly Ser Thr Tyr Tyr Ala Asp Ser Val Lys
                85                  90                  95

Gly Arg Phe Thr Ile Ser Arg Asp Asn Ser Lys Asn Thr Leu Tyr Leu
            100                 105                 110
```

-continued

```
Gln Met Asn Ser Leu Arg Ala Glu Asp Thr Ala Val Tyr Tyr Cys Ala
            115                 120                 125

Arg Gly Gly Asp Tyr Gly Ser Gly Asp Tyr Trp Gly Gln Gly Thr Leu
        130                 135                 140

Val Thr Val Ser Ser Gly Gly Gly Gly Ser Gly Gly Gly Gly Ser Gly
145                 150                 155                 160

Gly Gly Gly Ser Asn Phe Met Leu Thr Gln Asp Pro Ala Val Ser Val
                165                 170                 175

Ala Leu Gly Gln Thr Val Arg Ile Thr Cys Gln Gly Asp Ser Leu Arg
            180                 185                 190

Ser Tyr Tyr Ala Ser Trp Tyr Gln Gln Lys Pro Gly Gln Ala Pro Leu
        195                 200                 205

Leu Val Ile Tyr Gly Lys Asn Ile Arg Pro Ser Gly Ile Pro Asp Arg
    210                 215                 220

Phe Ser Gly Ser Ser Ser Gly Asn Ser Ala Ser Leu Thr Ile Thr Gly
225                 230                 235                 240

Ala Gln Ala Glu Asp Glu Ala Asp Tyr Tyr Cys His Ser Arg Asp Ser
                245                 250                 255

Ser Gly Thr His Leu Arg Val Phe Gly Gly Gly Thr Lys Val Thr Val
            260                 265                 270

Leu Gly Ala Ala Ala Glu Gln Lys Leu Ile Ser Glu Glu Asp Leu Asn
        275                 280                 285

Gly Ala Ala Xaa Thr Val Glu Ser Cys Leu Xaa Xaa Xaa His Thr Glu
    290                 295                 300

Xaa Xaa Xaa Xaa Xaa Xaa Trp Xaa Xaa Asp Lys Thr Xaa Xaa Arg Xaa
305                 310                 315                 320

Ala Xaa Xaa Xaa Xaa Cys Leu
            325

<210> SEQ ID NO 12
<211> LENGTH: 994
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (905)..(905)
<223> OTHER INFORMATION: a, c, t, g, unknown or other
<220> FEATURE:
<221> NAME/KEY: modified_base
<222> LOCATION: (908)..(910)
<223> OTHER INFORMATION: a, c, t, g, unknown or other
<220> FEATURE:
<221> NAME/KEY: modified_base
<222> LOCATION: (927)..(927)
<223> OTHER INFORMATION: a, c, t, g, unknown or other
<220> FEATURE:
<221> NAME/KEY: modified_base
<222> LOCATION: (952)..(953)
<223> OTHER INFORMATION: a, c, t, g, unknown or other
<220> FEATURE:
```

<221> NAME/KEY: modified_base
<222> LOCATION: (971)..(972)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
<221> NAME/KEY: modified_base
<222> LOCATION: (982)..(983)
<223> OTHER INFORMATION: a, c, t, g, unknown or other
<220> FEATURE:
<221> NAME/KEY: modified_base
<222> LOCATION: (985)..(985)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (993)..(993)
<223> OTHER INFORMATION: a, c, t, g, unknown or other

<400> SEQUENCE: 12

```
gcnnntctat ttaaggagac agtcataatg aaatacctat tgcctacggc agccgctgga      60
ttgttattac tcgcggccca gccggccatg cccaggtgc agctggtggc gtctggagga     120
gacttgatcc agcctggggg gtccctgaga ctctcctgtg cagcctctgg attcaccttt    180
aataactatt ggatgacctg gtccgccag gctccaggga aggggctgga gtgggtggcc    240
aacataaagc aagatggagg tgagaaatac tatgtggact ctgtgaaggg ccgattcacc    300
atctccagag acaacgccaa gacctcactg tatctgcaaa tgaacagcct gagagccgag    360
gacacggccg tgtattattg tgcgaaagag tcgtatagca ctggctggtt tgaccactgg    420
ggccagggaa ccctggtcac cgtctcctca ggtggaggcg gttcaggcgg aggtggctct    480
ggcggtggcg gatcgaattt tatgctgact caggaccctg ctgtgtctgt ggccttggga    540
cagacagtca ggataacatg tcaaggtgac agcctcagaa atattatac aagttggtac     600
caacagaagc caggacaggc ccctctactt gtcatgtatg cgaaaaataa ccggccctca    660
gggatcccag accgattctc tggctccagc tcaggaaaca cagcttcctt gaccatcact    720
ggggctcagg cggaagatga ggctgactat tactgtgact cccgggacag cagtggtgac    780
cattgggtgt tcggcggagg gaccaagctg accgttctag gtgcggccgc agaacaaaaa    840
ctcatctcag aagaggatct gaatggggcc gcatanactg ttgaaagttg tttancaaaa    900
cctcntannn aaaattcatt tactaangtc tggaaagacg acaaaacttt anntcgttac    960
gctaactatg nnggctgnct gnngnangct acng                                994
```

<210> SEQ ID NO 13
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (292)..(292)
<223> OTHER INFORMATION: Any amino acid
<220> FEATURE:
<221> NAME/KEY: MOD_RES
<222> LOCATION: (299)..(299)

```
<223> OTHER INFORMATION: Any amino acid
<220> FEATURE:
<221> NAME/KEY: MOD_RES
<222> LOCATION: (302)..(304)
<223> OTHER INFORMATION: Any amino acid
<220> FEATURE:
<221> NAME/KEY: MOD_RES
<222> LOCATION: (309)..(309)
<223> OTHER INFORMATION: Any amino acid
<220> FEATURE:
<221> NAME/KEY: MOD_RES
<222> LOCATION: (318)..(318)
<223> OTHER INFORMATION: Any amino acid
<220> FEATURE:
<221> NAME/KEY: MOD_RES
<222> LOCATION: (324)..(324)
<223> OTHER INFORMATION: Any amino acid
<220> FEATURE:
<221> NAME/KEY: MOD_RES
<222> LOCATION: (326)..(326)
<223> OTHER INFORMATION: Any amino acid
<220> FEATURE:
<221> NAME/KEY: MOD_RES
<222> LOCATION: (328)..(329)
<223> OTHER INFORMATION: Any amino acid
<220> FEATURE:
<221> NAME/KEY: MOD_RES
<222> LOCATION: (331)..(331)
<223> OTHER INFORMATION: Any amino acid

<400> SEQUENCE: 13

Xaa Xaa Leu Phe Lys Glu Thr Val Ile Met Lys Tyr Leu Leu Pro Thr
1               5                   10                  15

Ala Ala Ala Gly Leu Leu Leu Ala Ala Gln Pro Ala Met Ala Gln
            20                  25                  30

Val Gln Leu Val Ala Ser Gly Gly Asp Leu Ile Gln Pro Gly Gly Ser
        35                  40                  45

Leu Arg Leu Ser Cys Ala Ala Ser Gly Phe Thr Phe Asn Asn Tyr Trp
    50                  55                  60

Met Thr Trp Val Arg Gln Ala Pro Gly Lys Gly Leu Glu Trp Val Ala
65                  70                  75                  80

Asn Ile Lys Gln Asp Gly Gly Glu Lys Tyr Tyr Val Asp Ser Val Lys
                85                  90                  95

Gly Arg Phe Thr Ile Ser Arg Asp Asn Ala Lys Thr Ser Leu Tyr Leu
            100                 105                 110

Gln Met Asn Ser Leu Arg Ala Glu Asp Thr Ala Val Tyr Tyr Cys Ala
        115                 120                 125

Lys Glu Ser Tyr Ser Thr Gly Trp Phe Asp His Trp Gly Gln Gly Thr
    130                 135                 140

Leu Val Thr Val Ser Ser Gly Gly Gly Ser Gly Gly Gly Gly Ser
145                 150                 155                 160

Gly Gly Gly Gly Ser Asn Phe Met Leu Thr Gln Asp Pro Ala Val Ser
                165                 170                 175

Val Ala Leu Gly Gln Thr Val Arg Ile Thr Cys Gln Gly Asp Ser Leu
            180                 185                 190

Arg Lys Tyr Tyr Thr Ser Trp Tyr Gln Gln Lys Pro Gly Gln Ala Pro
        195                 200                 205

Leu Leu Val Met Tyr Ala Lys Asn Asn Arg Pro Ser Gly Ile Pro Asp
    210                 215                 220

Arg Phe Ser Gly Ser Ser Ser Gly Asn Thr Ala Ser Leu Thr Ile Thr
225                 230                 235                 240

Gly Ala Gln Ala Glu Asp Glu Ala Asp Tyr Tyr Cys Asp Ser Arg Asp
                245                 250                 255
```

```
Ser Ser Gly Asp His Trp Val Phe Gly Gly Thr Lys Leu Thr Val
            260                 265                 270

Leu Gly Ala Ala Ala Glu Gln Lys Leu Ile Ser Glu Glu Asp Leu Asn
        275                 280                 285

Gly Ala Ala Xaa Thr Val Glu Ser Cys Leu Xaa Lys Pro Xaa Xaa Xaa
    290                 295                 300

Asn Ser Phe Thr Xaa Val Trp Lys Asp Asp Lys Thr Leu Xaa Arg Tyr
305                 310                 315                 320

Ala Asn Tyr Xaa Gly Xaa Leu Xaa Xaa Ala Xaa
            325                 330
```

<210> SEQ ID NO 14
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(5)
<223> OTHER INFORMATION: a, c, t, g, unknown or other
<220> FEATURE:
<221> NAME/KEY: modified_base
<222> LOCATION: (8)..(10)
<223> OTHER INFORMATION: a, c, t, g, unknown or other
<220> FEATURE:
<221> NAME/KEY: modified_base
<222> LOCATION: (865)..(865)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
<220> FEATURE:
<221> NAME/KEY: modified_base
<222> LOCATION: (884)..(884)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (931)..(931)
<223> OTHER INFORMATION: a, c, t, g, unknown or other
<220> FEATURE:
<221> NAME/KEY: modified_base
<222> LOCATION: (941)..(941)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
<221> NAME/KEY: modified_base
<222> LOCATION: (959)..(961)
<223> OTHER INFORMATION: a, c, t, g, unknown or other
<220> FEATURE:
<221> NAME/KEY: modified_base
<222> LOCATION: (964)..(964)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (975)..(975)

<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other

<400> SEQUENCE: 14

```
tnnnnttnnn gagacagtca taatgaaata cctattgcct acggcagccg ctggattgtt      60
attactcgcg gcccagccgg ccatggcccg agtgcagctg gtggagtctg ggctgaggt     120
gacgaagcct ggggcctcag taagggtctc ctgcaaggct tctggataca ccttcagcag    180
atatgatatc aactgggtgc gacaggcctc tggacaaggg cttgagtgga tgggatggat    240
caaccctaac agtggtaaca caggctatgc acagaagttc cagggcagag tcaccatgac    300
caggaatatt tccataacca cggcctacat ggagctgagc agcctgagat ctgaggacac    360
ggccgtatat tactgtgcga gaggccttcc ggagttcgac ccctggggcc agggaaccct    420
ggtcaccgtc tcctcaggtg gaggcggttc aggcggaggt ggctctggcg gtggcggatc    480
gcacgttata ctgactcagg accctgctgt gtctgtggcc ttgggacaga cagtcaggat    540
cacatgccaa ggagacagcc tcagaagcta ttatgcaagc tggtaccagc agaagccagg    600
acaggcccct gtacttgtca tctatggtaa aaacaaccgg ccctcaggga tcccagaccg    660
attctctggc tccagctcag gaaacacagc ttccttgacc atcactgggg ctcaggcgga    720
agatgaggct gacttttact gtaattcccg ggacagcagt ggcacccatc tagaggtgtt    780
cggcggaggg accaaggtca ccgtcctagg tgcggccgca gaacaaaaac tcatctcaga    840
agaggatctg aatggggccg catanactgn tgaaagttgt ttancaaaac ctcntacaga    900
aaattcattt actaacgtct ggaaagacga naaaacttta natcgttacn ctaactatnn    960
nggntgtctg ngnantgnta c                                              981
```

<210> SEQ ID NO 15
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (289)..(289)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (299)..(299)
<223> OTHER INFORMATION: Any amino acid
<220> FEATURE:
<221> NAME/KEY: MOD_RES
<222> LOCATION: (311)..(311)
<223> OTHER INFORMATION: Any amino acid
<220> FEATURE:
<221> NAME/KEY: MOD_RES
<222> LOCATION: (315)..(315)
<223> OTHER INFORMATION: Any amino acid
<220> FEATURE:

```
<221> NAME/KEY: MOD_RES
<222> LOCATION: (318)..(318)
<223> OTHER INFORMATION: Any amino acid
<220> FEATURE:
<221> NAME/KEY: MOD_RES
<222> LOCATION: (321)..(322)
<223> OTHER INFORMATION: Any amino acid
<220> FEATURE:
<221> NAME/KEY: MOD_RES
<222> LOCATION: (325)..(327)
<223> OTHER INFORMATION: Any amino acid

<400> SEQUENCE: 15

Ala Xaa Xaa Xaa Glu Thr Val Ile Met Lys Tyr Leu Leu Pro Thr Ala
1               5                   10                  15

Ala Ala Gly Leu Leu Leu Ala Ala Gln Pro Ala Met Ala Arg Val
            20                  25                  30

Gln Leu Val Glu Ser Gly Ala Glu Val Thr Lys Pro Gly Ala Ser Val
        35                  40                  45

Arg Val Ser Cys Lys Ala Ser Gly Tyr Thr Phe Ser Arg Tyr Asp Ile
    50                  55                  60

Asn Trp Val Arg Gln Ala Ser Gly Gln Gly Leu Glu Trp Met Gly Trp
65                  70                  75                  80

Ile Asn Pro Asn Ser Gly Asn Thr Gly Tyr Ala Gln Lys Phe Gln Gly
                85                  90                  95

Arg Val Thr Met Thr Arg Asn Ile Ser Ile Thr Thr Ala Tyr Met Glu
            100                 105                 110

Leu Ser Ser Leu Arg Ser Glu Asp Thr Ala Val Tyr Tyr Cys Ala Arg
        115                 120                 125

Gly Leu Pro Glu Phe Asp Pro Trp Gly Gln Gly Thr Leu Val Thr Val
    130                 135                 140

Ser Ser Gly Gly Gly Ser Gly Gly Gly Ser Gly Gly Gly Gly
145                 150                 155                 160

Ser His Val Ile Leu Thr Gln Asp Pro Ala Val Ser Val Ala Leu Gly
                165                 170                 175

Gln Thr Val Arg Ile Thr Cys Gln Gly Asp Ser Leu Arg Ser Tyr Tyr
            180                 185                 190

Ala Ser Trp Tyr Gln Gln Lys Pro Gly Gln Ala Pro Val Leu Val Ile
        195                 200                 205

Tyr Gly Lys Asn Asn Arg Pro Ser Gly Ile Pro Asp Arg Phe Ser Gly
    210                 215                 220

Ser Ser Ser Gly Asn Thr Ala Ser Leu Thr Ile Thr Gly Ala Gln Ala
225                 230                 235                 240

Glu Asp Glu Ala Asp Phe Tyr Cys Asn Ser Arg Asp Ser Ser Gly Thr
                245                 250                 255

His Leu Glu Val Phe Gly Gly Gly Thr Lys Val Thr Val Leu Gly Ala
            260                 265                 270

Ala Ala Glu Gln Lys Leu Ile Ser Glu Glu Asp Leu Asn Gly Ala Ala
        275                 280                 285

Xaa Thr Xaa Glu Ser Cys Leu Xaa Lys Pro Xaa Thr Glu Asn Ser Phe
    290                 295                 300

Thr Asn Val Trp Lys Asp Xaa Lys Thr Leu Xaa Arg Tyr Xaa Asn Tyr
305                 310                 315                 320

Xaa Xaa Cys Leu Xaa Xaa Xaa
                325

<210> SEQ ID NO 16
```

```
<211> LENGTH: 1041
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (11)..(13)
<223> OTHER INFORMATION: a, c, t, g, unknown or other
<220> FEATURE:
<221> NAME/KEY: modified_base
<222> LOCATION: (706)..(706)
<223> OTHER INFORMATION: a, c, t, g, unknown or other
<220> FEATURE:
<221> NAME/KEY: modified_base
<222> LOCATION: (746)..(746)
<223> OTHER INFORMATION: a, c, t, g, unknown or other
<220> FEATURE:
<221> NAME/KEY: modified_base
<222> LOCATION: (748)..(748)
<223> OTHER INFORMATION: a, c, t, g, unknown or other
<220> FEATURE:
<221> NAME/KEY: modified_base
<222> LOCATION: (771)..(773)
<223> OTHER INFORMATION: a, c, t, g, unknown or other
<220> FEATURE:
<221> NAME/KEY: modified_base
<222> LOCATION: (796)..(796)
<223> OTHER INFORMATION: a, c, t, g, unknown or other
<220> FEATURE:
<221> NAME/KEY: modified_base
<222> LOCATION: (803)..(803)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (833)..(833)
<223> OTHER INFORMATION: a, c, t, g, unknown or other
<220> FEATURE:
<221> NAME/KEY: modified_base
<222> LOCATION: (851)..(851)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (857)..(857)
<223> OTHER INFORMATION: a, c, t, g, unknown or other
<220> FEATURE:
<221> NAME/KEY: modified_base
<222> LOCATION: (859)..(860)
<223> OTHER INFORMATION: a, c, t, g, unknown or other
<220> FEATURE:
<221> NAME/KEY: modified_base
<222> LOCATION: (862)..(862)
<223> OTHER INFORMATION: a, c, t, g, unknown or other
<220> FEATURE:
<221> NAME/KEY: modified_base
<222> LOCATION: (875)..(875)
<223> OTHER INFORMATION: a, c, t, g, unknown or other
<220> FEATURE:
<221> NAME/KEY: modified_base
<222> LOCATION: (878)..(878)
<223> OTHER INFORMATION: a, c, t, g, unknown or other
<220> FEATURE:
<221> NAME/KEY: modified_base
<222> LOCATION: (883)..(883)
<223> OTHER INFORMATION: a, c, t, g, unknown or other
<220> FEATURE:
```

-continued

```
<221> NAME/KEY: modified_base
<222> LOCATION: (900)..(900)
<223> OTHER INFORMATION: a, c, t, g, unknown or other
<220> FEATURE:
<221> NAME/KEY: modified_base
<222> LOCATION: (913)..(913)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (925)..(925)
<223> OTHER INFORMATION: a, c, t, g, unknown or other
<220> FEATURE:
<221> NAME/KEY: modified_base
<222> LOCATION: (928)..(931)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (935)..(936)
<223> OTHER INFORMATION: a, c, t, g, unknown or other
<220> FEATURE:
<221> NAME/KEY: modified_base
<222> LOCATION: (944)..(944)
<223> OTHER INFORMATION: a, c, t, g, unknown or other
<220> FEATURE:
<221> NAME/KEY: modified_base
<222> LOCATION: (946)..(946)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (950)..(952)
<223> OTHER INFORMATION: a, c, t, g, unknown or other
<220> FEATURE:
<221> NAME/KEY: modified_base
<222> LOCATION: (954)..(955)
<223> OTHER INFORMATION: a, c, t, g, unknown or other
<220> FEATURE:
<221> NAME/KEY: modified_base
<222> LOCATION: (957)..(958)
<223> OTHER INFORMATION: a, c, t, g, unknown or other
<220> FEATURE:
<221> NAME/KEY: modified_base
<222> LOCATION: (966)..(966)
<223> OTHER INFORMATION: a, c, t, g, unknown or other
<220> FEATURE:
<221> NAME/KEY: modified_base
<222> LOCATION: (969)..(969)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (977)..(980)
<223> OTHER INFORMATION: a, c, t, g, unknown or other
<220> FEATURE:
<221> NAME/KEY: modified_base
<222> LOCATION: (983)..(983)
<223> OTHER INFORMATION: a, c, t, g, unknown or other
<220> FEATURE:
<221> NAME/KEY: modified_base
<222> LOCATION: (985)..(988)
<223> OTHER INFORMATION: a, c, t, g, unknown or other
```

```
<220> FEATURE:
<221> NAME/KEY: modified_base
<222> LOCATION: (990)..(992)
<223> OTHER INFORMATION: a, c, t, g, unknown or other
<220> FEATURE:
<221> NAME/KEY: modified_base
<222> LOCATION: (994)..(994)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (998)..(999)
<223> OTHER INFORMATION: a, c, t, g, unknown or other
<220> FEATURE:
<221> NAME/KEY: modified_base
<222> LOCATION: (1001)..(1011)
<223> OTHER INFORMATION: a, c, t, g, unknown or other
<220> FEATURE:
<221> NAME/KEY: modified_base
<222> LOCATION: (1013)..(1013)
<223> OTHER INFORMATION: a, c, t, g, unknown or other
<220> FEATURE:
<221> NAME/KEY: modified_base
<222> LOCATION: (1015)..(1017)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1022)..(1027)
<223> OTHER INFORMATION: a, c, t, g, unknown or other
<220> FEATURE:
<221> NAME/KEY: modified_base
<222> LOCATION: (1029)..(1034)
<223> OTHER INFORMATION: a, c, t, g, unknown or other
<220> FEATURE:
<221> NAME/KEY: modified_base
<222> LOCATION: (1036)..(1036)
<223> OTHER INFORMATION: a, c, t, g, unknown or other
<220> FEATURE:
<221> NAME/KEY: modified_base
<222> LOCATION: (1040)..(1040)
<223> OTHER INFORMATION: a, c, t, g, unknown or other

<400> SEQUENCE: 16
anttctattt nnngagacag tcataatgaa atacctattg cctacggcag ccgctggatt      60
gttattactc gcggcccagc cggccatggc ccaggtacag ctgcaggagt ctggggagg      120 cttggtccag cctggaggt ccctgagact ctcctgtgca gcctctggat tcaccttcag      180
taactttggc atgcactggg tctgccaggc tccaggcaag gggctggagt gggtggcaat      240
tatttcatat gatgcaagta gtgaatacta tgcagactcc gtgaagggcc gattcaccat      300
ctccagagac aattccagga acactcttta tctgcaaatg aacagcctga gacctgagga      360
cacggctgta tattactgtg cgaagaagga cggtcggagt gggagctact actactttga      420 ctactgggc cagggaaccc tggtcaccgt ctcctcaggt ggaggcggtt caggcggagg      480
tggctctggc ggtggcggat cggatgttgt gatgactcag tctccatcct ccctgtctgc      540
atctgtagga gacagagtca ccatcacttg ccgggcgagt caagatttta ggaattggtt      600
agcctggtat caggtgaaac caggaaaagc ccccaagccc ctgatctatg gtgcatccac      660
tttgcaaaat ggggtcccat ccaggttcag cggcagtggg tctganacag atttctctct      720
cactatcagc agcctgcagc ctgagnantt tgcaacttac tttttgtcaac nnntcacagt      780 ttccctccca ctttcncgga ggnacacgac tgganatcaa acgtgcggcc gcncatcatc      840
```

```
atcaccatca ngggncncnn anaaaactca tctcnaanag ganctgaatg ggccgcatan      900
actgtgaagt tgnttancaa actcntannn nantnnttta ctangncngn nnannannaa      960
cttaantcnt ncnctannnn gangnnnncn nngnangnna nnnnnnnnnn ngntnnnacn     1020
gnnnnnnann nnnngntacn g                                              1041
```

```
<210> SEQ ID NO 17
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (235)..(235)
<223> OTHER INFORMATION: Any amino acid
<220> FEATURE:
<221> NAME/KEY: MOD_RES
<222> LOCATION: (249)..(249)
<223> OTHER INFORMATION: Any amino acid
<220> FEATURE:
<221> NAME/KEY: MOD_RES
<222> LOCATION: (257)..(258)
<223> OTHER INFORMATION: Any amino acid
<220> FEATURE:
<221> NAME/KEY: MOD_RES
<222> LOCATION: (265)..(265)
<223> OTHER INFORMATION: Any amino acid
<220> FEATURE:
<221> NAME/KEY: MOD_RES
<222> LOCATION: (268)..(268)
<223> OTHER INFORMATION: Any amino acid
<220> FEATURE:
<221> NAME/KEY: MOD_RES
<222> LOCATION: (272)..(272)
<223> OTHER INFORMATION: Any amino acid
<220> FEATURE:
<221> NAME/KEY: MOD_RES
<222> LOCATION: (278)..(278)
<223> OTHER INFORMATION: Any amino acid
<220> FEATURE:
<221> NAME/KEY: MOD_RES
<222> LOCATION: (284)..(287)
<223> OTHER INFORMATION: Any amino acid
<220> FEATURE:
<221> NAME/KEY: MOD_RES
<222> LOCATION: (292)..(294)
<223> OTHER INFORMATION: Any amino acid
<220> FEATURE:
<221> NAME/KEY: MOD_RES
<222> LOCATION: (300)..(300)
<223> OTHER INFORMATION: Any amino acid

<400> SEQUENCE: 17

Xaa Leu Phe Xaa Glu Thr Val Ile Met Lys Tyr Leu Leu Pro Thr Ala
1               5                   10                  15

Ala Ala Gly Leu Leu Leu Leu Ala Ala Gln Pro Ala Met Ala Gln Val
            20                  25                  30

Gln Leu Gln Glu Ser Gly Gly Gly Leu Val Gln Pro Gly Arg Ser Leu
        35                  40                  45

Arg Leu Ser Cys Ala Ala Ser Gly Phe Thr Phe Ser Asn Phe Gly Met
    50                  55                  60
```

His Trp Val Cys Gln Ala Pro Gly Lys Gly Leu Glu Trp Val Ala Ile
 65                  70                  75                  80

Ile Ser Tyr Asp Ala Ser Ser Glu Tyr Tyr Ala Asp Ser Val Lys Gly
             85                  90                  95

Arg Phe Thr Ile Ser Arg Asp Asn Ser Arg Asn Thr Leu Tyr Leu Gln
            100                 105                 110

Met Asn Ser Leu Arg Pro Glu Asp Thr Ala Val Tyr Tyr Cys Ala Lys
        115                 120                 125

Lys Asp Gly Arg Ser Gly Ser Tyr Tyr Tyr Phe Asp Tyr Trp Gly Gln
    130                 135                 140

Gly Thr Leu Val Thr Val Ser Ser Gly Gly Gly Ser Gly Gly Gly Gly
145                 150                 155                 160

Gly Ser Gly Gly Gly Gly Ser Asp Val Val Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Asp Phe Arg Asn Trp Leu Ala Trp Tyr Gln Val Lys Pro Gly
        195                 200                 205

Lys Ala Pro Lys Pro Leu Ile Tyr Gly Ala Ser Thr Leu Gln Asn Gly
    210                 215                 220

Val Pro Ser Arg Phe Ser Gly Ser Gly Ser Xaa Thr Asp Phe Ser Leu
225                 230                 235                 240

Thr Ile Ser Ser Leu Gln Pro Glu Xaa Phe Ala Thr Tyr Phe Cys Gln
                245                 250                 255

Xaa Xaa Thr Val Ser Leu Pro Leu Xaa Arg Arg Xaa Thr Thr Gly Xaa
        260                 265                 270

Gln Thr Cys Gly Arg Xaa Ser Ser Pro Ser Xaa Xaa Xaa Xaa Lys
    275                 280                 285

Thr His Leu Xaa Xaa Xaa Leu Asn Gly Pro His Xaa Leu
    290                 295                 300

<210> SEQ ID NO 18
<211> LENGTH: 989
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: modified_base
<222> LOCATION: (691)..(691)
<223> OTHER INFORMATION: a, c, t, g, unknown or other
<220> FEATURE:
<221> NAME/KEY: modified_base
<222> LOCATION: (727)..(727)
<223> OTHER INFORMATION: a, c, t, g, unknown or other
<220> FEATURE:
<221> NAME/KEY: modified_base
<222> LOCATION: (877)..(877)
<223> OTHER INFORMATION: a, c, t, g, unknown or other
<220> FEATURE:
<221> NAME/KEY: modified_base
<222> LOCATION: (896)..(896)
<223> OTHER INFORMATION: a, c, t, g, unknown or other
<220> FEATURE:
<221> NAME/KEY: modified_base
<222> LOCATION: (898)..(898)
<223> OTHER INFORMATION: a, c, t, g, unknown or other
<220> FEATURE:
<221> NAME/KEY: modified_base
<222> LOCATION: (910)..(911)
<223> OTHER INFORMATION: a, c, t, g, unknown or other
<220> FEATURE:
<221> NAME/KEY: modified_base
<222> LOCATION: (935)..(935)
<223> OTHER INFORMATION: a, c, t, g, unknown or other
<220> FEATURE:
<221> NAME/KEY: modified_base
<222> LOCATION: (938)..(938)
<223> OTHER INFORMATION: a, c, t, g, unknown or other
<220> FEATURE:
<221> NAME/KEY: modified_base
<222> LOCATION: (941)..(941)
<223> OTHER INFORMATION: a, c, t, g, unknown or other
<220> FEATURE:
<221> NAME/KEY: modified_base
<222> LOCATION: (952)..(952)
<223> OTHER INFORMATION: a, c, t, g, unknown or other
<220> FEATURE:
<221> NAME/KEY: modified_base
<222> LOCATION: (980)..(980)
<223> OTHER INFORMATION: a, c, t, g, unknown or other
<220> FEATURE:
<221> NAME/KEY: modified_base
<222> LOCATION: (982)..(982)
<223> OTHER INFORMATION: a, c, t, g, unknown or other
<220> FEATURE:
<221> NAME/KEY: modified_base
<222> LOCATION: (984)..(984)
<223> OTHER INFORMATION: a, c, t, g, unknown or other

<400> SEQUENCE: 18

| | | | | | |
|---|---|---|---|---|---|
| gnnnntcnat | ttnnngagac | agtcataatg | aaatacctat | tgcctacggc | agccgctgga | 60 |
| ttgttattac | tcgcggccca | gccggccatg | gcccaggtgc | agctgcagga | gtctggggga | 120 |
| gacgtggtcc | agcctgggag | gtccctgaga | ctctcctgtg | cagcctctgg | attcaccttc | 180 |
| agtagctatg | gcatgcactg | ggtccgccag | gctccaggca | aggggctgga | gtgggtggca | 240 |
| gttatatcat | atgatgaaag | taataaatac | tatgcagact | ccgtgaaggg | ccgattcacc | 300 |
| atctccagag | acaattccaa | gaacacactg | tttctgcaaa | tgaacagcct | gagagctgag | 360 |
| gacacggctg | tgtattactg | tgcgaaagga | cctgtcctaa | ctggggagtt | tgactattgg | 420 |
| ggccgtagaa | ccctggtcac | cgtctcctca | ggtggaggcg | gttcaggcgg | aggtggctct | 480 |
| ggcggtggcg | gatcgtctga | gctgactcag | gaccctgctg | tgtctgtggc | cttgggacag | 540 |
| acagtcagga | tcacatgcca | aggagacagc | ctcaaaagct | actatgcaag | ttggtaccag | 600 |
| cagaagccag | gacaggcccc | tgtacttgtc | atctatggtg | aaaacagccg | gccctccggg | 660 |
| atcccagacc | gattctctgg | ttccagctca | ngaaacacag | cttccttgac | catcactggg | 720 |
| ggctcangcg | gaagatgaag | ctgactatta | ttgtaactcc | cgggacaaca | gtggtaccca | 780 |
| tcttgaggta | ttcggcggag | ggaccaagct | gaccgtccta | ggtgcggccg | cagaacaaaa | 840 |
| actcatctca | gaagaggatc | tgaatggggc | cgcatanact | gttgaaagtt | gtttancnaa | 900 |
| acctcatacn | naaaattcat | ttactaacgt | ctggnaanac | nacaaacttt | anatcgttac | 960 |
| gctaactatg | agggctgtcn | gngnaatgc | | | | 989 |

<210> SEQ ID NO 19
<211> LENGTH: 245
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (243)..(243)
<223> OTHER INFORMATION: Any amino acid

<400> SEQUENCE: 19

Xaa Xaa Xaa Phe Xaa Glu Thr Val Ile Met Lys Tyr Leu Leu Pro Thr
1               5                   10                  15

Ala Ala Ala Gly Leu Leu Leu Ala Ala Gln Pro Ala Met Ala Gln
            20                  25                  30

Val Gln Leu Gln Glu Ser Gly Gly Asp Val Val Gln Pro Gly Arg Ser
            35                  40                  45

Leu Arg Leu Ser Cys Ala Ala Ser Gly Phe Thr Phe Ser Ser Tyr Gly
50                  55                  60

Met His Trp Val Arg Gln Ala Pro Gly Lys Gly Leu Glu Trp Val Ala
65                  70                  75                  80

Val Ile Ser Tyr Asp Glu Ser Asn Lys Tyr Tyr Ala Asp Ser Val Lys
                85                  90                  95

Gly Arg Phe Thr Ile Ser Arg Asp Asn Ser Lys Asn Thr Leu Phe Leu
            100                 105                 110

Gln Met Asn Ser Leu Arg Ala Glu Asp Thr Ala Val Tyr Tyr Cys Ala
        115                 120                 125

Lys Gly Pro Val Leu Thr Gly Glu Phe Asp Tyr Trp Gly Arg Arg Thr
130                 135                 140

Leu Val Thr Val Ser Ser Gly Gly Gly Gly Ser Gly Gly Gly Gly Ser
145                 150                 155                 160

Gly Gly Gly Gly Ser Ser Glu Leu Thr Gln Asp Pro Ala Val Ser Val
                165                 170                 175

Ala Leu Gly Gln Thr Val Arg Ile Thr Cys Gln Gly Asp Ser Leu Lys
            180                 185                 190

Ser Tyr Tyr Ala Ser Trp Tyr Gln Gln Lys Pro Gly Gln Ala Pro Val
        195                 200                 205

Leu Val Ile Tyr Gly Glu Asn Ser Arg Pro Ser Gly Ile Pro Asp Arg
    210                 215                 220

Phe Ser Gly Ser Ser Xaa Asn Thr Ala Ser Leu Thr Ile Thr Gly
225                 230                 235                 240

Gly Ser Xaa Gly Arg
            245

<210> SEQ ID NO 20
<211> LENGTH: 892
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gagacagtca taatgaaata cctattgcct acggcagccg ctggattgtt attactcgcg    60
gcccagccgg ccatggccca ggtacagctg caggagtctg ggggaggctt ggtacagcct   120
ggggggtccc tgagactctc ctgtgcagcc tctggattca cctttagcag ctatgccatg   180
agctgggtcc gccaggctcc agggaagggg ctggagtggg tctcagctat tagtggtagt   240
ggtggtagca catactacgc agactccgtg aagggccgat tcaccatctc cagagacaat   300
tccaagaaca cgctgtatct gcaaatgaac agcctgagag ctgaggacac ggctgtgtat   360
tactgtgcga gagctatgg ttcagttaaa ataagctgct ttgactactg gggccagagc    420
accctggtca ccgtctcctc aggtggaggc ggttcaggcg gaggtggctc tgcggtggc    480
ggatcggaaa ttgtgctgac gcagtctcca gactccctgg ctgtgtctct gggcgagagg   540
gccaccatca actgcaagtc cagccagagt gttctttaca actccaacaa taagaactac   600
ttagcttggt accagcagaa accaggacag tctcctgagt tgctcattta ctgggcatca   660
acccgggaat ccggggtccc tgaccgattc agtggcagcg ggtctgggac agaattcact   720
cttaccatca gcagcctgca ggctgaggat gtggcagttt attactgtca gcaatttttat  780
agtactcctc cgacttttgg ccaggggacc aagctggaga tcaaacgtgc ggccgcacat   840
catcatcacc atcacggggc cgcagaacaa aaactcatct cagaagagga tc           892
```

<210> SEQ ID NO 21
<211> LENGTH: 977
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: modified_base
<222> LOCATION: (707)..(707)
<223> OTHER INFORMATION: a, c, t, g, unknown or other
<220> FEATURE:
<221> NAME/KEY: modified_base
<222> LOCATION: (747)..(747)
<223> OTHER INFORMATION: a, c, t, g, unknown or other
<220> FEATURE:
<221> NAME/KEY: modified_base
<222> LOCATION: (749)..(749)
<223> OTHER INFORMATION: a, c, t, g, unknown or other
<220> FEATURE:
<221> NAME/KEY: modified_base
<222> LOCATION: (772)..(772)
<223> OTHER INFORMATION: a, c, t, g, unknown or other
<220> FEATURE:
<221> NAME/KEY: modified_base
<222> LOCATION: (775)..(775)
<223> OTHER INFORMATION: a, c, t, g, unknown or other
<220> FEATURE:
<221> NAME/KEY: modified_base
<222> LOCATION: (799)..(800)
<223> OTHER INFORMATION: a, c, t, g, unknown or other
<220> FEATURE:
<221> NAME/KEY: modified_base
<222> LOCATION: (808)..(808)
<223> OTHER INFORMATION: a, c, t, g, unknown or other
<220> FEATURE:
<221> NAME/KEY: modified_base -continued

```
<222> LOCATION: (830)..(830)
<223> OTHER INFORMATION: a, c, t, g, unknown or other
<220> FEATURE:
<221> NAME/KEY: modified_base
<222> LOCATION: (836)..(837)
<223> OTHER INFORMATION: a, c, t, g, unknown or other
<220> FEATURE:
<221> NAME/KEY: modified_base
<222> LOCATION: (852)..(853)
<223> OTHER INFORMATION: a, c, t, g, unknown or other
<220> FEATURE:
<221> NAME/KEY: modified_base
<222> LOCATION: (855)..(858)
<223> OTHER INFORMATION: a, c, t, g, unknown or other
<220> FEATURE:
<221> NAME/KEY: modified_base
<222> LOCATION: (872)..(872)
<223> OTHER INFORMATION: a, c, t, g, unknown or other
<220> FEATURE:
<221> NAME/KEY: modified_base
<222> LOCATION: (877)..(877)
<223> OTHER INFORMATION: a, c, t, g, unknown or other
<220> FEATURE:
<221> NAME/KEY: modified_base
<222> LOCATION: (882)..(882)
<223> OTHER INFORMATION: a, c, t, g, unknown or other
<220> FEATURE:
<221> NAME/KEY: modified_base
<222> LOCATION: (890)..(891)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (901)..(902)
<223> OTHER INFORMATION: a, c, t, g, unknown or other
<220> FEATURE:
<221> NAME/KEY: modified_base
<222> LOCATION: (904)..(904)
<223> OTHER INFORMATION: a, c, t, g, unknown or other
<220> FEATURE:
<221> NAME/KEY: modified_base
<222> LOCATION: (908)..(909)
<223> OTHER INFORMATION: a, c, t, g, unknown or other
<220> FEATURE:
<221> NAME/KEY: modified_base
<222> LOCATION: (920)..(920)
<223> OTHER INFORMATION: a, c, t, g, unknown or other
<220> FEATURE:
<221> NAME/KEY: modified_base
<222> LOCATION: (928)..(928)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (935)..(936)
<223> OTHER INFORMATION: a, c, t, g, unknown or other
<220> FEATURE:
<221> NAME/KEY: modified_base
<222> LOCATION: (938)..(939)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
```

```
<221> NAME/KEY: modified_base
<222> LOCATION: (953)..(953)
<223> OTHER INFORMATION: a, c, t, g, unknown or other
<220> FEATURE:
<221> NAME/KEY: modified_base
<222> LOCATION: (955)..(955)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (959)..(959)
<223> OTHER INFORMATION: a, c, t, g, unknown or other
<220> FEATURE:
<221> NAME/KEY: modified_base
<222> LOCATION: (964)..(965)
<223> OTHER INFORMATION: a, c, t, g, unknown or other
<220> FEATURE:
<221> NAME/KEY: modified_base
<222> LOCATION: (967)..(968)
<223> OTHER INFORMATION: a, c, t, g, unknown or other
<220> FEATURE:
<221> NAME/KEY: modified_base
<222> LOCATION: (970)..(970)
<223> OTHER INFORMATION: a, c, t, g, unknown or other
<220> FEATURE:
<221> NAME/KEY: modified_base
<222> LOCATION: (972)..(976)
<223> OTHER INFORMATION: a, c, t, g, unknown or other

<400> SEQUENCE: 21
gcnnntctat ttnnngagac agtcataatg aaatacctat tgcctacggc agccgctgga      60
ttgttattac tcgcggccca gccggccatg gcccaggtgc agctgtggag tctgggggag     120
gcgtggtcca gcctgggagg tccctgagac tctcctgtgc agcctctgga ttcaccttca     180
gtaactttgg catgcactgg gtctgccagg ctccaggcaa ggggctggag tgggtggcaa     240
ttatttcata tgatgcaagt agtgaatact atgcagactc cgtgaagggc cgattcacca     300
tctccagaga caattccagg aacactcttt atctgcaaat gaacagcctg agacctgagg     360
acacggctgt atattactgt gcgaagaagg acggtcggag tgggagctac tactactttg     420
actactgggg ccagggaacc ctggtcaccg tctcctcagg tggaggcggt tcaggcggag     480
gtggctctgg cggtggcgga tcggatgttg tgatgactca gtctccatcc tccctgtctg     540
catctgtagg agacagagtc accatcactt gccgggcgag tcaagatttt aggaattggt     600
tagcctggta tcaggtgaaa ccaggaaaag cccccaagcc cctgatctat ggtgcatcca     660
cttttgcaaaa tggggtccca tccaggttca gcggcagtgg gtctganaca gatttctctc     720
tcactatcag cagcctgcag cctgagnant ttgcaactta cttttgtcaa cnggntcaca     780
gtttccctcc cactttcgnn ggaggganac gactggagat taaacgtgcn gccgcnnaca     840
aaactcatct cnnannnntc tgaatggggc cncatanact gntgaaagtn nttancaaac     900
nncntacnna aaattcattn ctacgtcngg aanannanna antttanatn gtncncnant     960
atgnngnngn cnnnnna                                                    977
```

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22

```
ggcccagccg gcc                                                          13
```

<210> SEQ ID NO 23
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
ggcccagccg gccatggccc aggtgcagct ggtgcagtct ggggctgagg tgaagaagcc       60
tggggcctca gtgaaggtct cctgcaaggc ttctggttac acctttacc                  109
```

<210> SEQ ID NO 24
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
ggcccagccg gccatggccc aggtgcagct ggtgcagtct ggggaggcg tggtccagcc        60 tgggaggtcc ctgagactct cctgtgcagc ctctggattc accttcagt                  109
```

<210> SEQ ID NO 25
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ggcccagccg gccatggccc aggtacagct gcagcagtca ggctcaggac tggtgaagcc       60
ttcacagacc ctgtccctca cctgctctgt ctctggtgac tccatctcc                  109
```

<210> SEQ ID NO 26
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
ggcccagccg gccatggccc aggtgcagct gcaggagtcg gggccaggac tggtgaagcc       60
ttcggagacc ctgtccctcg tctgcactgt ctctggtggc tccctcagt                  109
```

<210> SEQ ID NO 27
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
ggcccagccg gccatggccc aggtgcagct ggtgcagtct ggagcagagg tgaaaaagcc       60
cgggcagtct ctgatgatct cctgtcaggg ttctggatac agctttagc                  109
```

<210> SEQ ID NO 28

```
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ggcccagccg gccatggccc aggtgcagct ggtgcagtct ggggcagagg tgaaaaagcc      60
cgggcagtct ctgaggatct cctgtaaggg tgctggatac agctttagc               109

<210> SEQ ID NO 29
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ggcccagccg gccatggccc aggtgcagct gcaggagtcg ggggaggcgt ggtccagcct      60
gggaggtccc tgagactctc ctgtgcagcg tctggattca ccttcagt                108

<210> SEQ ID NO 30
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ggcccagccg gccatggcca ggtgcagctg gtggagtctg ggggaggctt ggtacagcct      60 gggggtccc tgagactctc ctgtgcagcc tctggattca cctttagc                 108

<210> SEQ ID NO 31
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ggcccagccg gccatggccc aggtgcagct gtggagtctg ggggaggcgt ggtccagcct      60
gggaggtccc tgagactctc ctgtgcagcc tctggattca ccttcagt                108

<210> SEQ ID NO 32
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ggcccagccg gccatggccc aggtgcagct ggtgcgtctg gaggagactt gatccagcct      60
ggggggtccc tgagactctc ctgtgcagcc tctggattca cctttaat                108

<210> SEQ ID NO 33
<211> LENGTH: 108
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 33
ggcccagccg gccatggccc aggtgcagct gcaggagtcg ggggagacgt ggtccagcct      60
gggaggtccc tgagactctc ctgtgcagcc tctggattca ccttcagt                  108

<210> SEQ ID NO 34
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ggcccagccg gccatggccg agtgcagctg gtggagtctg ggctgaggt gacgaagcct       60 ggggcctcag taagggtctc ctgcaaggct tctggataca ccttcagc                  108

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atatatccat ggcccaggtg cagctgcagg agtctggggg aggcgtggtc c               51

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atatatccat ggcccaggtg cagctggtgg agtctggggg aggcttggta c               51

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccggccatg gcccaggtac agctgcagga gtctggggga ggcttggt                   48

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccgtgatgg tgatgatgat gtgcggccgc acgtttgatc tccag                      45

<210> SEQ ID NO 39
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Gln Ile Ile Asn Lys
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Gln Ile Val Tyr Lys
1               5

<210> SEQ ID NO 41
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(100)
<223> OTHER INFORMATION: This region may encompass 3-100 "Gly" residues
<220> FEATURE:
<221> NAME/KEY: misc_feature
<222> LOCATION: (102)..(201)
<223> OTHER INFORMATION: This region may encompass 3-100 "Gly" residues

<400> SEQUENCE: 41

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Pro Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190
```

Gly Gly Gly Gly Gly Gly Gly Gly Gly
        195                 200

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 43

Xaa Xaa Xaa Xaa Xaa Xaa Xaa Xaa Leu Xaa Xaa Lys Xaa Xaa Xaa Xaa
1               5                   10                  15

<210> SEQ ID NO 44
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(43)
<223> OTHER INFORMATION: Any amino acid
<220> FEATURE:
<221> NAME/KEY: MOD_RES
<222> LOCATION: (45)..(45)

<223> OTHER INFORMATION: Any amino acid

<400> SEQUENCE: 44

Ser Xaa Leu Xaa Asn Xaa Xaa Xaa Xaa Leu Leu Xaa Xaa Xaa Xaa
1               5                   10                  15

Xaa Asn Leu Xaa Xaa Xaa Leu Xaa Xaa Xaa Xaa Xaa Xaa Xaa Xaa
            20                  25                  30

Xaa Xaa Xaa Xaa Xaa Xaa Xaa Xaa Xaa Xaa Xaa Tyr Xaa
        35                  40                  45

<210> SEQ ID NO 45
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser
1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Leu Leu
1

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Pro Gly Gln Gln Trp Tyr Pro Ser
1               5

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any amino acid

<400> SEQUENCE: 48

Gly Ile Arg Arg Arg Asp Gln Ala Asp Arg Pro Arg Cys Gly Arg Arg
1               5                   10                  15

Thr Lys Thr His Leu Arg Arg Gly Ser Glu Trp Gly Arg Ile Xaa Cys
            20                  25                  30

<210> SEQ ID NO 49
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 49

Lys Leu Phe Xaa Xaa Thr Ser Tyr Xaa Lys Phe Ile Tyr
1               5                   10

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 50

Arg Leu Xaa Xaa Xaa Gln Thr Leu Xaa Arg Tyr Ala Asn Tyr Glu Gly
1               5                   10                  15

Cys Xaa Xaa Asn
            20
```

ANTIBODY BASED REAGENTS THAT SPECIFICALLY RECOGNIZE TOXIC OLIGOMERIC FORMS OF TAU

RELATED APPLICATION

This application claims priority under 35 U.S.C. 119(e) to provisional U.S. Ser. No. 61/713,441 filed Oct. 12, 2012, which application is incorporated hereby by reference.

BACKGROUND OF THE INVENTION

Numerous studies have implicated small soluble oligomeric aggregates of Aβ as toxic species in Alzheimer's disease (AD), and increasing evidence also implicates oligomeric forms of tau as having a direct role in disease pathogenesis of AD and other tauopathies such as Frontotemporal Dementia (FTD). As the focus of Aβ studies has slowly shifted toward soluble Aβ species and mechanisms, new reagents were needed that could specifically identify the variety of different aggregate species present. Indeed, many contradictory studies on the role of Aβ aggregation in AD were reported and progress impeded because suitably selective reagents were not available to characterize the aggregate species present. Increasing evidence from cell and animal models indicate that oligomeric rather than fibrillar forms of tau are toxic and correlate with neuronal degeneration, therefore well characterized reagents that can specifically recognize the diversity of tau morphologies present in the human brain are critically needed to facilitate studies to identify the most promising tau species for use as biomarkers of disease and to study toxic mechanisms.

The microtubule associating protein tau is a major component of the neurofibrillary tangles associated with AD and tauopathies that are characterized by hyperphosphorylation and aggregation of tau. Tau plays an important role in assembly and stabilization of microtubules. Tau is a natively unfolded protein, and similar to a number of other natively unfolded proteins, it can aberrantly fold into various aggregate morphologies including β-sheet rich fibrillar forms. The different types of post-translational modifications of tau in AD include phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Tau can be modified by phosphorylation or by reactive nitrogen and oxygen species among others. Elevated total tau concentration in CSF has been correlated with AD, as has the presence of various phosphorylated tau forms, and the ratio of tau to Aβ42. Reactive nitrogen and oxygen can modify tau facilitating formation of aggregate forms including oligomeric species. Levels of oligomeric tau have also been implicated as a potential early diagnostic for AD. Therefore, determination of total tau, phosphorylated tau and oligomeric tau concentrations all have potential value as diagnostics for neurodegenerative diseases including tauopathies and AD.

Tau is an intrinsically unstructured protein due to its very low hydrophobic content containing a projection domain, a basic proline-rich region, and an assembly domain. Hexapeptide motifs in repeat regions of tau give the protein a propensity to form β-sheet structures which facilitate interaction with tubulin to form microtubules as well as selfinteraction to form pathological aggregates such as paired helical filaments (PHF). Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of the second, third and tenth exons of tau results in six tau isoforms of varying length in the CNS. The assembly domain in the carboxylterminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, whereas only 3R tau is expressed at the fetal stage. In tauopathies, mutations altering the splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of Aβ. While NFTs have been implicated in mediating neurodegeneration in AD and tauopathies, animal models of tauopathy have shown that memory impairment and neuron loss do not associate well with accumulation of NFT. Animal studies showed improvement in memory and reduction in neuron loss despite the accumulation of NFTs, a regional dissociation of neuron loss and NFT pathology, and hippocampal synapse loss and dysfunction and microglial activation months before the accumulation of filamentous tau inclusions. The pathological structures of tau most closely associated with AD progression are tau oligomers. All these studies suggest that tau tangles are not acutely neurotoxic, but rather that pretangle oligomeric tau species are responsible for the neurodegenerative phenotype, similar to toxic role of oligomeric Aβ species.

Numerous studies suggest that extracellular tau species contribute to neurotoxicity through an "infectious" model of disease progression. For example, tau pathology spreads contiguously throughout the brain from early to late stage disease, extracellular tau aggregates can propagate tau misfolding from the outside to the inside of a cell, brain extract from a transgenic mouse with aggregated mutant human tau transmits tau pathology throughout the brain in mice expressing normal human tau, induction of pro-aggregation human tau induces formation of tau aggregates and tangles composed of both human and normal murine tau (coaggregation), and levels of tau rise in CSF in AD, whereas Aβ levels decrease. A receptor-mediated mechanism for the spread of tau pathology by extracellular tau has been described.

Collectively, these studies all indicate that aggregated oligomeric species of tau, both intracellular and extracellular are vitally important in AD and other tauopathies. In order to more clearly define the role of individual tau forms in disease, there is a critical need to develop a series of well-defined reagents that selectively recognize individual target morphologies, and to use these reagents to identify which tau forms are the best biomarkers for AD, which forms are involved in toxicity both intra- and extracellularly, and which forms in brain tissue and CSF samples can distinguish between healthy and AD patients.

Therefore, reagents that can specifically target tau oligomers would be valuable tools for diagnostic and therapeutic applications for AD, frontotemporal dementia, other tauopathies and neurodegeneration following traumatic brain injury.

Accordingly, there exists the need for new therapies and reagents for the treatment of Alzheimer's disease, frontotemporal dementia, other tauopathies and neurodegeneration following traumatic brain injury, in particular, therapies and reagents capable of effecting a therapeutic and diagnostic benefit at physiologic (e.g., non-toxic) doses.

SUMMARY OF THE INVENTION

The present invention discloses an antibody or antibody fragment that specifically recognizes oligomeric tau but does not bind monomeric tau, fibrillar tau or non-disease associated forms of tau. As used herein, the phrase "specifically recognizes oligomeric tau" indicates that it does not bind to or recognize non-specific proteins. As used herein, the term "antibody" includes scFv (also called a "nanobody"), humanized, fully human or chimeric antibodies, single-chain antibodies, diabodies, and antigen-binding fragments of antibodies (e.g., Fab fragments). As used herein, the term "oligomer" refers to a dimer, trimer, tetramer, pentamer, hexamer, heptamer, octamer, nonamer, decamer, undecamer or dodecamer. Accordingly, in certain embodiments, the oligomeric tau is dimeric tau, trimeric tau, tetrameric tau, pentameric tau, hexameric tau, heptameric tau, octameric tau, nonameric tau, decameric tau, undecameric tau or dodecameric tau. In certain embodiments, the oligomeric tau is dimeric tau or trimeric tau. In certain embodiments, the oligomeric tau is trimeric tau. In certain embodiments, the oligomer is soluble.

In certain embodiments, the antibody fragment does not contain the constant domain region of an antibody.

In certain embodiments, the antibody fragment is less than 500 amino acids in length, such as between 200-450 amino acids in length, or less than 400 amino acids in length.

Certain embodiments of the invention provide an antibody fragment comprising amino acid sequence SEQ ID NO:1, SEQ ID NO:9, SEQ ID NO:11, SEQ ID NO:13, SEQ ID NO:15, SEQ ID NO:17, or SEQ ID NO:19. In certain embodiments, the antibody fragment comprises amino acid sequence SEQ ID NO:1, SEQ ID NO:9 or SEQ ID NO:11.

Certain embodiments of the invention provide a binding molecule that binds to oligomeric tau and does not bind monomeric tau, fibrillar tau or non-disease associated forms of tau, wherein the binding molecule comprises the sequence of SEQ ID NO:1, SEQ ID NO:9, SEQ ID NO:11, SEQ ID NO:13, SEQ ID NO:15, SEQ ID NO:17, or SEQ ID NO:19. In certain embodiments, the binding molecule comprises the sequence of SEQ ID NO:1, SEQ ID NO:9, or SEQ ID NO:11.

Certain embodiments of the invention provide an antibody or antibody fragment as described herein, wherein said antibody fragment is isolated according to a method comprising the steps of:

a. a negative panning of a scFV phage library wherein said negative panning eliminates phage that bind to non-desired antigens wherein said negative panning comprises serially contacting phage with:
   a generic protein; and
   (ii) mononeric forms of tau;
   and monitoring the binding of said phage to the generic protein and monomeric forms of tau using Atomic Force Microscope (AFM) Imaging and repeating steps (i) and (ii) until no phage is observed binding to antigen by said AFM imaging to produce an aliquot of phage that does not bind to monomeric tau, fibrillar tau, or non-disease associated forms of tau;

b. contacting the aliquot of phage that does not bind to monomeric tau, fibrillar tau, or non-disease associated forms of tau with tau oligomers and incubating for time sufficient to allow binding of phage to said oligomers; and c. eluting the bound phage particles from step (b).

Certain embodiments of the invention provide an antibody or antibody fragment isolated according to a method comprising the steps of:

(a) negative panning a scFV phage library comprising serially contacting phage with:
   a generic protein; and
   (ii) mononeric forms of tau;
   and until less than 5% of the phage is observed binding to antigen, which produces an aliquot of phage that does not bind to monomeric tau, fibrillar tau or non-disease associated forms of tau;

(b) positive panning of the aliquot from step (a) comprising contacting the aliquot of phage from step (a) with tau oligomers, and incubating for time sufficient to allow binding of phage to said brain derived tau oligomers; and (c) eluting the bound phage particles from step (b).

In certain embodiments, the tau oligomer used in the positive panning is trimeric tau 4N1R.

In certain embodiments, the generic protein is bovine serum albumin (BSA).

In certain embodiments, the negative panning further comprises serially contacting phage with brain derived control samples that do not contain oligomeric tau.

In certain embodiments, the observing of the binding of the phage to the antigen is by using Atomic Force Microscope (AFM) Imaging. In certain embodiments, the negative panning is repeated until less than 0-10% phage was observed by AFM imaging as binding to antigen in step (a).

Certain embodiments of the invention provide a method of inhibiting the aggregation of tau comprising contacting a composition that comprises tau monomers with an antibody, antibody fragment or binding molecule as described herein. In certain embodiments, the aggregation of tau is in a cell. In certain embodiments, the aggregation of tau is in brain tissue. In certain embodiments, the contacting with an antibody, antibody fragment or binding molecule decreases the rate of formation of tau aggregates as compared to said rate in the absence of composition or binding molecule.

Certain embodiments of the invention provide a method of detecting the presence of tau in a physiological sample comprising contacting a sample with an antibody, antibody fragment or a binding molecule as described herein and determining the binding of said composition with said tissue sample wherein binding of said composition to said tissue sample is indicative of the presence of tau oligomers in said tissue sample wherein said presence of said tau oligomers is indicative of early stage AD, frontotemporal dementia, other tauopathies or neurodegeneration following traumatic brain injury. In certain embodiments, the physiological sample is brain tissue, serum, cerebrospinal fluid (CSF), blood, urine or saliva.

Certain embodiments of the invention provide a method of preventing or inhibiting the accumulation of tau in the brain of a mammal comprising administering to said mammal a composition comprising an antibody fragment or a binding molecule as described herein.

BRIEF DESCRIPTION OF THE DRAWINGS

FIG. 1. Height distribution analysis of various tau samples obtained from AFM images. AD Tau #1 and AD Tau #3 represent tau samples obtained purified from AD brain tissue. Tau412M and Tau441M represent monomeric samples of 3R (tau 412) and 4R (tau 412) tau samples. Tau 4410 represents and oligomeric sample of tau441. Differences in height and oligomeric state between samples are readily detected.

Figure 2A:
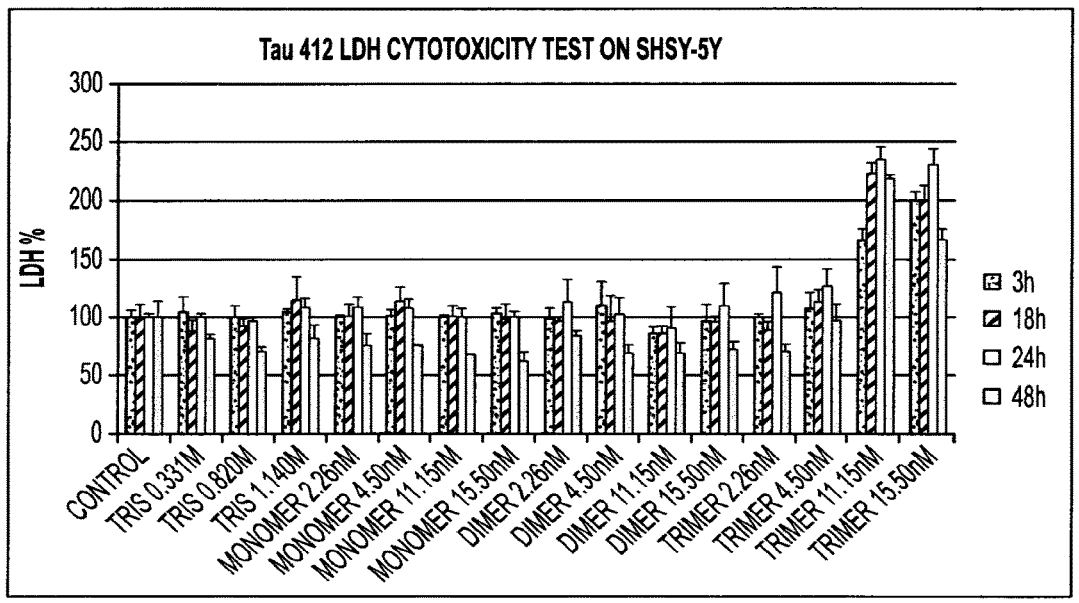
Figure 2B:
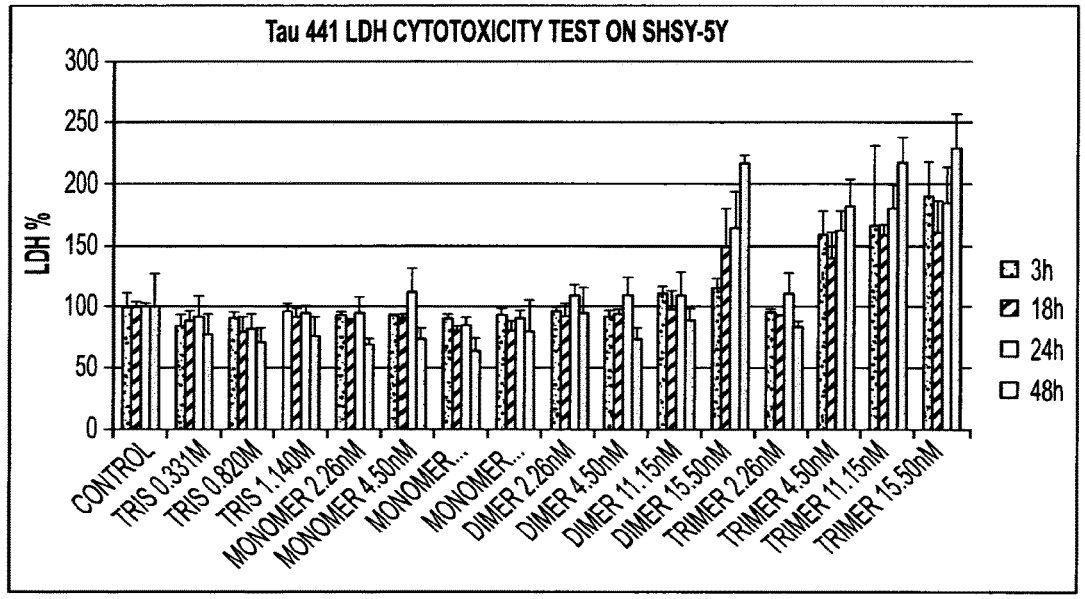

FIGS. 2A and 2B. Lactate dehydrogenase (LDH) test of various tau species on SHSY-5Y human neuroblastoma cells. (A) Toxicity of monomeric, dimeric and trimeric tau 1N4R (aka. tau 412) towards SHSY-5Y cells. (B) Toxicity of monomeric, dimeric and trimeric tau 2N4R (aka. tau 441) towards SHSY-5Y cells. In both (A) and (B), for each group from left to right, the first bar is 3 h, the second bar is 18 h, the third bar is 24 h and the fourth bar is 48 h.

FIGS. 3A, 3B and 3C. (A) F9T scFv amino acid sequence. (B) Comparison of the DNA sequence for F9 scFv (before repair) and F9T-7 scFv (after repair). (C) DNA sequences for F9T, F9, F9T-7L and F9T-7F-RC.

FIGS. 4A, 4B, 4C, 4D, 4E and 4F. DNA sequences from six scFv clones specific for trimeric tau (top) and corresponding amino acid sequences (bottom), including (A) F9T; (B) D11C; (C) D4G; (D) G12C; (E) H2A; and (F) H7T.

FIGS. 5A and 5B. (A) DNA sequences for C6T, F9T, D11C, D4G, G12C, H2, H2A and H7T. (B) Comparison of the DNA sequences for C6T, F9T, D11C, D4G, G12C, H2, H2A and H7T.

Figure 6A:
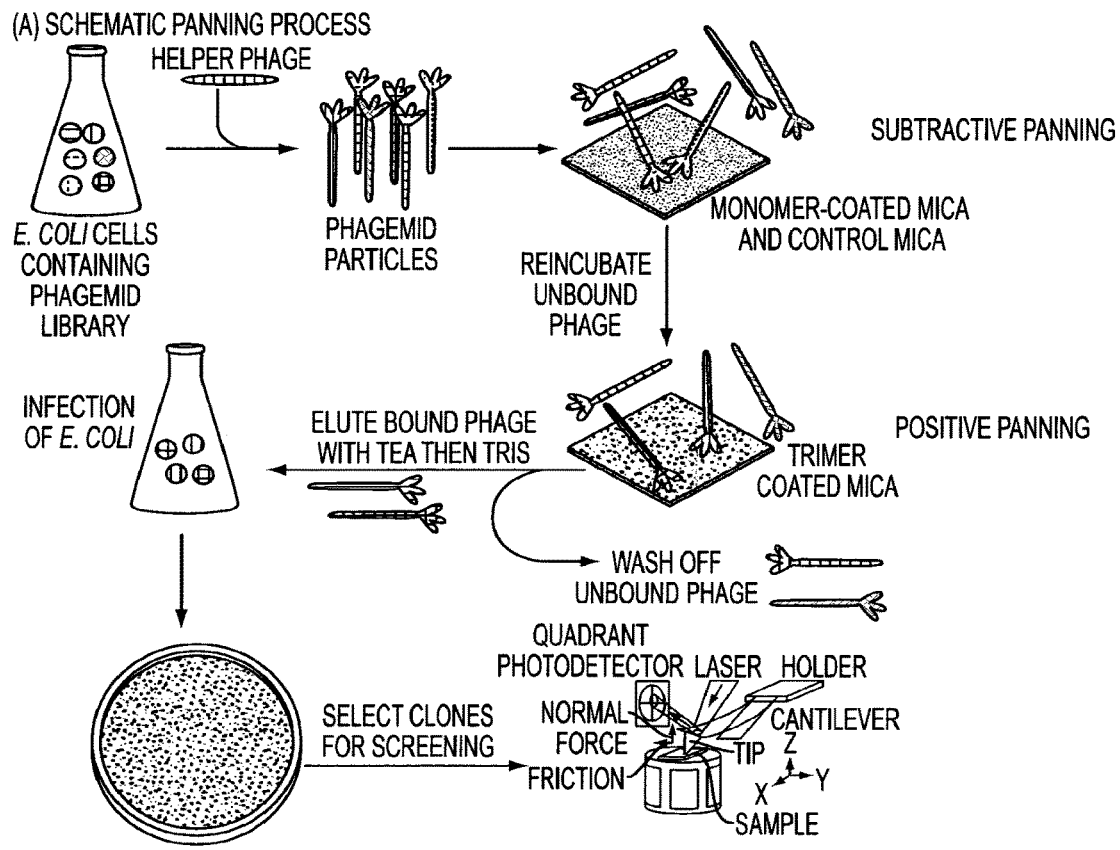
Figure 6B:
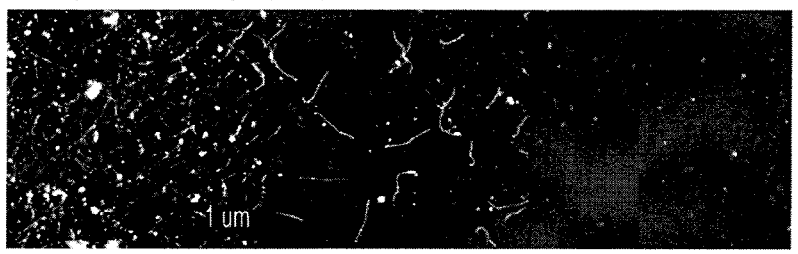
Figure 6C:
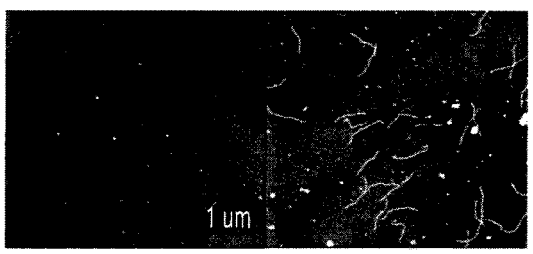

FIGS. 6A, 6B and 6C. The novel biopanning process combines subtractive panning and positive panning from phagemid scFv library and the single cloning screening using AFM. (A) Schematic panning process, in which the mica carrier can be replaced by immunotubes for bulk amount of non-desired antigen such as BSA for rapid removal of irrelevant phage particles, especially during subtractive panning. (B) Subtractive panning against BSA performed to eliminate non-specific phage. Left, middle and right images are the phage pool affinity check after BSA tube #1, #3 and #5 respectively. The absence of phage binding in the right-handed side image denotes the accomplishment of subtractive panning against BSA. The scale bar of 1 .mu.m applies to all three images. (C) Positive panning against tau trimer was performed and imaged with AFM. A duplicate of positive panning compared with pure desired antigen proves that the antigen is free of phage and the phage pool depleted of non-desired antigen binders still contains phage that specifically binds to desired antigen. Left image is the purified trimeric tau 1N4R immobilized on mica; Right image is the same piece of mica on which the remaining phage pool of subtractive panning was deposited and non-binding particles were washed off. The scale bar of 1 μm applies to both images.

Figure 7:
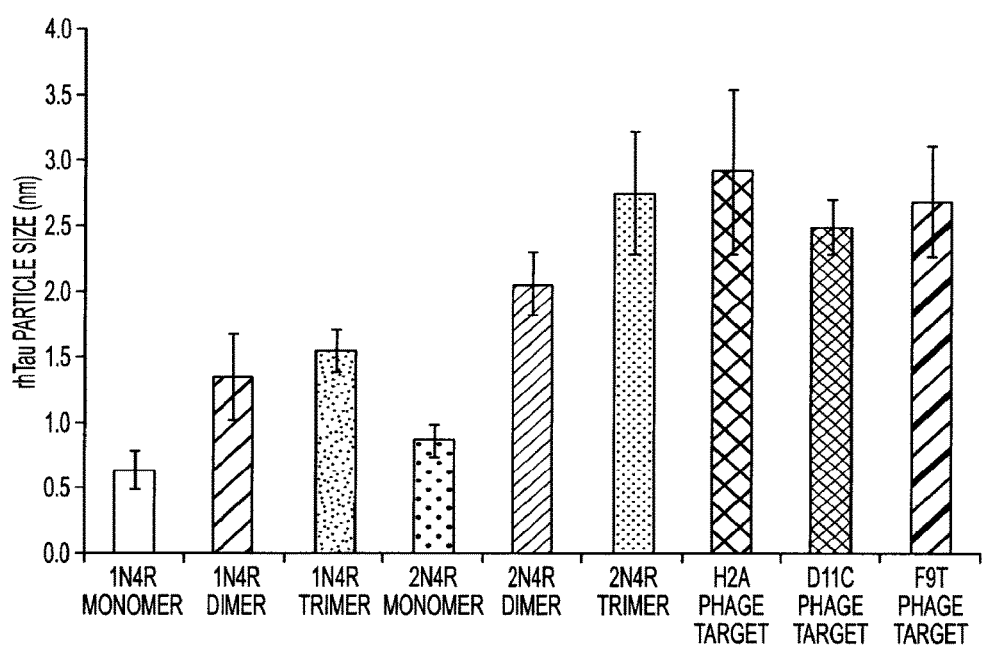

FIG. 7. Particle size analysis of oligomeric tau captured by single clone scFv-displayed phage from rhTau 2N4R mixed aggregates. Size of clone phage targets compared with those of purified rhTau monomer, dimer and trimer. Individual particle capturing a phage was measured the size by section function in Nanoscope Analysis. The mean value of each clone phage target falls in between 2.5 nm and 3.0 nm, in accordance with rhTau 2N4R trimer size range. (Error bar:+/−standard deviation)

Figure 8:
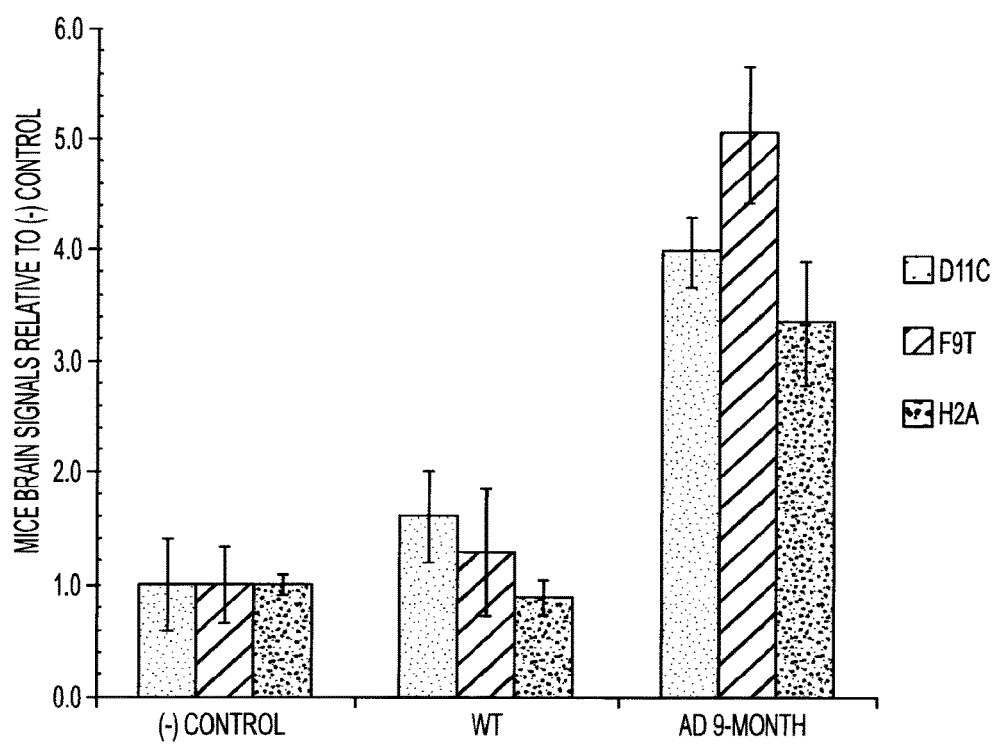

FIG. 8. Three clones, F9T, D11C and H2A in scFv form recognize and retain from 9-month 3×TG-AD mice hippocampus abnormal phosphorylated tau species that are immunoreactive with AT8. Negative control is PBS as the target analyte and set as 1.0 to be used as normalization standards. Signals lower than 2.0 are recorded as negative while signals above 2.0 are recorded as positive. (Error bar:+/−standard deviation)

Figure 9:
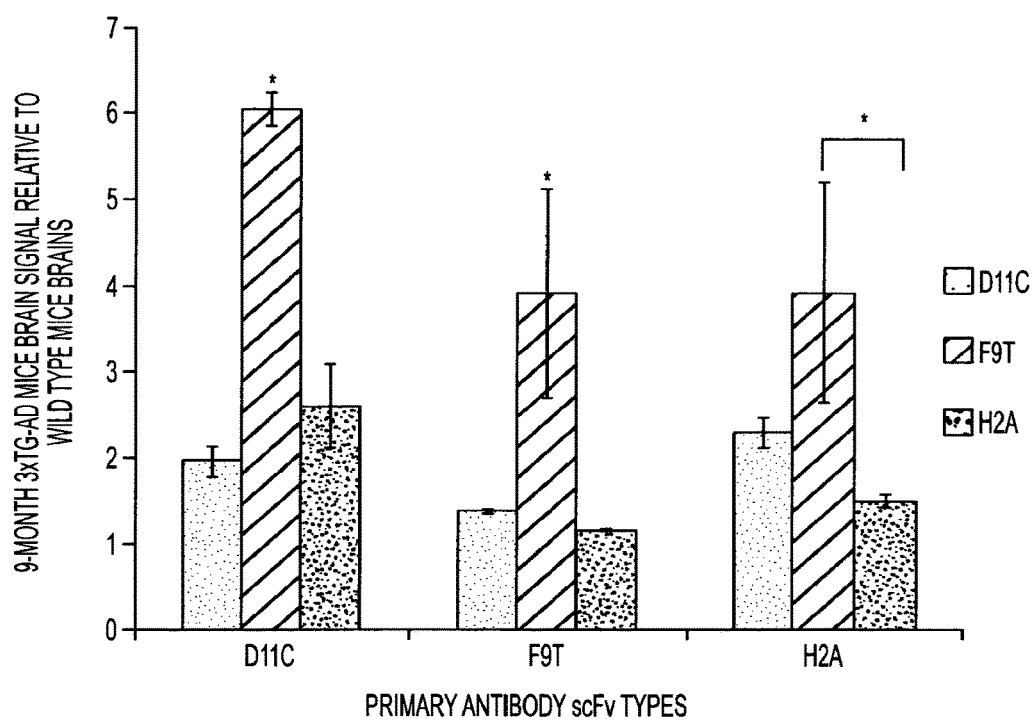

FIG. 9. The comparison of secondary antibody affinity to 9-month 3×TG-AD mice brain extracts captured by three types of primary antibody scFv. The mean comparison was performed within each group of the same primary antibody. (Error bar:+/−standard deviation)

Figure 10:
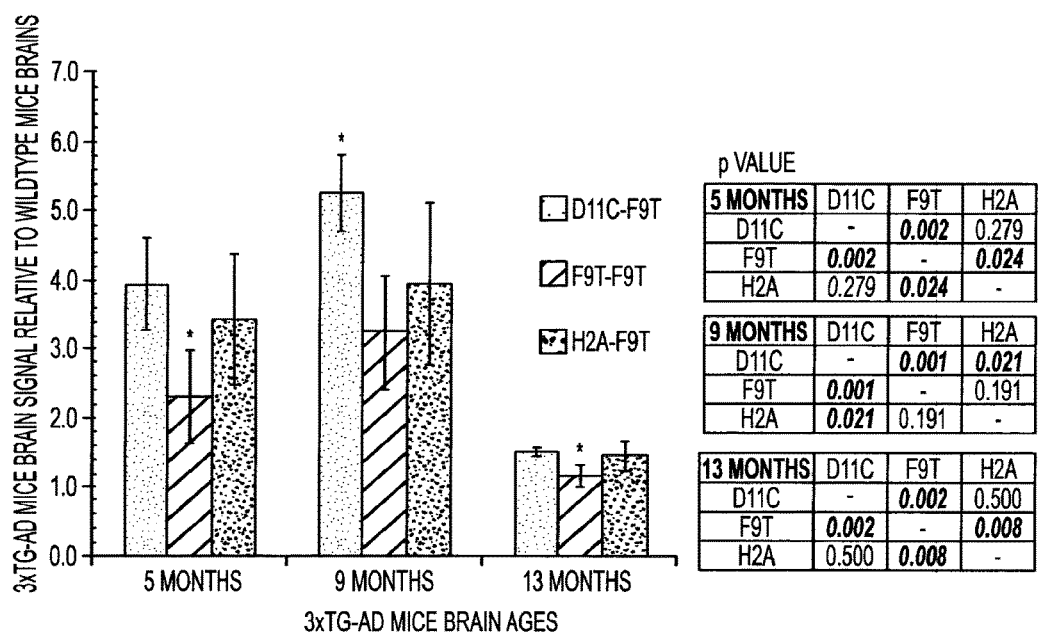

FIG. 10. Oligomeric tau targeted scFv clones (F9T, D11C and H2A) affinity to different 3×TG-AD mice brain extracts detected by F9T scFv-phage. Two mice for each age were tested in triplicates. The data were grouped by the mice ages. The mean comparison was performed within each group of the same mice age. (Error bar:+/−standard deviation)

Figure 11A:
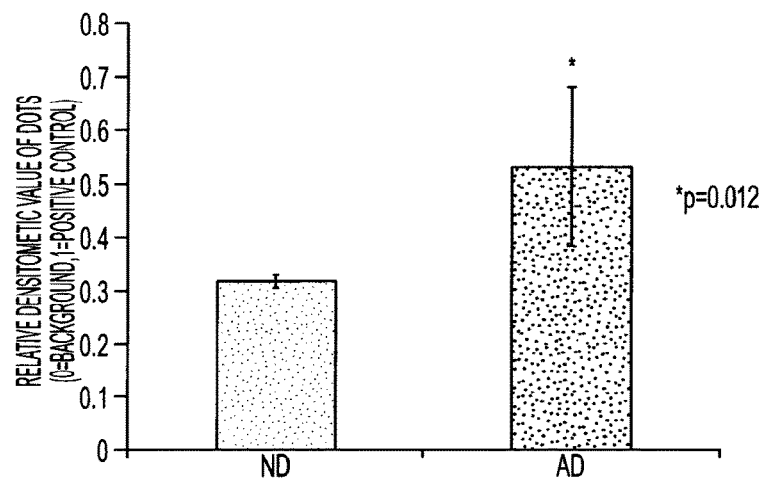
Figure 11B:
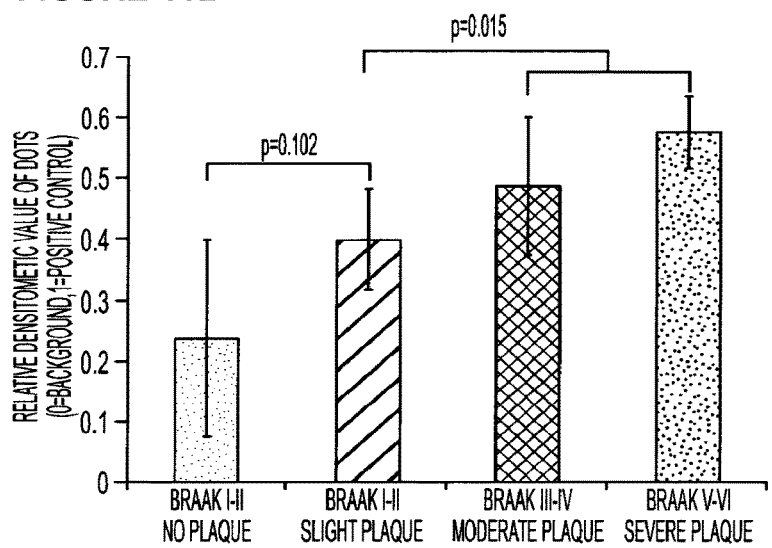
Figure 11C:
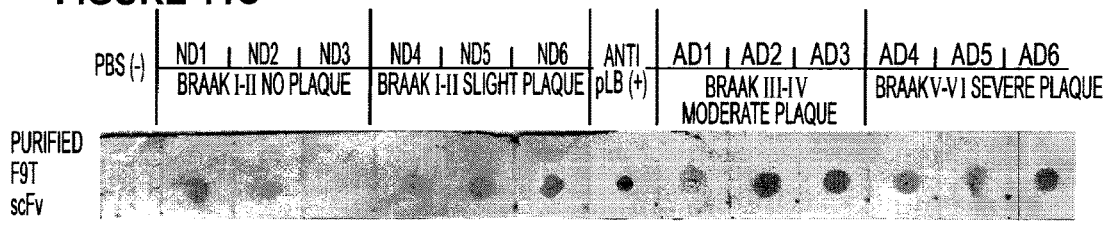

FIGS. 11A, 11B and 11C. Densitometric analysis of dot blot reactivity of F9T scFv with brain homogenates from age-matched human middle temporal gyrus (MTG). Densitometric value of dots signal is based on a scale of 0 to 1, with 0 equals the background signal and 1 equals the positive signal of anti-pLB scFv dots. Statistical analysis is performed in one-way ANOVA comparing means of two groups. (A) compares patients grouped by antemortem diagnosis as non-demented (ND) and Alzheimer's (AD). That AD group means is different from ND group mean (p<0.05) signifies F9T scFv can detect AD from ND. (B) compares patients grouped by postmortem examination results defined by Braak stages and neuritic plaque frequencies directly implying the AD progression. Braak stages I-II (early stage) were both diagnosed as non-demented but half of the cases bear slight plaque compare with the other half without plaques. Braak stages III-IV (AD middle stages) display moderate plaques while Braak stages V-VI (AD late stages) display severe plaques. F9T scFv affinity to these MTG extracts directly correlates with their AD progression defined by Braak stages and plaque frequency. (C) Sample dot blot affinity test of purified F9T scFv on homogenized MTG tissue from non-demented and Alzheimer's patients.

FIG. 12. DNA sequences of the starting region and the first heavy chain framework region (HCFR1) of selected scFvs from Sheets' library and standard scFvs from the generic library from which Sheets' was developed. F9, H7, D4, D11 and G12 are five scFvs selected targeting rhTau 1N4R trimer, the rest are standard scFvs. Except for one missing base pair for each clone causing frame shift, all these scFvs from Sheets' library contain the similar FR regions as those from the generic library. All of these missing base pairs (highlighted in dark background) lie either at the beginning of HCFR1 or the connection of HCFR1 and the methionine start codon unaffecting the restriction site NcoI, scFv expression initiation or any complementarity-determining regions (CDRs). Inserting the missing base pair retaining the amino acid sequences of selected clones sequences in generic library enables these clones to express soluble scFv without interfering their epitope-binding sites, thus maintain their specificities.

FIG. 13. Designed primers for clone sequence revision. Forward primers contain NcoI (5'-CCATGG-3' in italic) upstream of scFv sequence and the missing base pair (underlined). The reverse primer includes NotI (5'-GCGGCCGC-3' in italic) downstream of scFv sequence. By performing a polymerase chain reaction using the paired primers and corresponding clone DNA template, revised clone scFv DNA fragments can be produced up to $2^{30}$ copies for subcloning into E. coli and producing scFv and phage.

Figure 14:
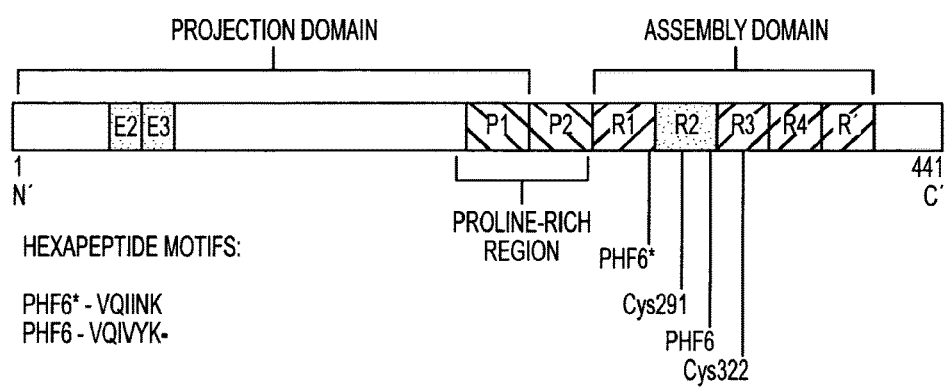

FIG. 14: Tau protein structural features in linear diagram. A full-length tau protein with 441 amino acids (tau441 or tau 2N4R) is shown. Alternative splicing showed in yellow rectangles results in a total of six isoforms, denoted by either their total number of amino acids or the number of N'-terminal exons (Ns) and microtubule-associated repeats (Rs).

Figure 15:
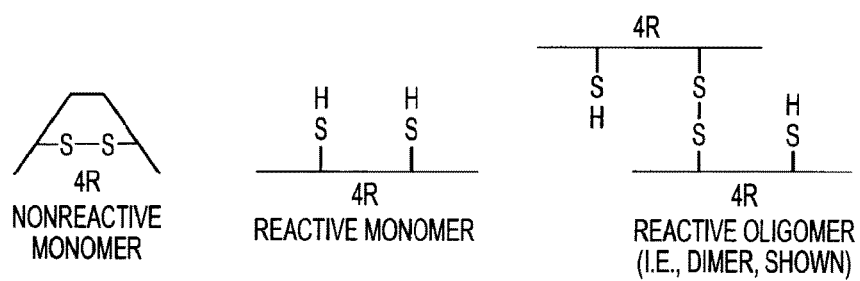

FIG. 15. Schematic of nonreactive monomer, reactive monomer, and reactive oligomer. Reactivity implies the ability to form an intermolecular disulfide linkage. Intramolecular disulfide linkage causes formation of nonreactive tau monomer. The free thiols in a reactive monomer allow formation of an intermolecular or intramolecular disulfide linkage. Reactive oligomer has one or more free thiols readily forming disulfide linkage with reactive monomeric tau for the oligomer extension purpose.

Figure 16B:
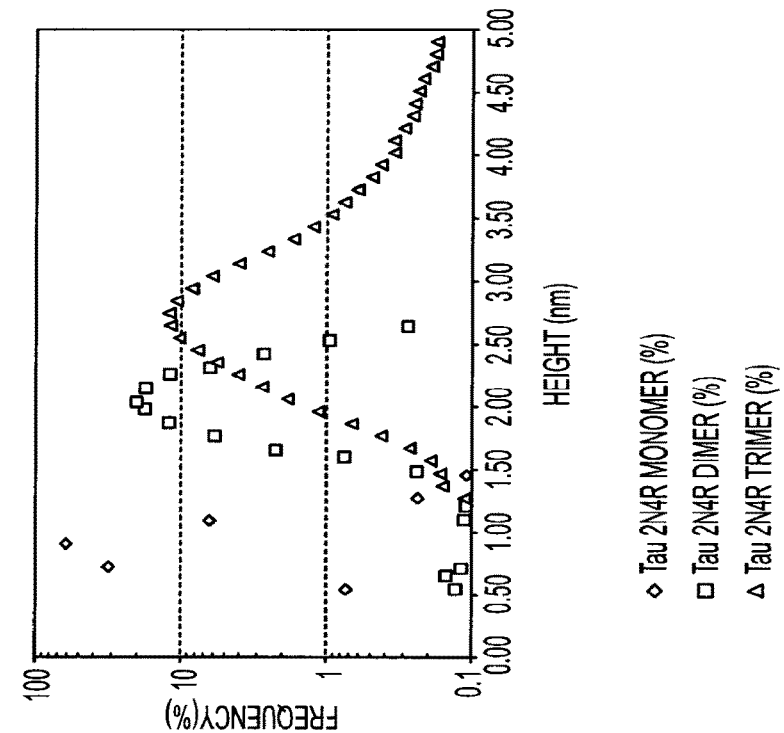
Figure 16A:
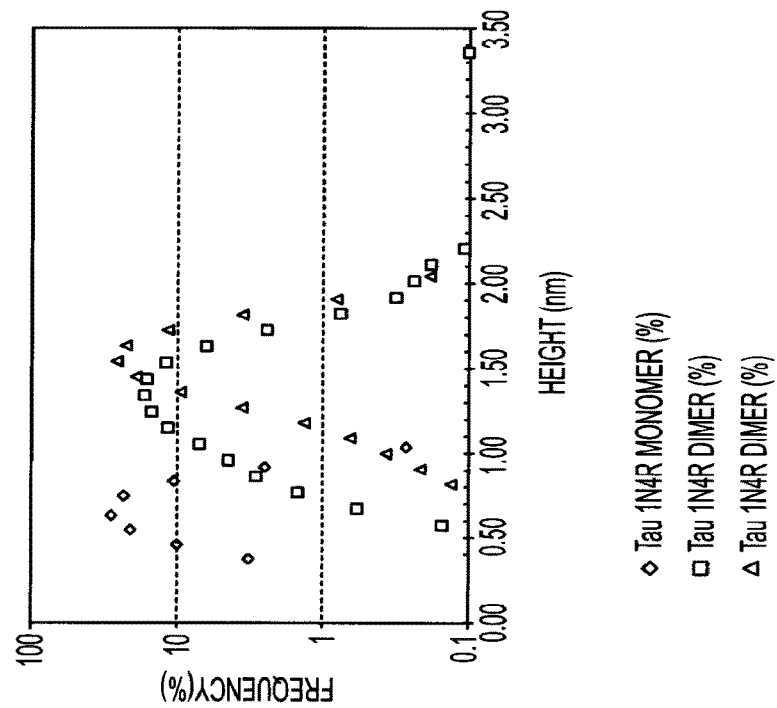

FIGS. 16A and 16B. Plots of height distribution of monomeric, dimeric, and trimeric fractions of rhTau 1N4R (a) and tau 2N4R (b). The height value of each particle was measured using Gwyddion. The numbers of particles falling in continuous size ranges were calculated and normalized into count percentages. The peak values give an approximate value for each tau species particle size. As expected, high-degree oligomers are larger than low-degree oligomers within the same isoform, and corresponding oligomeric aggregates from the longer isoform are larger than aggregates from the shorter isoform.

Figure 17A:
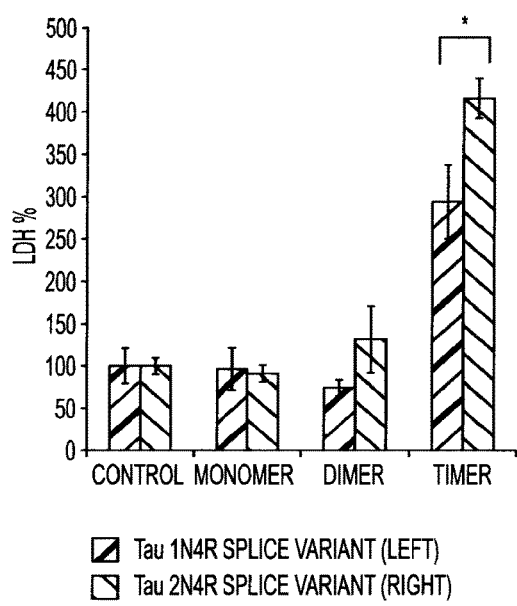
Figure 17B:
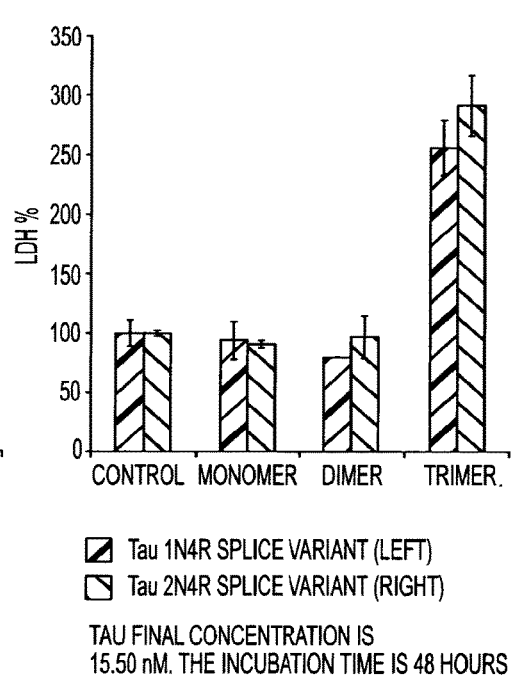
Figure 18A:
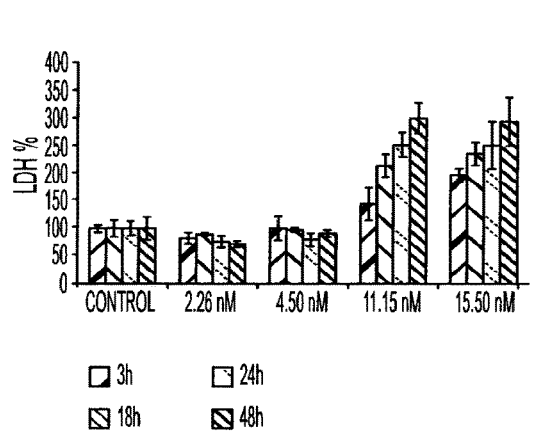
Figure 18B:
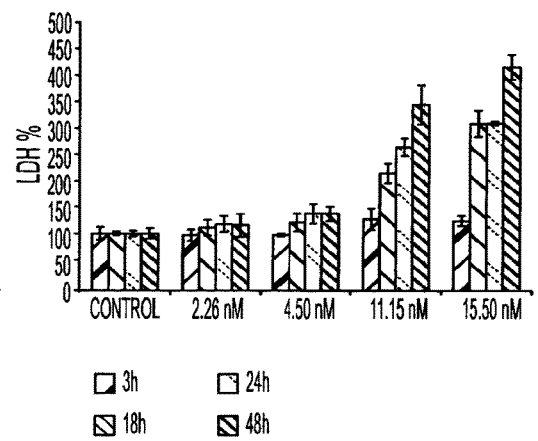
Figure 18C:
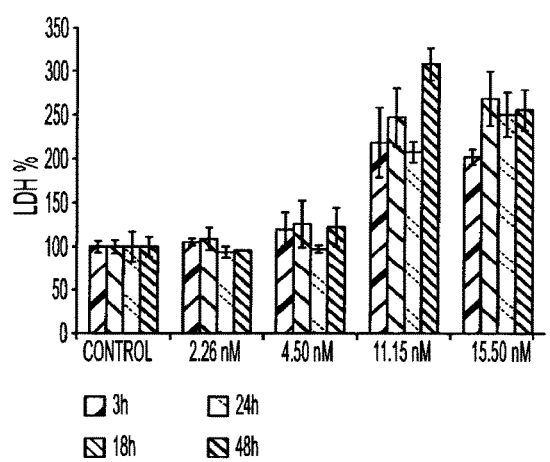
Figure 18D:
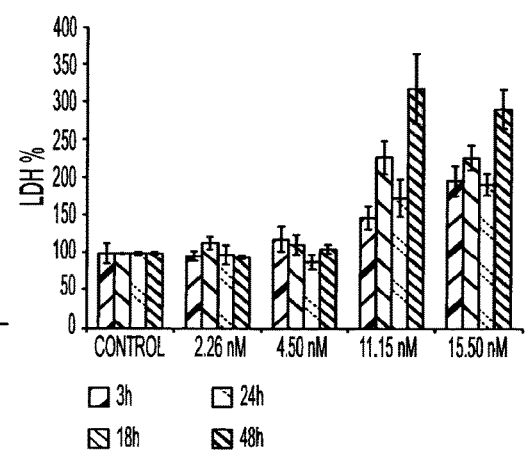

FIGS. 17A and 17B. Neurotoxicity of extracellular 15.5 nM monomeric, dimeric, and trimeric forms of 1N4R and 2N4R tau variants toward (a) nondifferentiated human neuroblastoma cells (SH-SY5Y) and (b) Retinoic-acid-differentiated SH-SY5Y cells was measured after 48-hour incubation using an LDH assay. For both four-repeat tau isoforms, trimeric form is more neurotoxic than monomeric and dimeric forms ($P<0.001$) on either neuron type. Full-length trimeric rhTau is more neurotoxic than 1N4R trimeric rhTau. ($P<0.05$).

FIGS. 18A, 18B, 18C and 18D. Time and concentration dependence of neurotoxicity induced by trimeric rhTau (1N4R and 2N4R) toward neuroblastoma cells measured by LDH assay. Nondifferentiated SH-SY5Y cells incubated with (a) 1N4R tau and (b) 2N4R tau; retinoic-acid-differentiated SHSY5Y cells incubated with (c) 1N4R tau and (d) 2N4R tau.

FIGS. 19A and 19B. Comparison of rhTau induced neurotoxicity toward nondifferentiated SH-SY5Y cells and retinoic-acid-(RA-) differentiated SHSY5Y cells. The data combine toxicity results of 15.5 nM monomeric, dimeric, and trimeric forms of both 1N4R and 2N4R tau variants. (a) After 3 hours-incubation, RA-differentiated SH-SY5Y cells are more vulnerable to extracellular trimeric rhTau toxicity than nondifferentiated SHSY-5Y cells are ($P<0.05$). (b) After 48-hours incubation, nondifferentiated SH-SY5Y cells are more vulnerable to extracellular trimeric rhTau toxicity than RA-differentiated SH-SY5Y cells ($P<0.05$).

DETAILED DESCRIPTION OF THE INVENTION

Tau is a protein involved in microtubule function in the brain. Aggregation of tau can lead to neuronal damage and dementia and traumatic brain injury. Increasing evidence suggests that small soluble oligomeric aggregate forms of tau may be the toxic species rather than the large fibrillar aggregates found during autopsies. Developing reagents against these species represents a potential therapeutic option. In the present invention, using a bio-panning protocol to identify single chain antibody fragments (scFv, also called nanobodies) against low (pico-molar) quantities of tau oligomers, the inventors identified binding reagents with therapeutic and diagnostic properties. Specifically, the inventors have generated single chain antibody fragments (scFvs or nanobodies) that selectively recognize oligomeric forms of the protein tau. These isolated scFvs that have potential value as diagnostics, therapeutics and imaging agents for neurodegeneration. As diagnostics, these antibody fragments can be used to detect the presence of oligomeric tau in serum, CSF or other fluid samples as a presymptomatic indication of neurodegeneration. Oligomeric tau may be an early indicator of Alzheimer's disease, frontotemporal dementia, other tauopathies and of neurodegeneration following traumatic brain injury. The antibody fragments can also be used as therapeutics to selectively target the toxic oligomeric tau aggregates protecting neurons from damage. Finally, the reagents can also be used as imaging agents to detect the presence of tau aggregates and neurodegeneration in vivo. The antibody fragments can be readily labeled for PET scans or other imaging techniques.

The biopanning studies were performed to isolate single chain variable fragments (nanobodies) against the different tau species. The biopanning protocol that was used combines the imaging capabilities of AFM with the binding diversity of phage-displayed antibody technology. To isolate nanobodies against specific oligomeric morphologies of a target protein, the protocol was modified to include negative panning steps to remove clones that bind to non-desired protein forms. To isolate nanobodies against oligomeric tau two negative panning steps were incorporated. In the first negative panning step, all non-specific "sticky" clones were removed by panning against a generic protein, bovine serum albumin (BSA). In the second negative panning step, all clones that bind to the non-desired monomeric form of tau were removed. A sample of pure monomeric tau was obtained for the negative panning to remove phage clones binding monomeric tau, and then aliquots of the remaining phage were used to screen for dimeric and trimeric specific clones respectively. Since it was found that the trimeric tau species was much more toxic to human neuronal cell lines than monomeric or dimeric, the inventors focused efforts on isolating phage clones that were selective for trimeric tau 4N1R. After negative panning against BSA and monomeric tau, ~100 clones were obtained from the positive selection against trimeric tau 4N1R. Each phage clone was screened by AFM for binding to the different tau species. Each phage sample was coincubated with monomeric, dimeric and trimeric tau samples which had been previously fixed to a mica substrate. Unbound phage was removed by excess stringent rinsing and remaining bound phage were imaged by AFM. After screening all 100 clones in this manner, clones that selectively bound either dimeric or trimeric tau, but not monomeric tau, were identified. After screening all 100 phage clones, 6 clones were selected for further study based on highest specificity for trimeric tau.

The DNA sequence of each of the six clones was validated to ensure that a full length scFv was encoded. In each of the six cases a single base pair was missing at the beginning of the coding sequence. In order to produce soluble scFv for further characterization, it was necessary to correct the frame shift to enable efficient expression of the scFv. DNA and amino acid sequences of the clones are shown in FIGS. 3-5. Specifically, the amino acid sequences of the 6 selected cloned scFvs are: F9T (SEQ ID NO:1), F9T (SEQ ID NO:9), D11C (SEQ ID NO:11), D4G (SEQ ID NO:13), G12C (SEQ ID NO:15), H2A (SEQ ID NO:17), or H7T (SEQ ID NO:19). DNA sequences are also included in FIGS. 3-5.

The corrected F9 clone, F9T, expressed at very high levels, purified readily and maintained high specificity for oligomer tau over monomeric tau and fibril tau in the phage form viewed by AFM, so this clone was selected for further study. The D11 clone was also identified as selectively binding to trimeric but not monomeric tau. Both clones also selectively recognize tau aggregates in post-mortem human brain tissue containing tau tangles but not in age matched normal tissue, although with slightly different reactivity profiles. Therefore both F9T and D11C nanobodies have promise as therapeutics to block neuronal toxicity induced by naturally occurring aggregates of tau following TBI.

In a broad sense the scFv compositions of the present invention (e.g., the F9T and D11C) may be described as compounds that are tau binding compounds. These compounds may therefore be used in diagnostic as well therapeutic applications and may be either administered to patients or used on patient tissue samples. In some embodiments, the compositions of the present invention may be used for in vivo imaging of tau, and distinguish between neurological tissue with toxic tau forms and normal neurological tissue. As such the nanobody compositions of the invention may be used to detect and quantitate tau oligomers in diseases including, for example, Alzheimer's Disease, frontotemporal dementia, other tauopathies and of neurodegeneration following traumatic brain injury. In another embodiment, the compounds may be used in the treatment or prophylaxis of neurodegenerative disorders. Also provided herein are methods of allowing the compound to distribute into the brain tissue, and imaging the brain tissue, wherein an increase in binding of the compound to the brain tissue compared to a normal control level of binding indicates that the mammal is suffering from or is at risk of developing a neurodegenerative disease, such as Alzheimer's Disease, frontotemporal dementia, other tauopathies or neurodegeneration following traumatic brain injury.

The methods of the present invention are conducted to provide early stage diagnosis of Alzheimer's Disease, frontotemporal dementia, other tauopathies or neurodegeneration following traumatic brain injury. As explained herein the nanobodies of the invention (e.g., F9T or D11C) are ones that specifically recognize tau oligomers (e.g., trimeric tau). Thus, compositions comprising these antibodies and antibody fragments may be used to identify the presence of tau oligomers in a biological sample from a patient to be tested for a tauopathy, such as Alzheimer's disease, wherein the presence of tau oligomers in the sample is indicative that the patient has or is likely to develop the tauopathy (e.g., Alzheimer's disease). In certain embodiments, the assay format that is used may be any assay format that typically employs antibody compositions. Thus, for example, the biological sample may be examined using immunohistology techniques, ELISA, Western Blotting, and the like.

For purposes of the diagnostic methods of the invention, the compositions of the invention (e.g., F9T or D11C) may be conjugated to a detecting reagent that facilitates detection of the scFv. For example, example, the detecting reagent may be a direct label or an indirect label. The labels can be directly attached to or incorporated into the detection reagent by chemical or recombinant methods.

In one embodiment, a label is coupled to the scFv through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels can be used in the assays of the present invention to diagnose a neurodegenerative disease, such as Alzheimer's Disease, these labels are attached to the scFvs of the invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the scFv-based compositions of the invention (e.g., F9T and D11C) are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes tau oligomers in which the antibody is linked to an enzyme (typically by recombinant or covalent chemical bonding). The antibody is detected when the enzyme reacts with its substrate, producing a detectable product. In certain embodiments, enzymes that can be conjugated to detection reagents of the invention include, e.g., (β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis. As noted herein throughout the scFvs of the invention (e.g., F9T and D11C) are targeted specifically to tau oligomers that are characteristic of Alzheimer's Disease, frontotemporal dementia, other tauopathies or neurodegeneration following traumatic brain injury. As such, the scFvs of the invention also may be used to specifically target therapeutic compositions to the sites of tau aggregation. In this embodiment, any therapeutic agent typically used for the treatment of these tauopathies, such as Alzheimer's disease, may be conjugated to scFvs in order to achieve a targeted delivery of that therapeutic agent. Various drugs for the treatment of AD are currently available as well as under study and regulatory consideration. The drugs generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal are just some of the drugs proposed as therapeutic agents for AD that can be conjugated to the scFv compositions of the invention and targeted for therapeutic intervention of AD. The scFv compositions of the invention can be used in any diagnostic assay format to determine the presence of tau oligomers. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the immunobinding methods include obtaining a sample suspected of containing a protein, polypeptide and/or peptide (in this case the tau oligomers), and contacting the sample with a first antibody, monoclonal or polyclonal (in this case a scFv of the invention, such as F9T or D11C), in accordance with the present invention, as the case may be, under conditions effective to allow the formation of immunocomplexes.

The immunobinding methods include methods for detecting and quantifying the amount of the tau oligomer component in a sample and the detection and quantification of any immune complexes formed during the binding process. Here, one would obtain a sample suspected of containing tau oligomers, and contact the sample with an antibody fragment of the invention, such as F9T or D11C, and then detect and quantify the amount of immune complexes formed under the specific conditions.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those scFv molecules specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, an scFv of the invention may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the scFV (e.g., F9T or D11C) is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody (in the present example a scFv of the invention, such as F9T or D11C) is used to detect the target antigen(s), and a second step antibody is then used to detect the biotin attached to the complexed nanobody. In this method the sample to be tested is first incubated in a solution containing the first step nanobody. If the target antigen is present, some of the nanobody binds to the antigen to form a biotinylated nanobody/antigen complex. The nanobody/antigen complex is then amplified by incubation in successive solutions of streptavidin (or avidin), biotinylated DNA, and/or complementary biotinylated DNA, with each step adding additional biotin sites to the nanobody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention shows the sequence of the F9T (SEQ ID NO:1), F9T (SEQ ID NO:9), D11C (SEQ ID NO:11), D4G (SEQ ID NO:13), G12C (SEQ ID NO:15), H2A (SEQ ID NO:17), or H7T (SEQ ID NO:19) scFvs. These sequences can readily be modified to facilitate diagnostic assays, for example a tag (such as GFP) can be added to these scFvs to increase sensitivity. In one exemplary ELISA, antibodies (in the present case the scFvs of the invention, such as F9T or D11C) are immobilized onto a selected surface exhibiting protein affinity, such as a well in a polystyrene microtiter plate. Then, a test composition suspected of containing tau oligomers, such as a clinical sample (e.g., a biological sample obtained from the subject), is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents (e.g., scFvs of the invention, such as F9T or D11C). After binding and/or washing to remove non-specifically bound immune complexes, the bound anti-binding agents are detected. Where the initial binding agents are linked to a detectable label, the immune complexes may be detected directly. Again, the immune complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either tau oligomers or an scFv of the invention (e.g., F9T or D11C), one will generally incubate the wells of the plate with a solution of the antigen or scFvs, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface. In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the tau oligomers and/or scFv composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In various aspects of the invention, it will be desirable to further subject patients to more traditional diagnostic approaches for tauopathies, such as AD. Such general approaches for diagnosis are set out below. The diagnosis of both early (mild) cognitive impairment and AD are based primarily on clinical judgment. However, a variety of neuropsychological tests aid the clinician in reaching a diagnosis. Early detection of only memory deficits may be helpful in suggesting early signs of AD, since other dementias may present with memory deficits and other signs. Cognitive performance tests that assess early global cognitive dysfunction are useful, as well as measures of working memory, episodic memory, semantic memory, perceptual speed and visuospatial ability. These tests can be administered clinically, alone or in combination. Examples of cognitive tests according to cognitive domain are shown as examples, and include "Digits Backward" and "Symbol Digit" (Attention), "Word List Recall" and "Word List Recognition" (Memory), "Boston Naming" and "Category Fluency" (Language), "MMSE 1-10" (Orientation), and "Line Orientation" (Visuospatial). Thus, neuropsychological tests and education-adjusted ratings are assessed in combination with data on effort, education, occupation, and motor and sensory deficits. Since there are no consensus criteria to clinically diagnose mild cognitive impairment, various combinations of the above plus the clinical examination by an experienced neuropsychologist or neurologist are key to proper diagnosis. As the disease becomes more manifest (i.e., becomes a dementia rather than mild cognitive impairment), the clinician may use the criteria for dementia and AD set out by the joint working group of the National Institute of Neurologic and Communicative Disorders and Stroke/AD and Related Disorders Association (NINCDS/ADRDA). On occasion, a clinician may request a head computed tomography (CT) or a head magnetic resonance imaging (MRI) to assess degree of lobar atrophy, although this is not a requirement for the clinical diagnosis.

As noted above, there are various drugs that are presently in use or under development for the treatment of Alzheimer's Disease, frontotemporal dementia, other tauopathies or neurodegeneration following traumatic brain injury. The present invention contemplates the use of scFvs of the invention, such as F9T or D11C, based "diagnostic" methods to further assess the efficacy of treatments. Given the role of tau in these diseases, the ability of a particular therapy to reduce the amount of oligomeric tau will be indicative of an effective treatment, as these forms have been shown to be toxic.

The present invention may involve the use of pharmaceutical compositions which comprise an agent conjugated to a scFv of the invention, such as F9T or D11C, for delivery into a subject having Alzheimer's disease, frontotemporal dementia, other tauopathies or neurodegeneration following traumatic brain injury. Such an agent will ideally be formulated into a pharmaceutically acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

A "variant" of an amino acid sequence of an antibody or antibody fragment described herein or a nucleic acid sequence encoding such an amino acid sequence, is a sequence that is substantially similar to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21. Variant amino acid and nucleic acid sequences include synthetically derived amino acid and nucleic acid sequences, or recombinantly derived amino acid or nucleic acid sequences. Generally, amino acid or nucleic acid sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

The present invention includes variants of the amino acid sequences of the antibodies and antibody fragments described herein, as well as variants of the nucleic acid sequences encoding such amino acid sequences (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21). "Variants" are intended to include sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The antibodies and antibody fragments described herein may be altered in various ways including amino acid substitutions, deletions, truncations, and insertions. Methods for such manipulations are generally known in the art. For example, amino acid sequence variants of the enzyme can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall enzyme retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

EXAMPLES

Example 1

A vast number of studies have correlated protein aggregation with neurodegenerative diseases including AD, Parkinson's and Dementia with Lewy Bodies. Numerous recent studies suggest that specific oligomeric forms of these proteins are involved in neuronal toxicity and can interfere with important functions including long term potentiation. Various soluble oligomeric species of Aβ and a-syn have been shown to occur early during the course of AD and PD, and increasing evidence implicates oligomeric forms of tau in AD and other tauopathies.

Assays are being developed to study tau oligomer content in CSF, and initial results suggest increased levels of tau oligomers in AD CSF compared to non-AD specimens. We developed novel methods to purify recombinant human tau isoforms and to stabilize their oligomeric structures formed by disulfide linkages. Additionally, we purified tau from human AD brain that retains its hyperphosphorylation. These preparations have been used in mice to show that extracellular tau oligomers, but not monomer, inhibited long term potentiation of hippocampal synapses and the formation of associative fear memory. The oligomeric preparation of AD tau produced a similar effect indicating that hyperphosphorylation of tau did not affect inhibition of memory. Taken together tau oligomers were the forms of tau necessary to produce the disease-related effects and validate these structures as a target for drug discovery (Moe, J., et al. Validation of extracellular tau oligomer target for drug discovery in a novel animal model. in Society for Neuroscience. 2010. San Diego, Calif.).

We also developed a novel biopanning technology that combines the imaging capability of Atomic Force Microscopy (AFM) with the diversity of antibody libraries. This unique combination of antibody diversity and imaging capability has enabled us to isolate single chain antibody variable domain fragment (scFv or nanobody) reagents to an array of morphologies of key proteins involved in neurodegenerative diseases including Aβ and alpha-synuclein (a-syn). We isolated nanobodies that specifically recognize monomeric (Emadi, S., et al., Inhibiting Aggregation of alpha-Synuclein with Human Single Chain Antibody Fragments. Biochemistry, 2004. 43: p. 2871-2878), fibrillar (Barkhordarian, H., et al., Isolating recombinant antibodies against specific protein morphologies using atomic force microscopy and phage display technologies. Protein Eng Des Sel, 2006. 19: p. 497-502), and two different oligomeric a-syn morphologies (Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58). The anti-oligomeric a-syn nanobodies do not cross react with oligomeric Aβ, and specifically label PD brain tissue but not AD or healthy tissue (Emadi, S., et al., Detecting morphologically distinct oligomeric forms of alpha-synuclein. J Biol Chem, 2009. 284: p. 11048-58). In addition, we isolated nanobodies to different regions of full length Aβ (Liu, R., et al., Single chain variable fragments against beta-amyloid (Abeta) can inhibit Abeta aggregation and prevent abeta-induced neurotoxicity. Biochemistry, 2004. 43: p. 6959-67) and to three distinct naturally occurring oligomeric Aβ morphologies (Zameer, A., et al., Anti-oligomeric Abeta single-chain variable domain antibody blocks Abeta-induced toxicity against human neuroblastoma cells. J Mol Biol, 2008. 384: p. 917-28). One, A4, specifically recognizes a larger oligomeric Aβ species, inhibits aggregation and extracellular toxicity of Aβ, does not cross react with oligomeric a-syn, and specifically labels Aβ aggregates in human AD brain samples, but not PD or healthy brain tissue (Zameer, A., et al., Anti-oligomeric Abeta single-chain variable domain antibody blocks Abeta-induced toxicity against human neuroblastoma cells. J Mol Biol, 2008. 384: p. 917-28). A second nanobody, E1, recognizes a smaller trimeric or tetrameric A13 species, and similar to A4 inhibits aggregation and extracellular toxicity of A13, does not cross react with oligomeric a-syn, and labels Aβ aggregates in human AD but not healthy brain tissue. Utilizing an AD brain derived oligomeric Aβ preparation obtained from Dr. Selkoe (Walsh, D. M., et al., Naturally secreted oligomers of amyloid beta protein potently inhibit hippocampal long-term potentiation in vivo. Nature, 2002. 416: p. 535-9; Walsh, D. M. and D. J. Selkoe, Abeta Oligomers—a decade of discovery. J Neurochem, 2007), we isolated a third nanobody, C6, that specifically recognizes oligomeric Aβ species derived from human AD brain tissue, but does not recognize Aβ aggregates generated in vitro. The different specificities of each nanobody can be readily observed when each nanobody is expressed on the surface of a filamentous bacteriophage and antibody/antigen complexes are imaged by AFM (Kasturirangan, S., et al., Nanobody specific for oligomeric beta-amyloid stabilizes non-toxic form. Neurobiol Aging, 2010.). Therefore, the combination of antibody libraries and AFM imaging technologies enables us to isolate and carefully characterize reagents that recognize specific protein variants including four different naturally occurring aggregated forms of a-syn and four different naturally occurring aggregated forms of Aβ.

Another powerful advantage of our AFM panning protocol is that not only can we isolate and characterize reagents to specific protein morphologies, but we can do so using only picograms or less of material. In addition the sample does not need to be purified, and the protein does not need to be chemically modified in any way. We can actually isolate nobodies against a single molecule of the target antigen (Shlyakhtenko, L. S., et al., Single-molecule selection and recovery of structure-specific antibodies using atomic force microscopy. Nanomedicine, 2007. 3: p. 192-7). This unique combination of capabilities to isolate different tau isoforms and to generate and characterize reagents that specifically recognize individual protein variants provides us with the means to generate reagents that specifically recognize an array of different tau variants present in human AD brain.

While several reagents already exist that can recognize monomeric and phosphorylated tau, these reagents cannot distinguish between different aggregated states of tau. Reagents that can detect specific forms of tau can provide very powerful tools to facilitate diagnosis of AD and other tauopathies and to follow progression of these diseases or to evaluate therapeutic strategies. While many neurodegenerative diseases have overlapping clinical symptoms and cellular and biochemical mechanisms such as an increase in inflammatory markers, and aggregation of similar proteins, the reagents we propose to develop here will have well defined specificities and selectivities for selected tau forms and should facilitate specific diagnoses of AD and other tauopathies. In combination with other protein and morphology specific reagents against Aβ and a-syn species, these reagents can be used to detect the presence of biomarkers which can readily detect and distinguish many related neurodegenerative diseases including AD, PD, FTD and LBD.

Isolation of different size oligomeric tau species from human AD brain tissue.

An array of different tau isoforms and aggregated assemblies has been shown to be critically important in AD and other tauopathies. Reagents that can specifically label different tau species are needed to clarify the roles of the different forms. Soluble tau oligomers are purified using immunoaffinity and size fractionation to isolate oligomers with different numbers of subunits and isoform composition and multiple post-translational modifications associated with AD such as hyperphosphorylation, truncation, nitrosylation, ubiquitination and glycation. The oligomers in certain embodiments are heterogeneous containing known tau associating proteins such as beta amyloid, ApoE and alpha-synuclein. Aberrant binding of tau with other proteins associated with AD is also anticipated to facilitate generating disease-specific morphologies for nanobody selection. Further, nanobodies are generated against the different tau variants and the nanobodies are used to identify which forms of tau best distinguish AD from healthy tissue in brain and CSF samples.

Methods. Preparation of brain derived oligomeric tau. Tau oligomers are purified from normal and AD brain specimens with tau pathology acquired from the New York Brain Bank (The Taub Institute, Columbia University). Ten grams of tissue will be used for each preparation using the method developed by Ivanovova et al. (Ivanovova, N., et al., High-yield purification of fetal tau preserving its structure and phosphorylation pattern. J Immunol Methods, 2008. 339: p. 17-22) with modifications to isolate different size species of tau oligomers. The advantages of this method include the preservation of tau phosphorylation, simplicity, and high purity of product. We have already used a modified version of this method to isolate tau from an AD brain specimen and have shown that phosphorylation state is preserved. Immunoblot analysis of recombinant tau441 and Tau purified from AD brain showed specific interaction of tau phospho-epitope-specific antibodies against tyrosine 231 and 217 with AD tau but no reactivity with recombinant tau, whereas phospho-independent monoclonal antibody HT7 against total tau interacts with both recombinant and AD tau.

Brain tissue is homogenized in cold 1% perchloric acid, incubated on ice 20 min., and centrifuged at 15,000× g for 20 min. The cleared supernatant is concentrated and buffer exchanged into buffer (20 mM Tris-HCl pH 7.4, 150 mM NaCl, 0.1% Tween 20) using Amicon centrifugal devices (Millipore). Gel and Immunoblot analysis of cleared supernatant indicated the presence of multiple size aggregates of tau with multiple types of modifications causing the appearance of a smear with some predominant bands consistent in size with dimer and trimer. These species were purified by non-denaturing methods described below. Treatment of the preparation with reductant results in a lowered amount of higher molecular weight species indicating that at least some of the tau oligomers were stabilized by disulfide bonds. The incubation time can be varied to increase or decrease the content of higher order oligomeric tau.

Purification and characterization of oligomeric tau. Affinity chromatography to purify oligomeric tau from other protein species is performed using the monoclonal antibody HT-7 (Thermo Scientific). We have observed that the tau epitope recognized by HT-7 is available for binding in tau oligomers and because it binds tau independently of phosphorylation status. The antibody (6 mg) will be coupled to CNBr activated Sepharose according manufacturer's protocol and packed into a Poly-Prep column C10/10 (GE Healthcare). The brain extract is filtered at a flow rate of 0.2 ml/min, and unbound protein are washed off with buffer. Tau is eluted with 0.1 M glycine pH 2.6 in 0.5 ml fractions which is neutralized with 50 1 M Tris-HCl pH 9 prior to analysis by non-reducing SDS-PAGE.

Tau oligomers will be characterized and fractionated using high-pressure liquid chromatography (Beckman Coulter System Gold 32Karat HPLC). A high-resolution gel filtration column (Biosep-SEC-3000, Phenomenex) is used to resolve tau oligomer species ranging in size from monomer (45.9 Daltons) to dodecamer (552 KD). The Biosep-SEC-3000 has an exclusion range of 5 to 700 kDa under native conditions. The column is run using 1× PBS buffer using isocratic conditions at RT, and a run time of 40 minutes. BSA (68 kDa) migrates with a retention time of 24.8 minutes under these conditions. It is expected that a range of oligomers (dimer, trimer, tetramer . . . dodecamer) are resolved using the column although depending on the species present some overlap is expected. Non-reducing SDS-PAGE and immunoblots are used to analyze the tau content in the fractions. AFM is used to determine the size distribution of the tau oligomers in the fractions as shown (see FIG. 1).

Generation and characterization of nanobodies against specific brain derived oligomeric tau forms isolated from AD brain tissue.

We have developed protocols that enable us to readily isolate individual clones from phage display libraries that recognize specific protein morphologies. We have continued to refine our panning protocols to facilitate isolation of reagents against targets that are available in limited amounts, that cannot be purified or that are unstable. Isolation of nanobodies against monomeric, fibrillar and two different oligomeric forms of a-syn, and monomeric, fibrillar and two different oligomeric β-amyloid species have previously been performed. Also, isolation of a nanobody against a third distinct oligomeric beta-amyloid morphology has been performed. We have now included additional negative panning steps to remove nonspecific and undesired binding activities, so virtually all clones isolated after only a single round of panning specifically recognize the target antigen. Using this technique, we can isolate various morphology specific ligands using only nanograms of target. We have also developed AFM based protocols to characterize ligand binding (Wang, M. S., et al., Characterizing Antibody Specificity to Different Protein Morphologies by AFM. Langmuir, 2008), so we can not only isolate morphology specific ligands with only minimal material, but we can characterize binding specificity with limited material as well. This unique capability is ideally suited to isolating ligands against specific protein morphologies as we have demonstrated.

We have performed similar panning protocols to isolate nanobodies against different morphologies of tau generated by synthetically cross-linking tau monomers. In studies we have isolated nanobodies that specifically recognize synthetic dimeric, but not monomeric or synthetic trimeric tau.

Methods. AFM panning against tau aggregates. Nanobodies to the brain derived tau aggregate morphologies are isolated as described previously (Barkhordarian, H., et al., Isolating recombinant antibodies against specific protein morphologies using atomic force microscopy and phage display technologies. Protein Eng Des Sel, 2006. 19: p. 497-502; Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58; Zameer, A., et al., Anti-oligomeric Abeta single-chain variable domain antibody blocks Abeta-induced toxicity against human neuroblastoma cells. J Mol Biol, 2008. 384: p. 917-28). Only nanograms of material are required for the present panning protocols. To ensure that the nanobodies isolated from the panning protocol recognize oligomeric tau, a series of negative selections is performed prior to the positive selection on the brain derived oligomeric tau samples. First a negative panning step is performed on the control protein BSA to remove all non-specific sticky nanobodies. Next a negative panning step is performed using brain derived monomeric tau to remove all nanobodies binding monomeric tau. Then a negative panning step is performed using a control non-diseased brain sample that was prepared similarly to the AD brain sample to remove nanobodies binding to non-disease associated forms of tau (primarily different monomeric forms) and any brain proteins that may purify with tau. Verification is performed after each negative panning step that all phage binding to the non-target samples have been removed by AFM. An aliquot of the remaining phage is added to mica containing a fresh aliquot of the non-target sample and unbound phage are removed. If any phage are observed still binding to the off target samples, a second round of negative panning is performed. The process is repeated until no remaining phage bind the off target sample. After the negative panning steps, the remaining phage are added to the positive brain derived tau oligomer sample and positive clones recovered as described (Barkhordarian, H., et al., Isolating recombinant antibodies against specific protein morphologies using atomic force microscopy and phage display technologies. Protein Eng Des Sel, 2006. 19: p. 497-502; Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58; Zameer, A., et al., Anti-oligomeric Abeta single-chain variable domain antibody blocks Abeta-induced toxicity against human neuroblastoma cells. J Mol Biol, 2008. 384: p. 917-28).

Nanobody Characterization. There are numerous techniques that can be used to determine binding specificity of each of the nanobodies isolated against the different target tau morphologies depending on the availability and stability of the target antigen.

Specificity using Biacore, ELISA, Western Blot or Dot Blot. For those tau morphologies that can be obtained in reasonable quantity, accurate binding kinetics can be determined by surface plasmon resonance using a BIAcore X biosensor. Since chemical immobilization may affect various aggregated protein morphologies, binding specificity can be determined by ELISA, western or dot blot, depending on how easy it is to purify the target aggregate morphology. The protocols for each of these assays have been published (Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Inhibiting Aggregation of alpha-Synuclein with Human Single Chain Antibody Fragments. Biochemistry, 2004. 43: p. 2871-2878; Zameer, A., et al., Single Chain Fv Antibodies against the 25-35 Abeta Fragment Inhibit Aggregation and Toxicity of Abeta42. Biochemistry, 2006. 45: p. 11532-9; Liu, R., et al., Single chain variable fragments against beta-amyloid (Abeta) can inhibit Abeta aggregation and prevent abeta-induced neurotoxicity. Biochemistry, 2004. 43: p. 6959-67; Zhou, C., et al., A human single-chain Fv intrabody blocks aberrant cellular effects of overexpressed alpha-synuclein. Mol Ther, 2004. 10: p. 1023-31; Liu, R., et al., Residues 17-20 and 30-35 of beta-amyloid play critical roles in aggregation. J Neurosci Res, 2004. 75: p. 162-71; Liu, R., et al., Proteolytic antibody light chains alter beta-amyloid aggregation and prevent cytotoxicity. Biochemistry, 2004. 43: p. 9999-10007).

Specificity using AFM. If a oligomeric tau sample is not be able to determined for nanobody specificity by conventional means such as western blot as described above, different AFM based methods can be used to determine antibody specificity for antigen targets that are not suitable for analysis as described above, or that are available in only limited amounts. Nanobody specificity can be determined by height distribution analysis as described (Wang, M. S., et al., Characterizing Antibody Specificity to Different Protein Morphologies by AFM. Langmuir, 2008), by recognition imaging (Marcus, W. D., et al., Isolation of an scFv targeting BRG1 using phage display with characterization by AFM. Biochem Biophys Res Commun, 2006. 342: p. 1123-9), or by using phage displayed nanobodies (see FIG. 1).

Identification of oligomeric tau specific nanobodies that distinguish between CSF and brain tissue from healthy and AD patients.

Individual nanobodies are screened against normal and AD brain tissue specimens using ELISA, dot blot and immunohistochemistry to identify those nanobody reagents that have the most potential to distinguish between healthy and AD cases.

Methods: Western- and Dot-blot assays: All assays are performed essentially as described (Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58).

Immunohistochemistry of brain tissue. Brain tissue is pre-treated with 0.1% triton X-100 for 30 minutes. Nanobody is then added (0.2 mg/ml) to the brain sections and incubated for 1 hour at room temperature. Primary antibodies (mouse anti-c-Myc and anti-Synaptophysin (Santa Cruz) 1/500 dilution in BSA 3%) are then applied and incubated for 1 hour at room temperature. The brain sections are washed 3 times with PBS and incubated with 1/1000 dilution of secondary antibody in BSA 3% (goat anti-mouse IgG Alexa Fluor 488 and goat anti-rabbit Alexa Fluor 594, invitrogen) for 45 min at room temperature. Images are taken with a confocal microscope at 60× magnification.

Example 2

Alzheimer's disease (AD) is a prevalent neurodegenerative disease in which the progressive neuronal loss and cognitive dysfunction are observed. About 5 million Americans are living with AD and this number is believed to triple by 2050. Unfortunately, no cure has been found as of yet. The main pharmacological approaches are symptom treatment such as acetylcholine inhibitor. AD has two neuropathological features: extracellular deposit of amyloid beta fibrillar or diffuse and intracellular neurofibrillary tangle (NFT) of tau. Increasing evidence suggests that protein misfolding, aggregation and fibril formation both features are closely associated with the pathogenesis of AD. Normal tau plays important role in assembling neuron microtubule and stabilizing its structure and physiological function while abnormally hyperphosphorylated tau and its oligomeric and aggregated forms are considered correlated with synapse loss. Reagents targeting oligomeric tau over monomeric or aggregated tau or any nonspecific protein that potentially interfere with the aggregation process without disturbing the normal tau function are needed. Besides, detecting tau oligomer not aggregated tau with such reagents is a promising diagnostic approach in early stage of AD cases.

As described herein, single chain variable fragment (scFv) against tau oligomers is such a reagent. scFv is a fusion of one pair of heavy chain and light chain variable domains of immunoglobulin G (IgG) to make one antigen-binding site which is specific to only one epitope on the antigen. scFv specificity can be increased by affinity mature. scFv has smaller molecular weight (29 kD) potentially penetrating blood-brain-barrier before it's compromised in the later stage of AD. Due to lack of constant domains, scFv is unlikely to induce inflammation in clinical test. To fulfill scFv screening, recovering and reproducing, we used Sheets phagemid library which is a human phage-displayed scFv library of up to $6.7 \times 10^9$ variety. An individual phage-display scFv clone is a filamentous bacteriophage with a molecule of scFv expressed on its surface and linked with a g3p. It is easy to be identified with atomic force microscopy (AFM) and infectious to common E. coli strains to facilitate genetic modification.

We have successfully performed a novel biopanning combining phage-displayed library and AFM to obtain scFv clones specific to trimeric tau which shows in Lactate Dehydrogenase (LDH) test as the most toxic of all available tau species in our lab. After DNA sequence modification, F9T keeps specificity to oligomeric tau and displays efficient soluble scFv expression and purification. F9T also demonstrated potentials of discriminate AD from ND on human middle temporal gyrus (MTG) tissue and human cerebrospinal fluid, both of which are enriched with abnormal tau in AD.

Results

I. Select scFv Against Different Tau Oligomeric Forms Using Purified Tau Dimer, Trimer, Mixed Oligomer and Monomer Samples Using AFM Biopanning Protocols A. Select the most toxic morphology of tau through LDH test on SH-SY5Y neuroblastoma cell line and its cholinergic differentiated form.

In order to identify the most promising oligomeric tau species to target with our antibody fragment library, we first tested which tau species were toxic toward a neuronal cell line. We performed cell viability assays using undifferentiated and cholinergic like SH-SY5Y human neuroblastoma cells treated with monomeric, dimeric or trimeric tau. We tested two different isoforms of tau, 4N1R and 4N2R and measured toxicity using an LDH assay as described. As shown in FIGS. 2(A) and (B), trimeric tau 4N1R and 4N2R were toxic to undifferentiated SHSY-5Y cells while monomeric and dimeric tau were not. Essentially identical results were obtained when the SHSY-5Y cells were first differentiated to a cholinergic-like phenotype (data not shown) before treatment with monomeric, dimeric or trimeric tau. Toxicity induced by trimeric tau showed concentration dependence. These results suggest that trimeric tau may be a critically important species in the progression of AD.

B. Biopanning against purified synthetic trimeric tau 4N1R using the Sheets phagemid library.

We performed biopanning studies to isolate single chain variable fragments (nanobodies) against the different tau species. We utilize a novel biopanning protocol that combines the imaging capabilities of AFM with the binding diversity of phage-displayed antibody technology. To isolate nanobodies against specific oligomeric morphologies of a target protein, we have modified the protocol to include negative panning steps to remove clones that bind to non-desired protein forms. To isolate nanobodies against oligomeric tau we incorporated two negative panning steps. In the first negative panning step, we remove all non-specific "sticky" clones by panning against a generic protein, bovine serum albumin (BSA). In the second negative panning step, we remove all clones that bind to the non-desired monomeric form of tau. During our negative panning, we removed as many non-desired clones as possible. The purity of monomeric tau was critical since we did not want to lose oligomeric tau clones during this step. We obtained a sample of pure monomeric tau for the negative panning to remove phage clones binding monomeric tau, and then used aliquots of the remaining phage to screen for dimeric and trimeric specific clones respectively. Since we found that the trimeric tau species was much more toxic to human neuronal cell lines than monomeric or dimeric, we focused our efforts on isolating phage clones that were selective for trimeric tau 4N1R.

C. Screen Monoclonal Phage Specific to Trimeric Tau 4N1R by AFM

After negative panning against BSA and monomeric tau, we recovered around 100 clones from the positive selection against trimeric tau 4N1R. Since the amounts of tau samples provided to us by Oligomerix was limiting, we were not able to screen each of the phage by conventional ELISA to determine which of the 100 clones had high specificities for trimeric over monomeric tau. Instead we screened each individual phage clone by AFM for binding to the different tau species. We coincubated each phage sample with monomeric, dimeric and trimeric tau samples which had been previously fixed to a mica substrate. Unbound phage was removed by excess stringent rinsing and remaining bound phage were imaged by AFM. After screening all 100 clones in this manner, we identified clones that selectively bound either dimeric or trimeric tau, but not monomeric tau. The AFM panning protocol allows us to screen all 100 clones for binding specificity using only nanogram amounts of antigen, although the assay is quite time-consuming. After screening all 100 phage clones, we selected 6 clones for further study based on highest specificity for trimeric tau.

D. DNA Sequencing and frame-shift correction of isolated clones.

We validated the DNA sequence of each of the six clones to ensure that a full length scFv was encoded (FIG. 4). In each of the six cases a single base pair was missing at the beginning of the coding sequence. In order to produce soluble scFv for further characterization, we needed to correct the frame shift to enable efficient expression of the scFv. We designed forward and reverse primers which enabled us to modify each scFv sequence by polymerase chain reaction (PCR) and correct the frame shift (see, e.g., FIG. 3). We then cloned the corrected scFv sequence into an expression plasmid that also contained a c-myc tag for identification and a poly-histidine tag for purification. The corrected F9 clone, F9T, expressed at very high levels, purified readily and maintained high specificity for oligomer tau over monomeric tau and fibril tau in the phage form viewed by AFM, so this clone was selected for further study.

II. Select Fragments That Show Disease Specificity in AD Brain Sections

A. Preliminary Specificity and Affinity Test of Selected Nanobodies on Age Matched Alzheimer's and Non-Demented Brain Sections While monomeric tau plays a crucial role in microtubule assembly and stability, oligomeric tau is toxic to cells. Oligomeric tau may be the result of tau hyperphosphorylation and other posttraslational modifications. Oligomeric tau detaches from microtubules and may then aggregate further to form the neurofibillary tangles which are a hallmark feature of Alzheimer's. It is likely that misfolding and aggregation of tau is intimately linked with misfolding and aggregation of amyloid-beta (Aβ), so detection of the different oligomeric forms of these proteins has promise in diagnosis and treatment of Alzheimer's. We analyzed the reactivity of the F9T nanobody against trimeric tau with homogenized post-mortem brain tissue, which was obtained from the middle temporal gyrus of different Braak stage Alzheimer's brain defined by the extraneuronal plaque frequency. All brain samples are of age matched and were generously provided by Thomas G. Beach from Banner Sun Health Research Institute. We analyzed six samples obtained from non-demented sources (ND1 to ND6). The ND samples, patients who demonstrated no obvious symptoms of dementia, were broken into two categories based on presence of Aβ plaques: ND1, ND2 and ND3 had no Aβ plaque (Braak stage I to II) while ND4, ND5 and ND6 all had slight plaque frequency (Braak stage I to II). The six Alzheimer's brain tissue samples (AD1 to AD6) were from patients diagnosed with Alzheimer's disease. The samples were divided by plaque frequency where AD1, AD2 and AD3 brain samples show moderate frequent plaque (Braak stage III to IV) while AD4, AD5 and AD6 brain samples show the most severe plaque frequency (Braak stage III to IV). Both F9T preparations show similar reactivity where the strongest signals are obtained from AD2 and AD3, although strong signals are obtained with 5 of 6 AD samples. Interestingly, there is almost no reactivity with any of the cognitively normal tissue samples that did not contain any Aβ plaques. The three cognitively normal samples that did contain plaques did show reactivity suggesting an interaction between Aβ aggregation and tau aggregation as noted above. Another interesting trend is that the AD1-3 samples have higher reactivity on average than the AD4-6 samples. The high plaque frequency of the AD4-6 samples may indicate the presence of more neurofibrillar tau and less oligomeric tau.

B. Preliminary Specificity Test of Selected Nanobody Displayed Phage F9T on Human Cerebrospinal Fluid (CSF) as a Potential Diagnostic Technique Total tau (T-tau) and phosphorylated tau (P-tau) levels in CSF are important biomarkers for Alzheimer's for several reasons. That T-tau level increase in AD CSF can discriminate sporadic AD from non-demented age-matched controls with high sensitivity. T-tau level also reflects neuronal and axonal degeneration which enables broader use to other dementias than AD such as Creutzfeldt-Jakob disease (CJD) and Lewy body disease (LBD). Compared with normal level of P-tau in other common dementias and normal aging, P-tau level increase markedly in AD. Combining this feature with decreased Aβ42 in CSF, a promising diagnostic approach can be obtained. F9T's ability of recognizing tau over other forms of amyloid can be a crucial part of such an approach.

F9T nanobody displayed phage's interaction with human CSF proteins was imaged by atomic force microscopy. The preliminary result demonstrates the presence of phage binding in AD versus the absence of phage in ND, which is in accordance with the fact that AD CSF contains an increased level of total tau. While parameters may be adjusted, this test needs is potentially a more sensitive way of detecting CSF tau level and a promising diagnostic technique for AD and other tauopathies.

Example 3

Traumatic Brain Injury (TBI) affects over 1.7 million people each year, and over 230,000 soldiers have suffered TBI on the battlefield (http://www.dvbic.org/traumatic-brain-injury-tbi-awareness-and-prevention). Around 10-20% of soldiers serving in Iraq and Afghanistan have suffered TBI from different sources. It is well established that traumatic brain injury (TBI) can disrupt cognitive functioning. The brain is very sensitive to stress and injury and responds by expressing a variety of neuromorphological and neurochemical changes. TBI induces axonal injury and damage to protein transport mechanisms, so neurofilament proteins, such as tau, which accumulate in axons following TBI, play a critical role in TBI. Following TBI, increased levels of tau in brain fluid, CSF and serum samples are all predictive of adverse long-term clinical outcomes. Neurofibrillary tau aggregates have been identified in soldiers suffering from TBI as well as in many athletes such as football players that suffer repeated head trauma, suggesting a similar mechanism behind these injuries. Aggregates of tau are also the major component of the neurofibrillary tangles that are a hallmark feature in the brains of Alzheimer's disease (AD) patients, and TBI is a risk factor for AD. Therefore tau clearly plays a critical role in brain function, particularly cognitive functions, and the ability of tau to support cognitive function is impaired following TBI.

Mild traumatic brain injury (mTBI) frequently leads to chronic traumatic encephalopathy (CTE) and other neurodegenerative disorders including AD, Parkinson's disease (PD), and amyotrophic lateral sclerosis. While the mechanism of progression and risk factors for mTBI to convert to CTE and other neurodegenerative diseases are not well known, accumulation of tau aggregates in neurofibrillary tangles (NFTs) and glial tangles in various regions of the brain are a common feature indicating that tau is a viable therapeutic target to prevent neurodegeneration following TBI. Tau is a natively unfolded protein that can aberrantly fold into various aggregate morphologies including β-sheet containing fibrillar forms found in the NFTs and in different oligomeric species (Garcia-Sierra, F., et al., *Conformational changes and truncation of tau protein during tangle evolution in Alzheimer's disease*. J Alzheimers Dis, 2003. 5: p. 65-77; Ghoshal, N., et al., *Tau conformational changes correspond to impairments of episodic memory in mild cognitive impairment and Alzheimer's disease*. Exp Neurol, 2002. 177: p. 475-93; Grundke-Iqbal, I., et al., *Abnormal phosphorylation of the microtubule-associated protein tau (tau) in Alzheimer cytoskeletal pathology*. Proc Natl Acad Sci USA, 1986. 83: p. 4913-7; Schweers, O., et al., *Structural studies of tau protein and Alzheimer paired helical filaments show no evidence for beta-structure*. J Biol Chem, 1994. 269: p. 24290-7). While NFTs have been implicated in mediating neurodegeneration in AD and tauopathies, animal models of tauopathy have shown that memory impairment and neuron loss do not associate well with accumulation of NFT, but do associate well with oligomeric forms of tau (Santacruz, K., et al., *Tau suppression in a neurodegenerative mouse model improves memory function*. Science, 2005. 309: p. 476-81) and a regional dissociation of neuron loss and NFT pathology. The pathological structures of tau most closely associated with AD progression were shown to be tau oligomers (Berger, Z., et al., *Accumulation of pathological tau species and memory loss in a conditional model of tauopathy*. J Neurosci, 2007. 27: p. 3650-62; Maeda, S., et al., *Increased levels of granular tau oligomers: an early sign of brain aging and Alzheimer's disease*. Neurosci Res, 2006. 54: p. 197-201; Sahara, N., S. Maeda, and A. Takashima, *Tau oligomerization: a role for tau aggregation intermediates linked to neurodegeneration*. Curr Alzheimer Res, 2008. 5: p. 591-8). Similar to the many studies that implicate oligomeric rather than fibrillar forms of Aβ in neuronal dysfunction, these studies all indicate that oligomeric tau aggregates, rather than tau tangles, are acutely neurotoxic and are responsible for the neurodegenerative phenotype. Therefore toxic oligomeric tau species are likely play a critical role in neurodegeneration following TBI. Oligomeric tau species have been shown to contribute to neurotoxicity through an "infectious" model of disease progression. Extracellular tau aggregates can initiate tau misfolding intracellularly (Frost, B., R. L. Jacks, and M. I. Diamond, *Propagation of tau misfolding from the outside to the inside of a cell*. J Biol Chem, 2009. 284: p. 12845-52), tau pathology spreads contiguously throughout the brain from early to late stage disease (Schonheit, B., R. Zarski, and T. G. Ohm, *Spatial and temporal relationships between plaques and tangles in Alzheimer-pathology*. Neurobiol Aging, 2004. 25: p. 697-711), and brain extract from a transgenic mouse with aggregated mutant human tau transmits tau pathology when introduced into the brains of mice expressing normal human tau (Clavaguera, F., et al., *Transmission and spreading of tauopathy in transgenic mouse brain*. Nat Cell Biol, 2009. 11: p. 909-13). A receptor-mediated mechanism for the spread of tau pathology by extracellular tau has been described (Gomez-Ramos, A., et al., *Characteristics and consequences of muscarinic receptor activation by tau protein*. Eur Neuropsychopharmacol, 2009. 19: p. 708-17). These studies further support oligomeric tau as a particularly promising therapeutic target for TBI-neurodegeneration.

The present inventors have developed unique technology that enables us to isolate reagents that bind specific morphologies of a target protein. The inventors have combined the imaging capabilities of atomic force microscopy (AFM) with the binding diversity of phage display antibody technology to allow us to identify the presence of specific protein morphologies and then isolate reagents that bind a target morphology (Barkhordarian, H., et al., *Isolating recombinant antibodies against specific protein morphologies using atomic force microscopy and phage display technologies*. Protein Eng Des Sel, 2006. 19: p. 497-502). The inventors have developed a series of morphology specific single chain antibody fragments (nanobodies) that have great promise for distinguishing between different neurodegenerative diseases and for targeting specific toxic aggregate species and have recently isolated several nanobodies that selectively bind toxic oligomeric tau species. The nanobodies distinguish between AD and healthy post-mortem human tissue and can detect oligomeric tau in post-mortem AD CSF samples. Here the inventors utilize the oligomeric tau specific nanobodies as therapeutics to block toxicity of tau following TBI in mouse models. The pool of morphology-specific nanobodies are also used to analyze brain tissue of the mice for the presence of different aggregated protein species.

Neurobehavioral, biochemical and neuropathological characterization of mouse models of neurodegeneration (Abdullah, L., et al., *Proteomic CNS profile of delayed cognitive impairment in mice exposed to Gulf War agents*. Neuromolecular Med. 13: p. 275-88; Abdullah, L., et al., *Lipidomic Profiling of Phosphocholine Containing Brain Lipids in Mice with Sensorimotor Deficits and Anxiety-Like Features After Exposure to Gulf War Agents*. Neuromolecular Med; Todd Roach, J., et al., *Behavioral effects of CD40-CD40L pathway disruption in aged PSAPP mice*. Brain Res, 2004. 1015: p. 161-8), in particular different TBI models (Crawford, F., et al., *Identification of plasma biomarkers of TBI outcome using proteomic approaches in an APOE mouse model*. J Neurotrauma. 29: p. 246-60; Crawford, F., et al., *Apolipoprotein E-genotype dependent hippocampal and cortical responses to traumatic brain injury*. Neuroscience, 2009. 159: p. 1349-62; Crawford, F. C., et al., *Genomic analysis of response to traumatic brain injury in a mouse model of Alzheimer's disease (APPsw)*. Brain Res, 2007. 1185: p. 45-58; Ferguson, S., et al., *Apolipoprotein E genotype and oxidative stress response to traumatic brain injury*. Neuroscience. 168: p. 811-9) including a recently developed mild TBI (mTBI) model of single (s-mTBI) and repetitive (r-mTBI, 5 injuries given at 48 h intervals) injury (Mouzon, B. C., et al., *Repetitive mild traumatic brain injury in a mouse model produces learning and memory deficits accompanied by histological changes*. J Neurotrauma) have been previously published. In wild type C57BL/6 mice this injury demonstrates acute motor and cognitive deficits in both paradigms, but more significant deficits following r-mTBI, and neuropathological analyses show axonal injury and reactive gliosis, more evident in the r-mTBI mice. Ongoing studies reveal progressive neuropathological changes and persistence of neurobehavioral deficits in the r-mTBI model at 6, 12 and 18 months, whereas s-mTBI recover the level of performance of anesthesia control groups. We have also administered this mTBI paradigm to the hTau transgenic mouse which expresses all isoforms of non-mutant human tau on a null murine tau background. In young hTau mice r-mTBI appears to precipitate hyperphosphorylation of Tau while in aged hTau mice (18 months) r-mTBI exacerbates the existing burden of Tau pathology and glial activation. This r-mTBI model in hTau mice is thus an ideal platform in which to evaluate potential TBI therapeutics targeting tau pathogenicity. Tau induced toxicity and memory deficits following TBI can be safely reduced by selectively targeting toxic oligomeric tau species using recombinant antibody fragments that do not initiate an inflammatory response.

Example 4

Isolation and Characterization of Single Chain Variable Fragments Selective for a Neurotoxic Oligomeric Tau Species Alzheimer's disease (AD) is a devastating progressive neurodegenerative disease that causes brain atrophy, memory deterioration and cognitve loss in affected individuals. It is the sixth leading cause of death in the United States, currently affecting over 5.4 million Americans with annual costs of over $200 billion in medical care. Although AD was first discovered over a hundred years ago, and substantial progress has been made in understanding the etiology of the disease, there are still no effective therapeutic or definitive diagnostic approaches available. AD is characterized by the presence of two hallmark pathologies: extracellular neuritic plaques containing insoluble fibrillar aggregates of amyloid-beta (Aβ) and intracellular neurofibrillary tangles (NFTs) containing fibrillar aggregates of tau. Although these insoluble aggregated species have long been considered as the primary toxic elements of AD, increasing evidence indicates that small soluble oligomeric forms of both Aβ and tau play more critical roles in the onset and progression of AD than the fibrillar aggregates. The role of Aβ aggregation in AD in particular has been extensively studied, however despite very promising results in animal models, various therapeutic routes of targeting Aβ aggregation have had only very limited success in clinical trials. In part due to the rather disappointing results obtained from therapeutic trials targeting Aβ, the role of tau in the progression of AD is gaining more attention, including studies to elucidate the roles of different variants and aggregate forms of tau.

Tau is a microtubule-associated protein, generally located in the axons of neurons, where it is involved in the assembly and stabilization of microtubules from tubulin. Although human tau is encoded by a single gene on chromosome 17q21, six major tau isoforms can be formed by alternative splicing of exons 2, 3 and 10. Tau can also be post-translationally modified by phosphorylation, glycosylation, ubiquitinylation, or glycation among others resulting in a wide variety of different tau species that can exist in vivo. Since hyperphosphorylated tau species are predominantly found in the hallmark NFTs, phosphorylation of tau has been extensively studied and inhibiting kinases involved in tau phosphorylation has been pursued as a potential therapeutic approach. Levels of hyperphosphorylated tau have also been studied as biomarkers for AD, and ratios of different tau isoforms particularly phosphorylated variants correlate well with tauopathies including FTD and AD. Hyperphosphorylation of the microtubule-binding domain (MBD) of tau results in a conformational change that promotes misfolding and loss of physiological function. However, phosphorylation of tau may also be required for some cellular functions including adult neurogenesis, as new adult-born granule neurons contain a significant amount of a hyperphosphorylated three repeat tau variants. Therapeutic strategies aimed at regulating kinase activity bear the risk of interrupting normal phosphorylation dependent functions of tau. Given the complexity of the many different potential isoforms of tau that can occur in vivo and the uncertainty as to the physiological effects of tau hyperphosphorylation and aggregation, the roles of different hyperphosphorylated and aggregated tau variants in AD remain controversial and the most promising diagnostic or therapeutic targets are still not known.

Similar to the neurotoxic effects observed with soluble oligomeric aggregates of Aβ, numerous studies indicate that soluble aggregates of tau play an important role in the pathology of AD. Both brain derived and recombinant oligomeric tau aggregate species disrupt intracellular calcium levels and are toxic to cultured human neuronal cells when added extracellularly. In animal models expressing human tau, neurodegeneration-related phenotypes including behavioral impairments, neuronal loss, and synapse lesions correlate better with the presence of soluble tau oligomeric and prefilament species than with fibrillar NFT levels. Neuronal loss also precedes NFTs formation suggesting involvement of other species such as oligomeric tau variants. In postmortem human brains, high oligomeric tau levels were detected in the frontal lobe cortex at early stages of AD before the presence of NFTs. Oligomeric tau may also be responsible for transmission of pathology with a prion-like mechanism as NFT tau pathology spreads from brain regions seeded with oligomeric tau into other regions resulting in aggregation of endogenous tau. We have previously shown using non-phosphorylated recombinant human tau (NPrhTau) that trimeric, but not monomeric or dimeric aggregates are toxic to human neuronal cells.

Here we describe isolation of antibody based reagents that selectively recognize the toxic NPrhTau trimeric species. We used a single chain variable domain antibody fragment (scFv) library (Sheets, M. D., et al., Efficient construction of a large nonimmune phage antibody library: the production of high-affinity human single-chain antibodies to protein antigens. Proc Natl Acad Sci USA, 1998. 95(11): p. 6157-62) as source of binding diversity and an atomic force microscopy (AFM) based biopanning protocol (Barkhordarian, H., et al., Isolating recombinant antibodies against specific protein morphologies using atomic force microscopy and phage display technologies. Protein Eng Des Sel, 2006. 19(11): p. 497-502; Emadi, S., et al., Isolation of a human single chain antibody fragment against oligomeric alpha-synuclein that inhibits aggregation and prevents alpha-synuclein-induced toxicity. J Mol Biol, 2007. 368(4): p. 1132-44; Emadi, S., et al., Detecting morphologically distinct oligomeric forms of alpha-synuclein. J Biol Chem, 2009. 284(17): p. 11048-58; Kasturirangan, S., et al., Nanobody specific for oligomeric beta-amyloid stabilizes nontoxic form. Neurobiol Aging, 2012. 33(7): p. 1320-8; Kasturirangan, S., et al., Isolation and characterization of antibody fragments selective for specific protein morphologies from nanogram antigen samples. Biotechnol Prog, 2013. 29(2): p. 463-71; Zameer, A., et al., Single chain Fv antibodies against the 25-35 Abeta fragment inhibit aggregation and toxicity of Abeta42. Biochemistry, 2006. 45(38): p. 11532-9) as a selection tool to isolate scFvs that selectively bound the trimeric tau species. We utilized several subtractive panning steps in the selection protocol to ensure the removal of all scFvs cross-reactive with monomeric tau and other off-target proteins. We identified three different scFvs that bound trimeric but not monomeric or fibrillar tau. The three different scFvs all bound distinct epitopes on the trimeric tau aggregate. The scFvs reacted with naturally occurring oligomeric tau in brain tissue from a transgenic AD mouse model that overexpresses both Aβ and tau and showed that significant levels of oligomeric tau are present in brain tissue from this mouse model long before NFTs are detected. The scFvs also reacted with oligomeric tau naturally present in post-mortem human AD brain tissue. Levels of oligomeric tau in the post-mortem human brain tissue correlated with progression of AD as oligomeric tau levels increase with Braak stage.

Materials and Methods scFv Phage Display Library—The Sheets phage display scFv library (Sheets, M. D., et al., Efficient construction of a large nonimmune phage antibody library: the production of high-affinity human single-chain antibodies to protein antigens. Proc Natl Acad Sci U.S.A., 1998. 95(11): p. 6157-62) with an estimated diversity of $6.7 \times 10^9$ was generously provided by Dr. Yu Zhou (Department of Anesthesia, University of San Francisco) and used for biopanning. Phage was produced and purified as previously described (Marks, J. D., et al., By-passing immunization. Human antibodies from V-gene libraries displayed on phage. J Mol Biol, 1991. 222(3): p. 581-97). A final titre of $10^{13}$-$10^{14}$ pfu/mL was used for biopanning.

Aggregated Tau species—Two isoforms (1N4R and 2N4R) of non-phosphorylated recombinant human tau (NPrhTau) species were used for the panning protocols. Monomeric and oligomeric forms of tau were generated as described above. A fibrillar 2N4R aggregate stock was prepared following a heparin fibrillation protocol by mixing rhTau 2N4R monomer (final molarity of 4 μM) and low molecular weight heparin (final molarity of 4 μM) in final 20 mM tris-HCl pH 7.4 and final 5 mM DL-Dithiothreitol (DTT) in deionized water (DI water). The mixture was incubated at 37° C. for 2 weeks with occasional stirring.

Biopanning against NPrhTau 1N4R trimer—The biopanning process was performed essentially as previously described (Kasturirangan, S., et al., Isolation and characterization of antibody fragments selective for specific protein morphologies from nanogram antigen samples. Biotechnol Prog, 2013. 29(2): p. 463-71) with the following modifications. The biopanning process is divided into "subtractive panning" and "positive panning" steps (FIG. 6). The subtractive panning steps are designed to remove all scFv-displayed phage from the library pool which bind to non-desired antigens including a control protein bovine serum albumin (BSA) used to remove non-specific binding phage and monomeric tau used to remove all phage binding non-aggregated linear epitopes of tau. The positive panning step then recovers any scFv-displayed phage from the remaining phage pool that selectively bind trimeric tau. Each step is monitored by AFM to ensure that essentially all phage binding BSA and monomeric tau are removed and phage binding to trimeric tau are recovered.

Subtractive panning step—A set of high affinity immunotubes were coated with 2 mL/tube of 1 mg/mL BSA in carbonate/bicarbonate coating buffer pH 9.6 and another set with 2 mL of 12 μg/mL tau 1N4R monomer in the same coating buffer and incubated overnight at 4° C. After antigen immobilization, immunotubes were washed extensively with phosphate buffered saline (PBS) and sealed to keep moist. A total volume of 0.5 mL of the phage display library was added to the first tube coated with BSA. The tube was then sealed and incubated at room temperature for 30 minutes with gentle agitation ensuring that the phage solution did not contact uncoated regions in the immunotube. After incubation, the phage solution was removed and additional unbound phage rinsed off with 100 μl PBS. The phage and rinse solutions were combined and added to a second tube containing BSA and then to sequential tubes following the same procedure for each tube. The final recovered phage solution volume was approximately 1 mL. A 10 μL aliquot of phage solution recovered after incubation with each tube was added to mica containing BSA and imaged by AFM to determine whether there were any phage remaining in the phage pool that could still bind BSA. If no bound phage were observed, the subtractive panning step successfully removed essentially all phage binding to the target antigen, in this case BSA. A second subtractive panning round was performed using immunotubes coated with monomeric 1N4R rhTau to remove all phage binding monomeric tau. The process was performed and monitored as described above. After the second round of subtractive panning, the final remaining phage solution was stored in 100 μL aliquots at −80° C.

Positive panning—A 10 μl aliquot of 60 μg/mL of positive target antigen, trimeric rhTau 1N4R, was deposited on a piece of freshly cleaved mica, incubated at room temperature for 10 minutes, and then extensively washed with DI water and dried. A 200 μl aliquot of the remaining phage pool obtained after subtractive panning was added to the mica, incubated at room temperature for 10 minutes, and then washed with 2 mL 0.1% tween/DI water and at least 10 mL DI water to remove all unbound phage. The positive panning step was performed in duplicate for analysis by AFM to verify the presence of phage binding trimeric tau. Bound phage were eluted with 1.4% triethylamine (TEA) and neutralized after 5 minutes with an equal volume of 1M Tris-HCl pH 7.4 buffer. The eluted phage stock were recovered as described (Emadi, S., et al., *Detecting morphologically distinct oligomeric forms of alpha-synuclein*. J Biol Chem, 2009. 284(17): p. 11048-5). Single colonies were collected, individually grown and stored at −80° C.

Atomic force microscope (AFM) imaging—AFM imaging and analysis were performed as described previously (Wang, M. S., et al., *Characterizing antibody specificity to different protein morphologies by AFM*. Langmuir, 2009. 25(2): p. 912-8). Aliquots were deposited and incubated for 10 min on freshly cleaved mica at room temperature before the mica surface was washed extensively with DI water and dried with compressed nitrogen flow. To image phage binding specificity for the different tau isoforms, an additional stringent wash with 0.1% tween/DI water was performed to remove non-specific binding phage. The coated mica samples were imaged in air using a MultiMode AFM Nanoscope IIIA system (Veeco/Digital instruments, Santa Barbara, Calif.) operating in tapping mode using silicon AFM probes (VISTAprobes, nanoscience instruments).

Single clone screening with AFM—Following positive panning, a phage preparation from each individual recovered clone was analyzed for target binding specificity by AFM. Aliquots of each phage were added to mica coated with either BSA, monomeric or trimeric tau. Samples showing the highest binding levels toward trimeric tau, but no reactivity toward BSA or monomeric tau were selected for further characterization.

DNA sequence correction—DNA sequences of recovered clones were obtained and compared with other known scFv sequences (Marks, J. D., et al., *By-passing immunization. Human antibodies from V-gene libraries displayed on phage*. J Mol Biol, 1991. 222(3): p. 581-97). All recovered clones from the positive panning step contained a missing base pair near the amino terminal of the scFv sequence resulting in a shift in the reading frame (FIG. 12). The reading frame shift was corrected in selected clones using polymerase chain reaction (PCR) with customized primers (FIG. 13). The forward primers encompass the NcoI site (5'-CCATGG-3') upstream of scFv sequence and include the missing base, while the reverse primer encompasses the NotI site (5'-GCGGCCGC-3') downstream of scFv sequence. The corrected scFv gene sequences were ligated into the pGEMT plasmid vector for sequencing to confirm the desired DNA sequence, and then ligated into the pIT2 plasmid vector which contains a hexahistidine tag and c-myc tag for protein expression. The pIT2 plasmids were transformed into either *E. coli* strain HB2151 for scFv expression or TG1 for phage expression.

Phage binding specificity assay—Binding specificities of the sequence corrected phage clones were verified by AFM. Purified phage were deposited and incubated on mica coated with the different tau species and imaged to confirm binding specificity as described above.

Soluble scFv production and purification—Production and purification of the sequence corrected scFv proteins were performed as described previously (Barkhordarian, H., et al., *Isolating recombinant antibodies against specific protein morphologies using atomic force microscopy and phage display technologies*. Protein Eng Des Sel, 2006. 19(11): p. 497-502). Concentrated supernatant, periplasm and cell lysate fractions were prepared separately and tested for presence of scFv. Most of the scFv was located in the periplasmic fraction, with lower amounts excreted to the supernatant as expected (Kipriyanov, S. M., G. Moldenhauer, and M. Little, *High level production of soluble single chain antibodies in small-scale Escherichia coli cultures*. J Immunol Methods, 1997. 200(1-2): p. 69-77). All fractions containing scFv were pooled and purified using a Ni-NTA agarose beads column (Qiagen, 5 mL beads for 1 L expression culture) and imidazole elution essentially as described (Kasturirangan, S., S. Boddapati, and M. R. Sierks, *Engineered proteolytic nanobodies reduce Abeta burden and ameliorate Abeta-induced cytotoxicity*. Biochemistry, 2010. 49(21): p. 4501-8).

Dot blot assay with human brain tissue—Postmortem human brain samples from the middle temporal gyrus (MTG) of Alzheimer's disease (AD) and cognitively normal non-demented (ND) cases were generously provided by Dr. Thomas Beach (Director of Banner/Sun Health Research Institute Brain Bank). Brain extracts from the MTG of age-matched ND and AD patients were homogenized in Tris-HCl/EDTA buffer with protease inhibitor. The homogenate was spun down to remove solids and the supernatant containing all the soluble protein was collected and adjusted to a total protein concentration of 3 mg/mL. Aliquots of 2 µL 3 mg/mL brain tissue were dotted on gridded nitrocellulose membrane and probed with anti-oligomeric tau scFv essentially as described (Zameer, A., et al., *Anti-oligomeric Abeta single-chain variable domain antibody blocks Abeta-induced toxicity against human neuroblastoma cells*. J Mol Biol, 2008. 384(4): p. 917-28). Samples were analyzed in triplicates using purified scFv. Reactivity of scFv with brain tissue samples was analyzed using ImageJ and recorded in the form of densitometric value (Kasturirangan, S., et al., *Isolation and characterization of antibody fragments selective for specific protein morphologies from nanogram antigen samples*. Biotechnol Prog, 2013. 29(2): p. 463-71). Each value was calibrated on a scale of 0 to 1 in which 0 denotes the background and 1 denotes the positive control of anti-phosphorylas b (plb) scFv.

Mouse brain tissue—Brains from 5, 8, 11 months old wild-type mice and 5, 9 and 13 months old 3×transgenic Alzheimer's (3×TG-AD) mice overexpressing human tau P301L (Oddo, S., et al., *Amyloid deposition precedes tangle formation in a triple transgenic model of Alzheimer's disease*. Neurobiol Aging, 2003. 24(8): p. 1063-70) were generously provided by Dr. Travis Dunckley (Translational Genomics, Phoenix, Ariz.). Mouse hippocampus was homogenized as described above for human brain samples.

Phage biotinylation—Phage were biotinylated for enhanced signal detection in ELISA using the EZ-Link Pentylamine-biotin kit (Thermo Scientific). A $10^{11}$ pfu/mL aliquot of phage stock (0.729 mg/ml) was incubated with Pentylamine-Biotin (4.86 mM final concentration) and 1-Ethyl-3-[3-dimethylaminopropyl] carbodiimide hydrochloride (EDC) of 0.1M final concentration at room temperature for 2 hours with stirring. Excess Pentylamine-Biotin and EDC were removed with desalting columns.

Capture ELISA—High affinity polystyrene microtiter 96-well plates were coated with 100 µl/well of 0.3 mg/ml purified single clone scFv (capture antibody) and incubated at 37° C. for two hours. After the unbound scFvs were removed, the plates were washed three times with 0.1% tween/PBS. The plates were then blocked with 2% non-fat milk/PBS at 37° C. for one hour. After a tween/PBS wash, an aliquot of 100 µl/well of 0.2 mg/ml mouse brain homogenate (target analytes) was added, incubated at 37° C. for two hours and then washed with tween/PBS. PBS was used as a negative control. A 100 µl/well aliquot of $10^7$ pfu/ml biotinylated phage (detection antibody) was incubated for coating at 37° C. for two hours. The wells were washed with tween/PBS, and then a 100 μL/well aliquot of 0.5 μg/ml avidin-HRP was added and incubated at 37° C. for one hour. The plates were washed again with tween/PBS and binding monitored using a chemiluminescent ELISA kit (SuperSignal ELISA Femto Maximum Sensitivity Substrate (Thermo Scientific)). The chemiluminescent signal was read 1 minute after addition to the mixture. The immunoreactivity signals were normalized by dividing the absolute chemiluminescent readings of the samples by that of PBS control. Within each independent experiment, the mean signal obtained from all the wild-type mice samples was used as a baseline to normalize the transgenic mice signals.

To verify that the isolated scFvs were binding oligomeric tau in the mouse brain tissue samples we used a sandwich ELISA where the scFvs were used as a capture antibody and a commercially available monoclonal antibody against hyperphosphorylated tau aggregates, AT8 (Thermo Scientific) was used as a detection antibody. AT8 binds tau forms with phosphorylated Ser202/Thr205 found in PHF-tau. An anti-mouse antibody conjugated with horse radish peroxidase (HRP) (Thermo Scientific) was used to detect bound AT8.

Size analysis of individual phage target—To determine the size of the target antigen bound by individual phage particles, a 10 μl aliquot of the fibrillar tau aggregate mixture (19.5 μg/mL, 10×dilution of the original prepared stock) was deposited on mica, and a 10 μl aliquot of $10^{12}$ pfu/ml phage was added, incubated and rinsed as described above. The aggregated mixture of rhTau 2N4R contained monomeric, oligomeric and fibrillar aggregates. AFM images (5 μm$^2$) were obtained and processed using Nanoscope Analysis. The diameter of each target antigen particle bound at the tip of the phage was calculated by taking the difference between the maximum height of the particle and the adjusted baseline. At least 6 different antigen particles for each individual clone were measured and averaged to determine the particle height of the target antigen.

Statistical analysis—Samples were analyzed by one-way ANOVA with p<0.05 standard and LSD post hoc significant differences test. All analyses were performed with SPSS 21.0 (IBM Corp., Armonk, N.Y.)

Results and Discussion

Isolation of scFvs Selectively Binding Oligomeric Tau

We utilized an AFM based panning protocol that incorporates sequential subtractive and positive panning steps (FIG. 6A) to isolate scFvs that selectively bind a toxic trimeric tau species. We first eliminated from the scFv library pool all those phage containing scFvs reactive with the control protein (BSA) (FIG. 6B) and then monomeric tau. After the subtractive panning steps, we isolated phage that selectively bound trimeric rhTau 1N4R tau using a single positive panning step. We recovered 96 phage clones from the positive panning step against trimeric tau (FIG. 6C). Phage from each of the 96 clones were prepared separately and used to verify binding specificity for trimeric tau, monomeric tau and BSA by AFM. We selected twenty clones that selectively recognized trimeric tau for further study. The DNA sequence of the twenty clones were obtained to verify the presence of full length scFv, and six distinct full-length scFvs were selected for further analysis (H2, F9, D11, G12, H7, D4 and G12). Although all six clones contained complete scFv sequences, they all each lacked a DNA base pair shortly downstream of the N-terminal NcoI site and the methionine start codon (FIG. 12) resulting in a reading frame shift. The pelB leader sequence contains multiple methionine start codons in different reading frames that may facilitate the expression of full length scFvs despite the altered reading frame resulting from the missing base pair at the N-terminal. To enhance soluble scFvs expression efficiency, we corrected the reading frame shift using PCR. We then verified that the each sequence corrected scFv maintained the same binding specificity of the original clone by AFM. Three sequence corrected clones F9T, D11C and H2A were then selected for further studies based on binding specificity and distinctive CDR sequences.

Verification of Binding Specificity to Tau Trimer

To verify that the F9T, D11C and H2A scFvs were selectively binding trimeric tau, we incubated a phage displayed version of each scFv with a sample of aggregated tau and used AFM to determine the average height of the particles bound by each phage particle. We then compared the height of the bound particles to the known height values of different tau aggregate species. The average height of at least 6 different bound antigens for each scFv was determined and compared to the size of known oligomeric tau aggregates. The target antigen size for all three scFvs correspond to the size of a rhTau 2N4R trimer (from 2.5 nm to 3.0 nm) providing further evidence that the scFvs selectively target trimeric tau (FIG. 7).

Characterization of Binding Epitopes

Purified soluble scFv protein for each corrected scFv sequence had the expected 29 kDa, the full length size for an scFv. Since the scFvs were isolated against a synthetic oligomeric tau variant, we then tested whether the purified F9T, D11C and H2A scFvs could recognize naturally occurring tau aggregates in brain tissue of an AD mouse model and whether they cross-react with random proteins in brain. All three scFv clones bound oligomeric tau aggregates preferentially present in hippocampus tissue homogenates from 9-month old 3×TG AD mouse model compared to wild-type mice (FIG. 8). The bound aggregates were detected using the anti-tau antibody AT8 to verify that the scFvs were selectively binding tau aggregates. Detection with AT8 also indicates that the tau aggregates in the brain tissue samples targeted by F9T, D11C and H2A can also be phosphorylated even though the initial antigen targets were not phosphorylated.

Since the three selected clones (i.e., F9T, D11C and H2A) contain distinctive CDR sequences, we determined whether they bind similar or different epitopes on trimeric tau using a capture ELISA protocol where purified scFv was used as a capture antibody and the phage displayed version of each scFv was used as a detection antibody. We tested different combinations of capture and detection scFvs using the 3×TG-AD mouse brain homogenates as antigen. When F9T-displayed phage was used as the detection antibody, strong signals were obtained when all three scFvs used used as capture antibodies. In contrast, when D11C-displayed phage was used as a detection antibody, lower signals were obtained with D11C and H2A as capture antibodies, and no signal with F9T; and when H2A-displayed phage was used as a detection antibody, a lower signal was obtained with D11C as the capture antibody and no signal with either F9T or H2A as capture antibodies (FIG. 9). Since F9T-displayed phage gives a strong signal even when F9T scFv is used as the capture antibody, F9T recognizes a trimer specific epitope that occurs in multiple locations on the tau aggregate. The antigen recognized by D11C may also have multiple epitopes since D11C phage showed reactivity to tau aggregates captured by D11C scFv. However the antigen recognized by H2A may have only a single epitope since no signal was obtained with tau aggregates captured by the H2A scFv. Since F9T phage produced the strongest immunoreactivity with brain extracts retained by all three scFvs as capture antibody, we used F9T phage as the detection antibody in all further capture ELISAs.

Time Dependent Presence of Oligomeric Tau in AD Mouse Brain Tissue

We analyzed how oligomeric tau concentration varied with time in the 3×TG-AD mice using the three scFvs against oligomeric tau. In the 3×TG mouse model, insoluble tau tangles are typically detected around 12-15 months of age, however we find that oligomeric tau levels are already high at 5-months of age, peak at 9-months and decline by 13-months (FIG. 10). As expected we see similar trends with all three scFvs since each scFv recognizes different epitopes of the same oligomeric tau species. Samples from age-matched wild-type mice did not show the presence of any oligomeric tau reactive with these scFvs. The results from this mouse model indicate that the concentration of oligomeric tau species increases at early time points (5-9 months) before insoluble tau tangles begin to form, and then decreases after neurofibrillary tangles begin to form (12-15 months) suggesting that the oligomeric tau species may be incorporated into the NFTs. Since oligomeric tau aggregates are already present at 5-months well before presence of NFTs they have promise as an early diagnostic for AD.

Analysis of Post-Mortem Human Brain Tissue

Since the scFvs effectively detected oligomeric tau species present in brain tissue from an AD mouse model, we next probed post-mortem human middle temporal gyrus (MTG) extracts from different Braak stages for the presence of oligomeric tau using the F9T scFv (FIG. 11). Oligomeric tau was readily detected in the human brain samples using F9T. Interestingly the concentration of oligomeric tau in the samples increases with increasing Braak stage as there is only minimal oligomeric tau in the ND Braak stage I-II samples, higher values in the ND Braak stage I-II samples with slight plaques, higher values again in AD samples with moderate plaques (Braak stage III-IV) and the highest signals in AD samples with heavy plaques (Braak stage V-VI). There is a significant difference between the levels of oligomeric tau in the AD samples compared to both the ND samples without plaques and the ND samples with slight plaques. These results indicate that morphology specific reagents such as F9T can be used to detect the presence of oligomeric tau species in human samples and have promise not only as early diagnostics for AD but also to help stage progression of the disease.

Summary

Aggregates of Aβ and tau are the primary protein constituents of the hallmark senile plaques and neurofibrillary tangles of AD. While many studies have focused on accumulation and aggregation of Aβ as an initiating factor in AD pathogenesis and neuronal death with tau dysfunction considered to be a downstream event following Aβ aggregation, other studies suggest that tau interacts with AO to accelerate the progression of AD, and that reducing aggregated tau levels are also important to ameliorate AD symptoms. Aβ and tau aggregation may be linked by separate mechanisms driven by a common upstream cause. Numerous studies have implicated the role of soluble oligomeric Aβ species in mediating toxicity in AD, and evidence now suggests that oligomeric tau may also play toxic roles in AD. Recent studies indicate that soluble tau species including oligomeric, prefibrillar and immature prefilament forms play more crucial roles in AD than the hallmark NFTs which instead may rather play an adaptive and protective role. Oligomeric tau has been shown to have prion-like self-propagating features and can be endocytosed into neurons where they can induce endogenous tau pathology in vivo. Therefore the roles of oligomeric and fibrillar tau species in AD progression is getting increasing attention and oligomeric tau is a promising therapeutic target for AD. Because of the diversity of tau species that may be present in the human brain due to the alternative post-transcriptional splicing and post-translational modifications that may occur, there is a critical need to develop reagents that can selectively identify individual tau aggregate variants to probe the roles of the various forms in disease progression and to assess their value as diagnostic and therapeutic targets.

We previously reported that a trimeric, but not monomeric or dimeric tau species was neurotoxic at low nanomolar levels. Here we isolated three different scFvs (F9T, D11C and H2A) that selectively recognize this toxic trimeric tau species. All three scFvs have unique CDR sequences, bind to different epitopes on the tau aggregate and detect oligomeric tau species in an AD mouse model by 5-months of age. While NFTs are a hallmark feature of AD, oligomeric tau species may play an intermediate role in tau aggregation and have been shown to play an important role in neuronal toxicity, so identification and quantification of oligomeric tau variants has great promise as an biomarker for early diagnosis of AD. Here we show that the oligomeric tau levels can be used to differentiate post-mortem human AD brain tissue samples from age-matched cognitively normal cases. Quantification of oligomeric tau also distinguishes the post-mortem human samples according to Braak stage which is based on Aβ plaque and abnormal tau immunohistochemical staining.

Example 5

Trimeric Tau Is Toxic to Human Neuronal Cells at Low Nanomolar Concentrations

Alzheimer's disease (AD) is the most common form of dementia, characterized by progressive cognitive impairment, cerebral atrophy, and neuronal loss, with death generally occurring four to eight years after diagnosis. Two pathological hallmarks of AD, extracellular neuritic plaques primarily composed of amyloid beta (Aβ) and intracellular neurofibrillary tangles (NFTs) primarily composed of tau protein, were originally identified in 1907 by Dr. Alzheimer. While great strides have been made in understanding the mechanisms that promote aggregation of Aβ and tau into the hallmark plaques and tangles, comparatively little progress has been achieved in halting or curing the disease. Analysis of familial AD cases implicated production of Aβ as a primary factor in progression of AD, leading to the rise of the amyloid cascade hypothesis which states that Aβ misfolding and aggregation initiates AD pathogenesis and triggers other effects such as tau phosphorylation, aggregation, and tangle formation. The amyloid hypothesis had dominated the field for more than a decade and has driven numerous clinical studies for therapeutic interventions including several immunization studies targeting Aβ. However failure of several clinical trials targeting Aβ has cast doubt on its relevance as a therapeutic target. Increasing evidence indicates that tau also plays an important role in the progression of AD. Tau misfolding and aggregation can take place independently of amyloid formation, and in many cases the presence of tau lesions is associated with AD without presence of Aβ aggregates. Clearance of Aβ plaques without reducing soluble tau levels is insufficient to ameliorate cognitive decline in double transgenic mice overexpressing Aβ and tau P301L. These results among many others indicate that oligomeric tau may be an important therapeutic target for AD.

Tau in its monomeric form is a microtubule associated protein crucial for microtubule assembly and stabilization. Six major tau isoforms can be generated by alternative posttranscriptional splicing of exon 2 and exon 3 on the N-terminal projection domain and of exon 10 (Repeat 2) on the assembly domain (FIG. 14). Tau contains three or four similar repeats in the microtubule binding domain (MBD) that binds to and helps promote microtubule stability and function. For example, Repeat 2 and Repeat 3 contain hexapeptide motifs of PHF6* and PHF6, respectively (FIG. 14). These motifs increase the tendency to form β-sheet structures that can interact with tubulins to form microtubules and also facilitate self-assembly to generate oligomeric and higher-order aggregates. Tau isoforms with or without the second microtubule-binding repeat can aggregate, but only the isoforms with the second repeat can form extended oligomeric forms mediated by disulfide linkages due to the additional cysteines in the second repeat (FIGS. 14 and 15). Therefore, in this study we utilized tau isoforms containing the second repeat unit to study the role of tau aggregation in neurotoxicity.

Hyperphosphorylation of tau is required for the release of tau from microtubules and its mislocalization to the somatodendritic compartment enabling tau to self-associate into oligomers and higher-order aggregates. However, the hyperphosphorylation of tau is not directly related to its toxicity but rather a mechanism to regulate its interaction with tubulin to stabilize microtubules and to regulate transport along microtubules. Expression of exogenous tau in mature hippocampal neurons leads to blockage of transport along microtubules and degeneration of synapses that can be rescued by phosphorylation of tau by kinase MARK2 to unblock the microtubule tracks. Significantly, tau in the extracellular space is reported to be less phosphorylated than intracellular tau and more toxic in its dephosphorylated state. Extracellular oligomers of recombinant full-length human tau protein were shown to be neurotoxic in mice and impair memory consolidation, and similar work at other labs has shown similar effects with recombinant tau oligomers and tau oligomers composed of hyperphosphorylated tau from AD brain. Thus, the hyperphosphorylation of tau associated with disease may be a causal factor in tau self-association into oligomers, but the hyperphosphorylation of tau in and of itself may not be the basis for the toxicity of extracellular tau oligomers.

Neurofibrillary tangles (NFTs) have traditionally been correlated with neuronal loss and considered to be key intracellular indicators of AD. Approaches for targeting tau aggregation have focused on inhibiting hyperphosphorylation and fibril formation, reducing total tau levels, or stabilizing microtubules. However, accumulating evidence suggests that soluble oligomeric rather than insoluble fibrillar tau species are neurotoxic and play an important role in the onset and progression of AD. Although NFTs are a hallmark feature of AD, they can exist in AD neurons for up to 20 to 30 years before postmortem confirmation and therefore are less likely to induce immediate toxicity in AD brain. In animal models of tauopathy, the presence of NFTs does not correlate well with neuronal loss and memory deficits. Reduction in neuronal loss and improvement in memory performance are observed despite an increase in NFTs. In addition, the presence of NFT pathology does not localize well with areas of neuronal loss, synapse loss or dysfunction in the hippocampus along with microglial activation occurs well before the presence of NFTs. In contrast, oligomeric tau was implicated in numerous studies as playing a key role in AD progression and to be a primary initiator of neurotoxicity and neurodegeneration. Oligomeric tau has been identified in early stages of neuronal cytopathology in AD and closely correlates with hyperphosphorylation on microtubule-binding sites. Tau oligomers can propagate endogenous tau pathology throughout the brain similarly to prions, demonstrating their neuronal toxicity. The presence and concentrations of two tau oligomers (140 kDa and 170 kDa) correlate with memory loss in various age rTg4510 mice. Oligomeric tau also induces synaptic and mitochondrial dysfunction. Although tau is predominantly intracellular, the role of extracellular tau is gaining attention as extracellular oligomeric tau can have acute effects on long-term potentiation in hippocampal slices and can transmit pathology to healthy neurons. Detection of oligomeric tau levels in human CSF and blood is also a promising AD diagnostic biomarkers along with total and hyperphosphorylated tau levels. Because of the important role of oligomeric tau in AD and the recognition of the importance of extracellular tau in disease, it is critical to identify the key toxic tau species in disease etiology. Here we show our studies of the extracellular neurotoxicity of monomeric, dimeric, and trimeric forms of two four-repeat recombinant human tau variants to help identify the key tau species involved in the onset and progression of AD.

2. Materials and Methods 2.1. Recombinant Human Tau (rhTau) Preparation and Purification. rhTau was purified as monomers from bacterial (BL21 DE3) clones with tau constructs in the pET21B and pET29a vectors. Standard methods were used to grow and induce the protein with 1 mM IPTG. Pelleted cells were lysed with CelLytic B lysis buffer, lysozyme, benzonase, and protease inhibitors according to the manufacturer's protocol (Sigma Aldrich, St. Louis, Mo.). Cation exchange (GE-Healthcare Life Sciences) was used for the first step of purification with SPSepharose resin for both tau constructs, and 300 mM NaCl in 25 mM Tris-HCl pH 7.4 was used to elute tau protein. Amicon Ultra Centrifugal Devices (Millipore) were used to buffer-exchange the protein preparations into 50 mM Tris-HCl pH 7.4. Protein concentration was determined using a BCA assay (Thermo Fisher Scientific). Tau oligomers were generated by incubating tau monomers at a concentration of 5 μM in 50 mM Tris buffer pH 7.4 with 100 mM NaCl at 37° C. overnight. The monomeric and oligomeric species were resolved by 6% PAGE, eluted, and buffer-exchanged into 50 mM Tris-HCl. Fractions were analyzed by nonreducing SDS-PAGE to minimize degradation of oligomeric proteins and silver staining to enhance the signal and to verify the purity of tau variants. Protein concentration was determined using the BCA assay.

2.2. Height Distribution Analysis. AFM sample preparation and imaging were performed as described previously (H. Barkhordarian, S. Emadi, P. Schulz, and M. R. Sierks, "Isolating recombinant antibodies against specific protein-morphologies using atomic force microscopy and phage display technologies," *Protein Engineering, Design and Selection*, vol. 19, no. 11, pp. 497-502, 2006; A. Zameer, P. Schulz, M. S. Wang, and M. R. Sierks, "Single chain Fv antibodies against the 25-35Aβ fragment inhibit aggregation and toxicity of Aβ42," *Biochemistry*, vol. 45, no. 38, pp. 11532-11539, 2006; S. Emadi, H. Barkhordarian, M. S. Wang, P. Schulz, and M. R. Sierks, "Isolation of a human single chain antibody fragment against oligomeric α-synuclein that inhibits aggregation and prevents α-synuclein-induced toxicity," *Journal of Molecular Biology*, vol. 368, no. 4, pp. 1132-1144, 2007; A. Zameer, S. Kasturirangan, S. Emadi, S. V. Nimmagadda, and M. R. Sierks, "Anti-oligomeric Aβ single-chain variable domain antibody blocks Aβ-induced toxicity against human neuroblastoma cells," *Journal of Molecular Biology*, vol. 384, no. 4, pp. 917-928, 2008; S. Emadi, S. Kasturirangan, M. S. Wang, P. Schulz, and M. R. Sierks, "Detecting morphologically distinct oligomeric forms of α-synuclein,"*The Journal of Biological Chemistry*, vol. 284, no. 17, pp. 11048-11058, 2009; M. S. Wang, A. Zameer, S. Emadi, and M. R. Sierks, "Characterizing antibody specificity to different protein morphologies by AFM," *Langmuir*, vol. 25, no. 2, pp. 912-918, 2009.) Aliquots of 10 µL 0.50 µM purified tau variants in 50 mM Tris-HCl buffer were deposited on separate mica pieces for imaging using MultiMode AFM Nanoscope IIIA system (Veeco/Digital instruments, Santa Barbara, Calif.) which was set in tapping mode and equipped with silicon AFM probes (VISTA probes, Nanoscience Instruments). Height distribution analysis of the different tau samples was fit to a normal distribution probability model using Gwyddion 2.20. All detectable protein molecules were assumed to be spherical and the height values approximate their diameters.

2.3. Cell Culture and Treatments. SH-SY5Y human neuroblastoma cell lines (American Tissue Culture Collection) were cultivated in tissue culture flask (Falcon by Becton Dickinson Labware). Cells were grown in a medium containing 44% v/v Ham's F-12 (Irvine Scientific), 44% v/v MEM Earle's salts (Irvine Scientific), 10% v/v denatured fetal bovine serum (FBS) (Sigma Aldrich), 1% v/v MEM nonessential amino acids (Invitrogen), and 1% v/v antibiotic/antimycotic (Invitrogen). Media were renewed once every two to three days. The cells were passaged to a new flask when they were confluent in the flask. For toxicity studies, the SH-SY5Y cells were seeded in a 48-well cell culture cluster plate (Costar by Corning Incorporated) with 5×104 cells/well in 300 µL fresh medium. Each experiment was conducted in triplicate. Cell density was estimated by reading a fixed volume on a hemocytometer. After growth in a 37° C. incubator for 24 hours, the tissue culture media were replaced with fresh serum-free media for the neurotoxicity test on nondifferentiated cells. To investigate tau toxicity on cholinergic neurons, a duplicate set of the cultured cells was induced into cholinergic-like phenotype by incubation with retinoic acid at a final concentration of 10 µM for 3 to 5 days (S. Emadi, S. Kasturirangan, M. S. Wang, P. Schulz, and M. R. Sierks, "Detecting morphologically distinct oligomeric forms of α-synuclein,"*The Journal of Biological Chemistry*, vol. 284, no. 17, pp. 11048-11058, 2009; S. Pahlman, J. C.

Hoehner, E. Nanberg et al., "Differentiation and survival influences of growth factors in human neuroblastoma," *European Journal of Cancer A*, vol. 31, no. 4, pp. 453-458, 1995; M. Encinas, M. Iglesias, Y. Liu et al., "Sequential treatment of SH-SY5Y cells with retinoic acid and brain-derived neurotrophic factor gives rise to fully differentiated, neurotrophic factor-dependent, human neuron-like cells," *Journal of Neurochemistry*, vol. 75, no. 3, pp. 991-1003, 2000;] S. P. Presgraves, T. Ahmed, S. Borwege, and J. N. Joyce, "Terminally differentiated SH-SY5Y cells provide a model system for studying neuroprotective effects of dopamine agonists," *Neurotoxicity Research*, vol. 5, no. 8, pp. 579-598, 2003.). The cultivated nondifferentiated and cholinergic-like neurons were treated with monomeric, dimeric, and trimeric variants of 1N4R and 2N4R at final concentrations of 2.26 nM, 4.50 nM, 11.15 nM, and 15.50 nM. A PBS negative control was used as a standard for subsequent LDH assay analysis. Cultures were incubated with tau species at 37° C. and sampled at 3, 18, 24, and 48 hour time points by harvesting 30/well aliquots 5 of culture supernatant.

2.4. LDH Assay. The LDH protocol is adapted from a commercial kit (Sigma Aldrich) based on the generic protocol of Decker and Lohmann-Matthes. The LDH assay was performed as described previously (A. Zameer, P. Schulz, M. S. Wang, and M. R. Sierks, "Single chain Fv antibodies against the 25-35Aβ fragment inhibit aggregation and toxicity of Aβ42," *Biochemistry*, vol. 45, no. 38, pp. 11532-11539, 2006.). Absorbance was measured at 490 nm (reference wavelength 690 nm). Relative absorbance values were calculated by subtracting the reference values from the values obtained at 490 nm. LDH % values greater than 150 are considered toxic.

2.5. Statistical Analysis. The relative absorbance values of all samples were normalized to those of controls which were set as 100% for each independent experiment. Group mean values were analyzed by one-way ANOVA with $P<0.05$ standard and LSD post hoc significant differences test. All analyses were performed with SPSS 21.0 (IBM Corp., Armonk, N.Y.).

3. Results 3.1. rhTau Aggregate Analysis. We expressed recombinant human tau in a bacterial host system to eliminate any posttranslational phosphorylation of tau and therefore remove any potential effects that phosphorylation may have on tau aggregation or loss of function. The resulting nonphosphorylated human recombinant tau (NPrhTau) monomers contain reactive cysteine groups with free thiols, facilitating the formation of intramolecular disulfide bonds to make stable nonreactive monomers and the formation of intermolecular disulfide bonds to produce tau oligomers and higher degree aggregates (FIG. 15). The polymerization reaction is controlled by incubation time and protein concentration. The nonreactive monomeric, dimeric, and trimeric forms of both the 2N4R and 1N4R splice variants generate stable aggregate morphologies with defined size profiles dependent on the degree of oligomerization and length of the splice variant as evidenced by SDS-PAGE and AFM height distribution analysis (FIG. 16). The oligomer heights increment for each additional monomeric tau unit is fixed within a certain isoform, which is 0.5 nm for 1N4R variants and 1.0 nm for the 2N4R variants (FIG. 16). The size of each respective 2N4R species is also larger than the corresponding 1N4R species (FIG. 16) as expected given that tau 2N4R contains the extra N-terminal insert compared with the 1N4R variants.

3.2. Extracellular rhTau Induced Neurotoxicity Test. While neither the monomeric or dimeric forms of tau from either the 1N or 2N splice variants displayed detectable toxicity, the trimeric form of both variants exerted marked toxicity toward nondifferentiated (FIG. 17(*a*)) and retinoic acid induced cholinergic-like neurons (FIG. 17(*b*)) with LDH values well above the toxic threshold of 150 at low nanomolar concentrations (11.15 nM, and 15.50 nM). The full length 2N4R trimeric tau form displayed significantly higher toxicity than the 1N4R trimeric form toward nondifferentiated neurons (FIG. 17(*a*)), although the effect is diminished in the cholinergic-like neurons (FIG. 17(*b*)). When trimeric tau was added to nondifferentiated SH-SY5Y cells, an increase in toxicity was observed with time at the highest concentrations for both the 1N4R (FIGS. 18(*a*)), and 2N4R (FIG. 18(*b*)) trimeric variants. However, when trimeric tau was added to the cholinergic-like neurons, the toxicity of the 1N (FIGS. 18(c)) and 2N (FIG. 18(d)) variants was relatively consistent over the first 24 hours, but increased after 48 hours. Both variants of trimeric tau showed increased toxicity toward the cholinergic-like neurons compared to the nondifferentiated neurons at short incubation times (FIG. 19(a)) but the reverse was observed at longer incubation times (FIG. 19(b)).

4. Discussion

While the amyloid cascade hypothesis has dominated studies into the etiology of AD over the last decade or more, the importance of tau in the onset and progression of AD is steadily becoming more apparent. Tau pathology has been observed in the absence of Aβ deposits in children and young adult cases, and tau aggregates in the entorhinal-hippocampal regions precede the onset of Aβ pathology. Numerous studies have shown that various oligomeric forms of Aβ are toxic to neurons and can impair cognitive performance, thus implicating their potential role as valuable biomarkers for diagnosing AD. Similar to the important role of various soluble oligomeric Aβ species in AD, different soluble oligomeric forms of tau may also play a critical role in AD, also causing neuronal loss and cognitive dysfunction. Therefore to facilitate diagnoses and therapeutic treatments for AD, it is important to identify the key tau species involved in the onset and progression of the disease. Given that tau has multiple splice variants and posttranslational modification sites, we attempted to simplify the complex diversity of tau forms by focusing on two nonphosphorylated human recombinant tau isoforms, 1N4R and 2N4R. These two four-repeat (4R) isoforms of tau both have all four repeats of the microtubule-associated domains and are more prone to form the aggregates readily phosphorylated by brain protein kinases than those with only three repeats (3R) due to the presence of Repeat 2 with a microtubule-affinity enhancing hexapeptide motifs and an additional cysteine that forms disulfide linkages to stabilize the aggregates.

The most disease-relevant tau material to use to study toxicity of extracellular tau forms would be well characterized tau oligomers purified from AD cerebrospinal fluid (CSF) using methods to preserve their posttranslational modifications, including phosphorylation, glycation, ubiquitination, aggregation, and truncation. Preparations from several non-AD and AD cases would be necessary to understand the significance of the results. Here we performed an initial study focused specifically on unmodified tau protein oligomers and control monomer to specifically understand the relevance of oligomer structure to extracellular toxicity.

We determined the toxicity of the different tau variants using both nondifferentiated and cholinergic-like neuroblastoma cell lines to determine how aggregate size and cell phenotype affected toxicity. Cholinergic cells are particularly vulnerable in AD with significant neuronal loss in the nucleus basalis of Meynert (NBM), that is, the hippocampus and the cortex. NBM is enriched in cholinergic cells and undergoes degeneration and a significant decrease of acetylcholine production in AD. Decreased levels of acetylcholine and a number of other cortical cholinergic markers lead to clinical dementia and impairment in cognitive function, indicating that cholinergic cells are particularly vulnerable in AD. Here we show that trimeric, but not monomeric or dimeric, tau is toxic to neuronal cells at low nanomolar concentrations and that the full-length 2N tau variant is more toxic than the shorter 1N variant to nondifferentiated neurons (FIG. 17). Both trimeric tau variants cause toxicity to both nondifferentiated SH-SY5Y cells and retinoic acid induced cholinergic-like neurons when tau was applied extracellularly at nanomolar levels (FIG. 18). However, the cultured cholinergic-like neurons show increased susceptibility to trimeric tau induced toxicity at short incubation times compared with similar nondifferentiated neurons (FIG. 19(a)), perhaps partially accounting for the increased vulnerability of cholinergic-like neurons in AD. Since the nondifferentiated cells were equally susceptible to trimeric tau induced toxicity at longer incubation times (FIG. 19(b)), these results suggest that toxicity of extracellular trimeric tau is not dependent on receptors or proteins specifically associated with cholinergic cells but that toxicity might be facilitated by them. Our results are consistent with a recent study showing that low molecular weight (LMW) misfolded tau species exclusive of monomeric tau can be endocytosed by neurons and transported both anterogradely and retrogradely to induce endogenous tau pathology in vivo while fibrillar tau and brain-derived filamentous tau cannot be endocytosed. This suggests that tau toxicity may be spread through cells in certain brain regions by endocytosis of trimeric and larger oligomeric forms of tau and that this uptake is facilitated in cholinergic neurons. Neuronal toxicity of oligomeric tau may share similar properties to that of oligomeric Aβ where the critical feature involved in neuronal toxicity is the aggregation state of the protein more than posttranslational modifications.

While there are a wide variety of tau variants that occur in vivo including different posttranslational modifications, splice variants, and aggregated species, this study begins to more systematically probe the role of selected tau variants in AD. Further studies are needed to determine the contribution of splice variants and AD-specific posttranslational modifications found in extracellular tau to the toxicity of the tau variants and to how these tau variants affect other neuronal models including primary neurons or induced pluripotent stem cells. Well characterized reagents that can selectively identify specific tau variants and morphologies will be useful for these further studies.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An antibody or antibody fragment that specifically recognizes oligomeric tau but does not bind monomeric tau, fibrillar tau or non-disease associated forms of tau, wherein the antibody fragment comprises amino acid sequence SEQ ID NO:1, SEQ ID NO:9, SEQ ID NO:11, SEQ ID NO:13, SEQ ID NO:15, SEQ ID NO:17, or SEQ ID NO:19.

2. The antibody or antibody fragment of claim 1, wherein the oligomeric tau is soluble.

3. The antibody or antibody fragment of claim 1, wherein the oligomeric tau is dimeric tau or trimeric tau.

4. The antibody or antibody fragment of claim 3, wherein the oligomeric tau is trimeric tau.

5. The antibody or antibody fragment of claim 1, wherein said antibody fragment is isolated according to a method comprising the steps of: a. a negative panning of a scFV phage library wherein said negative panning eliminates phage that bind to non-desired antigens wherein said negative panning comprises serially contacting phage with: (i) a generic protein; and (ii) mononeric forms of tau; and monitoring the binding of said phage to the generic protein and monomeric forms of tau using Atomic Force Microscope (AFM) Imaging and repeating steps (i) and (ii) until no phage is observed binding to antigen by said AFM imaging to produce an aliquot of phage; b. contacting the aliquot of phage with tau oligomers and incubating for time sufficient to allow binding of phage to said oligomers; and c. eluting the bound phage particles from step (b).

6. The antibody or antibody fragment of claim 5, wherein the tau oligomer is trimeric tau 4N1R.

7. The antibody or antibody fragment of claim 5, wherein the generic protein is bovine serum albumin (BSA).

8. The antibody or antibody fragment of claim 5, wherein the negative panning further comprises serially contacting phage with brain derived control samples that do not contain oligomeric tau.

9. The antibody or antibody fragment of claim 5, wherein the observing of the binding of the phage to the antigen is by using Atomic Force Microscope (AFM) Imaging.

10. The antibody or antibody fragment of claim 5, wherein the negative panning is repeated until less than 0-10% phage was observed by AFM imaging as binding to antigen in step (a).

11. The antibody fragment of claim 1, wherein said antibody fragment does not contain the constant domain region of an antibody.

12. The antibody fragment of claim 1, wherein the antibody fragment comprises amino acid sequence SEQ ID NO:1, SEQ ID NO:9 or SEQ ID NO:11.

13. A method of inhibiting the aggregation of tau comprising contacting a composition that comprises tau oligomers with an antibody or antibody fragment of claim 1.

14. The method of claim 13, wherein said aggregation of tau is in a cell.

15. The method of claim 13, wherein said aggregation of tau is in brain tissue.

16. The method of claim 13, wherein said contacting with an antibody or antibody fragment decreases the rate of formation of tau aggregates as compared to said rate in the absence of the antibody or antibody fragment.

17. The method of claim 13, wherein the tau oligomers are dimeric or trimeric tau.

18. A method of detecting the presence of tau in a physiological sample comprising contacting a sample with a composition comprising the antibody or antibody fragment of claim 1 and determining the binding of said composition with said physiological sample; wherein binding of said composition to said physiological sample is indicative of the presence of tau oligomers in said physiological sample wherein said presence of said tau oligomers is indicative of early stage AD, frontotemporal dementia, other tauopathies or neurodegeneration following traumatic brain injury.

19. The method of claim 18, wherein the physiological sample is brain tissue, serum, cerebrospinal fluid (CSF), blood, urine or saliva.

20. The method of claim 17, wherein the tau oligomers are trimeric tau.

21. The method of claim 17, wherein the tau oligomers are soluble.

22. A method of inhibiting the accumulation of tau in the brain of a mammal comprising administering to said mammal a composition comprising an an antibody or antibody fragment of claim 1.

* * * * *